United States Patent
Ozee et al.

(10) Patent No.: US 9,956,147 B2
(45) Date of Patent: May 1, 2018

(54) EMULSION CONTAINING A DISPERSION OF BISMUTH OXYCHLORIDE

(71) Applicant: L'ORÉAL, Paris (FR)

(72) Inventors: Emmanuelle Ozee, Thiais (FR); Laurence Guerchet, Le Bouscat (FR); Xavier Blin, Paris (FR); Nathalie Delattre, Sonchamp (FR)

(73) Assignee: L'OREAL, Paris (FR)

( * ) Notice: Subject to any disclaimer, the term of this patent is extended or adjusted under 35 U.S.C. 154(b) by 0 days. days.

(21) Appl. No.: 15/217,527

(22) Filed: Jul. 22, 2016

(65) Prior Publication Data

US 2017/0014319 A1 Jan. 19, 2017

Related U.S. Application Data

(62) Division of application No. 13/384,817, filed as application No. PCT/FR2010/051398 on Jul. 2, 2010, now Pat. No. 9,452,114.

(60) Provisional application No. 61/244,457, filed on Sep. 22, 2009, provisional application No. 61/244,458, filed on Sep. 22, 2009, provisional application No. 61/244,461, filed on Sep. 22, 2009.

(30) Foreign Application Priority Data

Jul. 20, 2009 (FR) ..................................... 09 55006
Jul. 20, 2009 (FR) ..................................... 09 55008
Jul. 20, 2009 (FR) ..................................... 09 55009
Jun. 2, 2010 (FR) ..................................... 10 54303

(51) Int. Cl.
*A61Q 1/02* (2006.01)
*A61Q 1/12* (2006.01)
*A61K 8/891* (2006.01)
*A61K 8/20* (2006.01)
*A61K 8/04* (2006.01)
*A61K 8/06* (2006.01)
*A61K 8/37* (2006.01)
*A61K 8/58* (2006.01)
*A61Q 19/00* (2006.01)
*A61K 8/34* (2006.01)
*A61K 8/92* (2006.01)

(52) U.S. Cl.
CPC ............... *A61K 8/20* (2013.01); *A61K 8/042* (2013.01); *A61K 8/06* (2013.01); *A61K 8/34* (2013.01); *A61K 8/37* (2013.01); *A61K 8/585* (2013.01); *A61K 8/891* (2013.01); *A61K 8/92* (2013.01); *A61Q 1/02* (2013.01); *A61Q 1/12* (2013.01); *A61Q 19/008* (2013.01); *A61K 2800/31* (2013.01); *A61K 2800/436* (2013.01)

(58) Field of Classification Search
CPC . A61Q 1/02; A61K 8/064; A61K 8/37; A61K 8/891
See application file for complete search history.

(56) References Cited

U.S. PATENT DOCUMENTS

| 4,994,264 | A | 2/1991 | Verdon et al. |
| 6,333,053 | B1* | 12/2001 | Simon .................. A61K 8/8147 424/401 |
| 6,455,055 | B1 | 9/2002 | Walling et al. |
| 6,743,285 | B1 | 6/2004 | Anselmann et al. |
| 6,906,015 | B1 | 6/2005 | Shiloach et al. |
| 8,084,506 | B2 | 12/2011 | Zhao |

(Continued)

FOREIGN PATENT DOCUMENTS

| AU | 9521833 A | 1/1996 |
| EP | 1 327 435 | 7/2003 |

(Continued)

OTHER PUBLICATIONS

Starch, M., "Silicone's benefits in antiaging skin care", Nov. 13, 2008, Cosmetics & Toiletries, Allured Business Media (printed from http://www.cosmeticsandtoiletries.com/formulating/category/antiaging/34408409.html).*

"Belsil PDM 1000", Wacker Silicones, Version 1.3, last revision Nov. 30, 2011. (Year: 2011).*

International Search Report dated Feb. 24, 2011 in PCT/FR10/51398 Filed Jul. 2, 2010.

(Continued)

*Primary Examiner* — Gina C Justice
(74) *Attorney, Agent, or Firm* — Oblon, McClelland, Maier & Neustadt, L.L.P.

(57) ABSTRACT

The invention relates to a cosmetic composition in particular in the form of an emulsion for topical application to keratin materials, in particular the skin, comprising, in a physiologically acceptable medium:

(i) at least one dispersion (pre-dispersion) of bismuth oxychloride (CI 77163) in an oily dispersant chosen from a) monoesters of formula $R_1COOR_2$ in which $R_1$ represents a linear or branched hydrocarbon-based chain comprising from 4 to 40 carbon atoms, preferably from 4 to 30 carbon atoms, and preferentially from 7 to 20 carbon atoms, and $R_2$ represents a branched hydrocarbon-based chain containing from 3 to 40 carbon atoms, preferably from 10 to 30 carbon atoms, and preferentially from 16 to 26 carbon atoms; b) oils whose solubility parameter at 25° C., δa, is greater than 6 $(J/cm^3)^{1/2}$, and mixtures thereof, and (ii) at least one oil chosen from hydrocarbon-based oils having a refractive index greater than 1.42 and a solubility parameter at 25° C., δa, greater than 1 $(J/cm^3)^{1/2}$, silicone oils, in particular phenyl silicone oils, and mixtures thereof.

Applied to the skin, this composition imparts a luminous effect to the complexion.

14 Claims, No Drawings

(56) References Cited

U.S. PATENT DOCUMENTS

| | | |
|---|---|---|
| 2003/0157042 A1 | 8/2003 | Collin et al. |
| 2005/0048014 A1 | 3/2005 | Linz et al. |
| 2005/0175562 A1 | 8/2005 | Hadasch et al. |
| 2005/0233916 A1 | 10/2005 | Polonka et al. |
| 2005/0233917 A1 | 10/2005 | Shiloach et al. |
| 2007/0166247 A1 | 7/2007 | Aliano et al. |
| 2008/0102049 A1 | 5/2008 | McDermott |
| 2008/0152681 A1 | 6/2008 | Brown et al. |
| 2009/0142382 A1 | 6/2009 | Shah et al. |
| 2009/0191139 A1 | 7/2009 | Shimizu et al. |

FOREIGN PATENT DOCUMENTS

| | | |
|---|---|---|
| FR | 2 903 006 | 1/2008 |
| JP | 8-3535 A | 1/1996 |
| JP | 2000-239119 A | 9/2000 |
| JP | 2001-172120 A | 6/2001 |
| JP | 2003-508575 A | 3/2003 |
| JP | 2005-194277 A | 7/2005 |
| JP | 2007-518748 A | 7/2007 |
| JP | 2007-518761 A | 7/2007 |
| WO | 2005 000252 | 1/2005 |
| WO | WO 2005/070382 A1 | 8/2005 |
| WO | WO 2005/070384 A1 | 8/2005 |
| WO | 2009 067516 | 5/2009 |

OTHER PUBLICATIONS

Office Action dated Jul. 22, 2014 in Japanese Patent Application No. 2012-521077.
Office Action dated Apr. 27, 2015 in Japanese Patent Application No. 2012-521077 (submitting English translation only).
Rona Launches Biron Liquid Silver, Household and Personal Products Industry, v. 10, No. 10, Oct. 2003, p. 142.
SU 436844 A, "High luster mother-of-pearl pastes from bismuth oxychloride and castor oil using polyethylene glycol esters alcohol as dispersing agent", Dec. 30, 1974, Abstract (Derwent ACC No. 1975-388A6W).
Nishida, M., et al. "Cosmetic composition", JP 2000239119 A, Sep. 5, 2000, translation.
Belsil PDM 1000, Wacker Silicones, Nov. 30, 2011.

\* cited by examiner

EMULSION CONTAINING A DISPERSION OF BISMUTH OXYCHLORIDE

CROSS-REFERENCE TO RELATED APPLICATIONS

This application is a divisional application of Ser. No. 13/384,817 filed Apr. 19, 2012, which is a 371 of PCT/FR2010/051398, filed Jul. 2, 2010, which claims the benefit of priority from U.S. Provisional Application Nos. 61/244,457, 61/244,458 and 61/244,461, all filed Sep. 22, 2009, which claims priority from French Application Nos. FR 0955006, FR 0955008, FR 0955009, all filed Jul. 20, 2009, and FR 1054303, filed Jun. 2, 2010, the entire contents of each are hereby incorporated herein by reference.

The present invention relates to compositions for caring for and/or making up the skin, which are especially intended to impart luminosity or a light effect.

The terms "luminosity" or "light effect" are understood according to the invention to mean the characteristic of light reflection, diffuse and continuous reflection over the skin. Indeed, the skin naturally reflects a portion of the incident light. The "light effect" according to the invention makes it possible to increase this reflection, which gives the makeup a more luminous and more radiant look. The compositions according to the invention may also impart a healthy glow effect.

The expression "healthy glow effect" is understood to mean a natural coloration of the skin, with an improvement in the dull appearance of the complexion (desaturating or chromatic and anti-dull complexion effect).

The expression "composition for caring for and/or making up keratin materials" according to the invention is understood to mean compositions different from rinse-off cleansing compositions.

In particular, they will be compositions for caring for and/or making up the skin of the face and/or of the body, especially facial skin.

According to one particular embodiment, the composition of the invention will comprise at least one colorant.

Consumers are in search of novel cosmetic products for improving the appearance of keratin materials and especially the skin, in particular the surface appearance (visible and/or tactile unevenness) and/or the skin complexion, an external sign of a healthy glow, health and youth.

Furthermore, they are in search of novel cosmetic products that have a fluid, fresh and fine texture combined with a care and/or makeup result that is fine, non-powdery, non-marking but nevertheless gives coverage and is luminous in order to minimize defects, in particular the surface appearance (visible and/or tactile unevenness), and impart luminosity to the complexion, an external sign of a healthy glow, health and youth.

These fluid textures, especially sought after for oily skins and in hot countries, are nevertheless more difficult to stabilize, especially when they contain a high proportion of water and of alcohols (for the fresh effect), combined with the presence of fillers and pigments (for the coverage effect and the colour effect). This is even truer for W/O emulsions, which are standard in the field of foundations.

Furthermore, these fresh formulas are advantageously lightly filled, in the sense of containing little filler; however it is important that these formulas give coverage in order to mask defects (dyschromia, marks and unevenness of the skin). This is particularly true in Asia, in Japan where, while having to be fresh, light and fine, the textures must provide coverage. It is therefore important to provide in these formulas materials that can, without destabilizing and without thickening these textures, provide coverage and also luminosity.

Moreover, consumers are also in search of novel cosmetic products for improving the appearance of keratin materials and especially the skin, in particular the surface appearance (visible and/or tactile unevenness) and/or the skin complexion, an external sign of a healthy glow, health and youth.

During the ageing process for example, the structure of the skin and its cutaneous functions change: the principal clinical signs of skin ageing are in particular the appearance of fine lines and deep wrinkles, which increase with age. A disorganization of the "grain" of the skin is also observed, that is to say that the microrelief is less even and exhibits an anisotropic character.

It is known practice to treat these signs of ageing using cosmetic or dermatological compositions containing active agents capable of combating ageing. These active agents act on wrinkles by eliminating dead skin cells and by accelerating the cell renewal process. However, these active agents have the drawback of only being effective for the treatment of wrinkles after a certain application time. However, it is increasingly sought to obtain an immediate effect of the active agents used.

Other known methods for camouflaging skin defects use compositions containing fillers known as "soft-focus" fillers as described in application EP-A-1 099 437, which, via an optical effect, reduce skin defects such as marks, wrinkles and fine lines.

However, the results obtained with these compositions are often insufficient to effectively reduce or even mask the most pronounced wrinkles. Moreover, the soft-focus effect is often impaired by the presence of opaque fillers, or pigments, in the compositions.

Furthermore, the solid particles such as fillers and pulverulent colorants present in the skin makeup compositions have the drawback of concentrating in the wrinkles, in particular deep wrinkles, thus accentuating the unevenness of the skin. The application of these compositions to particularly wrinkled skins (especially mature skins) result in a makeup effect that marks or reveals the wrinkles.

The inventors have furthermore studied the impact of visible light on the skin: 5% of the radiation is directly reflected, reflecting the entire colour spectrum of the light: this is the surface radiance, whereas 95% penetrates into the skin, interacting with the epidermis and the dermis, and 40% is rediffused at the surface: this is the light inside the skin.

But when the skin quality is impaired (fatigue, dryness, ageing, etc.):
  the surface radiance is minimized since the light is reflected less well over an uneven relief,
  the internal light loses the intensity of its radiation since it is absorbed more, especially by melanin, in its blue components.

The use of fillers for imparting coverage and of pigments (including $TiO_2$) which, for the latter, provide colour in addition to coverage, is known from the prior art. They make it possible to adjust the visual "coverage" of the skin by the application of a composition (e.g.: foundation) containing said fillers/pigments and thus give consumers the possibility:
  of unifying the colour of the complexion, or even of enhancing it when the woman (man) judges that her (his) natural skin tone is not in keeping with the image that she (he) would like to give herself (himself), the climate, the season, etc.; and/or of correcting the defects that have bothered them for a long time or that occur with advancing age and that she (he) wishes to reduce or hide.

Unfortunately, these raw materials may mark the face by highlighting the relief and the microrelief of the face. This is an even greater shame since age is a factor in accentuating this microrelief and it is not acceptable, for these consumers, to accentuate the latter with the same foundation that they use to cover and colour their face.

Furthermore, these same raw materials also have the advantage of providing mattness to the face, but by doing so may give the complexion a dull appearance.

Therefore there remains the need to find novel care and/or makeup products, especially for the complexion, which give a luminous effect, without being shiny, which do not mark the relief while covering the defects (dyschromia, marks) or which give a unified colour to the face, in particular a natural and unified colour to the face, advantageously a healthy glow effect.

According to one alternative, or additionally, novel products are sought in particular that have a fluid, fresh and fine texture combined with a care and/or makeup result that is fine, non-powdery, non-marking but nevertheless gives coverage and is luminous.

According to one alternative, or additionally, novel products are sought that make it possible to obtain a satisfactory camouflaging of skin defects, while retaining a natural and luminous appearance of the complexion, without being shiny.

The inventors have demonstrated that the use of a dispersion (otherwise known as a pre-dispersion) of bismuth oxychloride in an ester or an oil whose solubility parameter at 25° C., δa, is greater than 6 $(J/cm^3)^{1/2}$, in particular a dispersion (pre-dispersion) of bismuth oxychloride in 2-ethylhexyl hydroxystearate (INCI name: ethylhexyl hydroxystearate), to date known in anhydrous varnish, gloss and eyeshadow compositions for its shiny effect, made it possible, by formulating in an emulsion intended for application to the skin, to impart luminosity to the skin; the complexion thus regains the freshness and radiance of youth.

Compared to the use of nacres or pigments of titanium dioxide type conventionally used in the search for a covering and luminous effect, the effect obtained with the dispersion of bismuth oxychloride used according to the invention is advantageously homogeneous, and has no sparkling spots.

The inventors have furthermore demonstrated that the use of a dispersion (pre-dispersion) of bismuth oxychloride in an ester or an oil whose solubility parameter at 25° C., δa, is greater than 6 $(J/cm^3)^{1/2}$, in particular a dispersion (pre-dispersion) of bismuth oxychloride in 2-ethylhexyl hydroxystearate (INCI name: ethylhexyl hydroxystearate), made it possible, by formulating in an emulsion intended for application to the skin and that contains a high proportion of water and of alcohols, to impart luminosity to the skin and a fresh effect; the complexion thus regains the freshness and radiance of youth.

The inventors have also demonstrated that the use of a dispersion (pre-dispersion) of bismuth oxychloride in an ester or an oil whose solubility parameter at 25° C., δa, is greater than 6 $(J/cm^3)^{1/2}$, in particular a dispersion (pre-dispersion) of bismuth oxychloride in 2-ethylhexyl hydroxystearate (INCI name: ethylhexyl hydroxystearate), made it possible, by formulating with a soft-focus agent in a composition intended for application to the skin, to mask skin defects by imparting luminosity to the skin; the complexion thus regains the freshness and radiance of youth.

And they have demonstrated that the use of the combination of a pre-dispersion of bismuth oxychloride in an ester or an oil whose solubility parameter at 25° C., δa, is greater than 6 $(J/cm^3)^{1/2}$, in particular a pre-dispersion of bismuth oxychloride in 2-ethylhexyl hydroxystearate (INCI name: ethylhexyl hydroxystearate), with a particular colorant (especially a composite pigment as defined below), in a composition intended for application to the skin, made it possible to impart light to the skin and to improve its surface radiance, advantageously with a healthy glow effect: the complexion is fresher, more luminous and more radiant.

The use of bismuth oxychloride (CI 77163) in powder or agglomerate form was known in foundations as a filler intended to provide a certain sensoriality (soft feel). This compound was also able to provide a satiny, localized and discontinuous effect, which, in products such as fluids, compacts or even powders, may be perceived as a nacreous sheen and not the desired luminous look.

Application WO 2004/041234 furthermore describes lightening and whitening anhydrous compositions comprising a *Phyllanthus emblica* (PE) extract and, as additive, bismuth oxychloride in the form of a powder or a dispersion in order to give the composition a dry and soft feel on the skin.

The dispersion form (Biron® Liquid Silver) is described in this application, and is sold by the supplier Merck, as a raw material that is highly lustrous and shiny, which are not properties that are desired for an application to facial skin, and especially for the complexion. When it is observed in the pure state, it is a very silvery and extremely shiny liquid, highly recommended by the supplier for uses in compositions of the gloss, varnish and eyeshadow type, but a priori unsuitable for the expectations of a complexion makeup result.

Its use in rinse-off cleansing compositions is also known from U.S. Pat. No. 6,906,015.

However, we have demonstrated that the use of this dispersion (pre-dispersion) of bismuth oxychloride in 2-ethylhexyl hydroxystearate was able to give care and/or makeup products, especially for the complexion, in particular of emulsion type, the ability to provide, after application/making up:
a) coverage,
b) and especially luminosity.

The invention therefore relates to a cosmetic composition in the form of an emulsion for topical application to keratin materials, in particular the skin, comprising, in a physiologically acceptable medium:
(i) at least one dispersion of bismuth oxychloride (CI 77163) in an oily dispersant (an oil) chosen from a) monoesters of formula $R_1COOR_2$ in which $R_1$ represents a linear or branched hydrocarbon-based chain comprising from 4 to 40 carbon atoms, preferably from 4 to 30 carbon atoms, and preferentially from 7 to 20 carbon atoms, and $R_2$ represents a branched hydrocarbon-based chain containing from 3 to 40 carbon atoms, preferably from 10 to 30 carbon atoms, and preferentially from 16 to 26 carbon atoms; b) polar oils whose solubility parameter at 25° C., δa, is greater than 6 $(J/cm^3)^{1/2}$, and mixtures thereof, and
(ii) at least one oil chosen from hydrocarbon-based oils having a refractive index greater than 1.42 and a solubility parameter at 25° C., δa, greater than 1 $(J/cm^3)^{1/2}$, phenyl silicone oils, and mixtures thereof.

The invention also relates to a process for preparing an emulsion according to the invention, characterized in that:
a) introduced into the fatty phase is a dispersion (pre-dispersion) of bismuth oxychloride comprising 68% to 72% by weight of bismuth oxychloride in 28% to 32% by weight of 2-ethylhexyl hydroxystearate, relative to the total weight of the dispersion,
b) the aqueous phase is prepared separately,
c) the emulsion is produced with (vigorous) stirring and at room temperature, in particular by using a Rayneri mixer fitted with a deflocculator.

The invention also relates to a cosmetic method for caring for and/or making up keratin materials, comprising the application to said keratin materials, in particular to the skin, of a composition according to the invention, for example in the form of a coat of composition or several layers of composition applied to facial skin, used alone or in combination with another composition (two-step application), said composition according to the invention being applied before and/or after the application of a care composition or of a makeup composition such as a foundation.

In particular, the application of said composition to the skin, especially facial skin, provides the latter with a luminous effect and coverage.

The invention also targets the use of a dispersion (pre-dispersion) of bismuth oxychloride in an oily dispersant as defined according to the invention, in a cosmetic composition in the form of an emulsion, as an agent for imparting a luminosity to the complexion.

According to another particular embodiment, the composition according to the invention comprises at least one aqueous phase forming from 30% to 70% by weight relative to the total weight of the composition, and at least 5% by weight, relative to the total weight of the composition, of at least one $C_2$-$C_8$ monoalcohol.

According to another particular embodiment, the composition according to the invention comprises at least one soft-focus agent as defined below.

According to one particular embodiment, the composition according to the invention comprises at least one colorant chosen from goniochromatic colouring agents, photochromic colouring agents, fluorescent agents, optical brighteners, lakes, organic pigments, composite pigments, and mixtures thereof.

The invention therefore also relates to a cosmetic composition in the form of an emulsion for topical application to keratin materials, in particular the skin, comprising, in a physiologically acceptable medium:
(i) an aqueous phase forming 30% to 70% by weight relative to the total weight of said composition,
(ii) at least 5% by weight relative to the total weight of the composition of at least one $C_2$ to $C_8$ monoalcohol, and
(iii) at least one dispersion (pre-dispersion) of bismuth oxychloride (CI 77163) in an oily dispersant (an oil) chosen from a) monoesters of formula $R_1COOR_2$ in which $R_1$ represents a linear or branched hydrocarbon-based chain comprising from 4 to 40 carbon atoms, preferably from 4 to 30 carbon atoms, and preferentially from 7 to 20 carbon atoms, and $R_2$ represents a branched hydrocarbon-based chain containing from 3 to 40 carbon atoms, preferably from 10 to 30 carbon atoms, and preferentially from 16 to 26 carbon atoms; b) polar oils whose solubility parameter at 25° C., δa, is greater than 6 $(J/cm^3)^{1/2}$, and mixtures thereof.

Advantageously according to this embodiment, the composition also comprises at least one oil chosen from hydrocarbon-based oils having a refractive index greater than 1.42 and a solubility parameter at 25° C., δa, greater than 1 $(J/cm^3)^{1/2}$, phenyl silicone oils, and mixtures thereof.

The invention also relates to a process for preparing an emulsion according to the invention, characterized in that:

a) introduced into the fatty phase is a dispersion of bismuth oxychloride comprising 68% to 72% by weight of bismuth oxychloride in 28% to 32% by weight of 2-ethylhexyl hydroxystearate, relative to the total weight of the dispersion,
b) the aqueous phase is prepared separately,
c) the emulsion is produced with (vigorous) stirring and at room temperature, in particular by using a Rayneri mixer fitted with a deflocculator, and
d) the $C_2$-$C_8$ monoalcohol is incorporated with (moderate) stirring.

The invention also relates to a cosmetic method for caring for and/or making up keratin materials, comprising the application to said keratin materials, in particular to the skin, of a composition according to the invention, for example in the form of a coat of composition or several coats of composition applied to facial skin, used alone or in combination with another composition (two-step application), said composition according to the invention being applied before and/or after the application of a care composition or of a makeup composition such as a foundation.

In particular, the application of said composition to the skin, especially facial skin, provides the latter with a luminous effect, good coverage and a fresh effect.

The invention also targets the use of a dispersion (pre-dispersion) of bismuth oxychloride in an oily dispersant as defined according to the invention, in a cosmetic composition according to the invention, as an agent for imparting a luminosity to the complexion.

The invention also relates to a cosmetic composition for topical application to keratin materials, in particular the skin, comprising, in a physiologically acceptable medium:
(i) at least one dispersion of bismuth oxychloride (CI 77163) in an oily dispersant (an oil) chosen from a) monoesters of formula $R_1COOR_2$ in which $R_1$ represents a linear or branched hydrocarbon-based chain comprising from 4 to 40 carbon atoms, preferably from 4 to 30 carbon atoms, and preferentially from 7 to 20 carbon atoms, and $R_2$ represents a branched hydrocarbon-based chain containing from 3 to 40 carbon atoms, preferably from 10 to 30 carbon atoms, and preferentially from 16 to 26 carbon atoms; b) polar oils whose solubility parameter at 25° C., δa, is greater than 6 $(J/cm^3)^{1/2}$, and mixtures thereof, and
(ii) at least one soft-focus agent.

Advantageously according to this embodiment, the composition also comprises at least one oil chosen from hydrocarbon-based oils having a refractive index greater than 1.42 and a solubility parameter at 25° C., δa, greater than 1 $(J/cm^3)^{1/2}$, phenyl silicone oils, and mixtures thereof.

The invention also relates to a cosmetic method for caring for and/or making up keratin materials, comprising the application to said keratin materials, in particular to the skin, of a composition according to the invention, for example in the form of a coat of composition or several coats of composition applied to facial skin, used alone or in combination with another composition (two-step application), said composition according to the invention being applied before and/or after the application of a care composition or of a makeup composition such as a foundation.

In particular, the application of said composition to the skin, especially facial skin, provides the latter with a luminous effect and coverage.

Another subject of the invention is a cosmetic composition for caring for and/or making up keratin materials, in particular the skin, comprising, in a physiologically acceptable medium:

(i) at least one colorant chosen from goniochromatic colouring agents, photochromic colouring agents, fluorescent agents, optical brighteners, lakes, organic pigments, composite pigments, and mixtures thereof; and (ii) at least bismuth oxychloride dispersed in at least one oil chosen from a) monoesters of formula $R_1COOR_2$ in which $R_1$ represents a linear or branched hydrocarbon-based chain comprising from 4 to 40 carbon atoms, preferably from 4 to 30 carbon atoms, and preferentially from 7 to 20 carbon atoms, and $R_2$ represents a branched hydrocarbon-based chain containing from 3 to 40 carbon atoms, preferably from 10 to 30 carbon atoms, and preferentially from 16 to 26 carbon atoms; b) polar oils whose solubility parameter at 25° C., δa, is greater than 6 $(J/cm^3)^{1/2}$, and mixtures thereof.

Advantageously according to this embodiment, the composition also comprises at least one oil chosen from hydrocarbon-based oils having a refractive index greater than 1.42 and a solubility parameter at 25° C., δa, greater than 1 $(J/cm^3)^{1/2}$, phenyl silicone oils, and mixtures thereof.

According to one particular embodiment, said colorant is chosen from fluorescent agents, optical brighteners, lakes, organic pigments, composite pigments, and mixtures thereof. Preferably, said colorant is chosen from composite pigments as described below.

Preferably, said colorant is present in the composition in a content ranging from 0.001% to 3% by weight relative to the total weight of said composition, in particular from 0.05% to 2% by weight relative to the total weight of said composition.

According to one preferred embodiment, the bismuth oxychloride is dispersed in at least one oil chosen from castor oil and 2-ethylhexyl hydroxystearate, more preferably 2-ethylhexyl hydroxystearate.

According to one particular and preferred embodiment, the composition according to the invention is in the form of a water-in-oil emulsion.

According to one particular embodiment, the composition according to the invention is a facial makeup composition, in particular a foundation or a complexion illuminator.

The invention also relates to a process for preparing a cosmetic composition for caring for and/or making up keratin materials, in particular the skin, comprising the addition, to a physiologically acceptable medium comprising (i) at least one colorant chosen from goniochromatic colouring agents, photochromic colouring agents, fluorescent agents, optical brighteners, lakes, organic pigments, composite pigments, and mixtures thereof, (ii) at least one bismuth oxychloride in the form of a pre-dispersion in an oil chosen from a) monoesters of formula $R_1COOR_2$ in which $R_1$ represents a linear or branched hydrocarbon-based chain comprising from 4 to 40 carbon atoms, preferably from 4 to 30 carbon atoms, and preferentially from 7 to 20 carbon atoms, and $R_2$ represents a branched hydrocarbon-based chain containing from 3 to 40 carbon atoms, preferably from 10 to 30 carbon atoms, and preferentially from 16 to 26 carbon atoms; b) polar oils whose solubility parameter at 25° C., δa, is greater than 6 $(J/cm^3)^{1/2}$, and mixtures thereof.

According to one particular embodiment, said composition according to the invention also contains at least one additional ingredient chosen from a filler, an additional colorant and/or reflective material, and mixtures thereof.

The invention also relates to a cosmetic method for caring for and/or making up keratin materials, comprising the application to said keratin materials, in particular to the skin, of a composition according to the invention. In particular, the application of said composition to the skin, especially facial skin, provides the latter with a luminous effect and a radiance of the skin with advantageously a healthy glow effect.

The application to keratin materials and facial skin in particular may be carried out for example in the form of a coat of composition or several coats of composition applied to facial skin, used alone or in combination with another composition (two-step application), said composition according to the invention being applied before and/or after the application of a care composition or of a makeup composition such as a foundation.

In particular, the application of said composition to the skin, especially facial skin, provides the latter with a luminous effect and radiance and advantageously a healthy glow effect.

The invention also relates to the cosmetic use of the combination (i) of at least one colorant chosen from goniochromatic colouring agents, photochromic colouring agents, fluorescent agents, optical brighteners, lakes, organic pigments, composite pigments, and mixtures thereof and (ii) of at least bismuth oxychloride dispersed in at least one oil chosen from a) monoesters of formula $R_1COOR_2$ in which $R_1$ represents a linear or branched hydrocarbon-based chain comprising from 4 to 40 carbon atoms, preferably from 4 to 30 carbon atoms, and preferentially from 7 to 20 carbon atoms, and $R_2$ represents a branched hydrocarbon-based chain containing from 3 to 40 carbon atoms, preferably from 10 to 30 carbon atoms, and preferentially from 16 to 26 carbon atoms; b) polar oils whose solubility parameter at 25° C., δa, is greater than 6 $(J/cm^3)^{1/2}$, and mixtures thereof, for imparting a luminous effect to the skin and providing radiance.

In particular, the bismuth oxychloride (ii) is in the form of a pre-dispersion in at least one oil as defined above.

Lastly, the invention relates to the combination comprising (i) at least one titanium oxide/Blue No. 1 Aluminium lake first composite pigment and one titanium oxide/Red No. 28 Aluminium lake and D&C Red No. 7 second composite pigment and (ii) at least bismuth oxychloride dispersed in at least 2-ethylhexyl hydroxystearate, able to be used in a cosmetic preparation process or a cosmetic composition or a cosmetic treatment method such as are defined in any one of the claims.

In particular, the bismuth oxychloride (ii) is in the form of a pre-dispersion in at least one oil as defined above.

Dispersion of Bismuth Oxychloride

The bismuth oxychloride used for the preparation of a composition according to the invention is dispersed in at least one oil as defined below (liquid mixture) and differs from conventional bismuth oxychloride in powder form.

Reference will thus be made to a 'dispersion' or 'pre-dispersion' of bismuth oxychloride in an oil in order to define, according to the invention, the raw material used in a process for preparing a cosmetic composition according to the invention.

Reference will be made to bismuth oxychloride 'dispersed in at least one oil' as defined according to the invention or 'mixture of bismuth oxychloride with said oil', in order to define the raw material once formulated into the composition of the invention.

The dispersion (otherwise known as a pre-dispersion) of bismuth oxychloride in an oily dispersant that is used according to the invention comprises at least bismuth oxychloride (CI 77163) dispersed in an oil chosen from:

a) monoesters of formula $R_1COOR_2$ in which $R_1$ represents a linear or branched hydrocarbon-based chain comprising from 4 to 40 carbon atoms, preferably from 4 to 30 carbon atoms, and preferentially from 7 to 20 carbon atoms, and $R_2$ represents a branched hydrocarbon-based chain containing from 3 to 40 carbon atoms, preferably from 10 to 30 carbon atoms, and preferentially from 16 to 26 carbon atoms; and b) polar oils whose solubility parameter at 25° C., δa, is greater than 6 $(J/cm^3)^{1/2}$.

The composition according to the invention thus comprises at least bismuth oxychloride and at least one oil (oily dispersant) chosen from:

a) monoesters of formula $R_1COOR_2$ in which $R_1$ represents a linear or branched hydrocarbon-based chain comprising from 4 to 40 carbon atoms, preferably from 4 to 30 carbon atoms, and preferentially from 7 to 20 carbon atoms, and $R_2$ represents a branched hydrocarbon-based chain containing from 3 to 40 carbon atoms, preferably from 10 to 30 carbon atoms, and preferentially from 16 to 26 carbon atoms; and b) polar oils whose solubility parameter at 25° C., δa, is greater than 6 $(J/cm^3)^{1/2}$.

a) Monoesters

As esters (or ester oils) used as a dispersant of bismuth oxychloride, mention may especially be made of monoesters of formula $R_1COOR_2$ in which $R_1$ represents a linear or branched hydrocarbon-based chain comprising from 4 to 40 carbon atoms, preferably from 4 to 30 carbon atoms, and preferentially from 7 to 20 carbon atoms, and $R_2$ represents a branched hydrocarbon-based chain containing from 3 to 40 carbon atoms, preferably from 10 to 30 carbon atoms, and preferentially from 16 to 26 carbon atoms.

According to one particular embodiment, the dispersion of bismuth oxychloride comprises a monoester chosen from isodecyl neopentanoate; isocetyl octanoate; isononyl isononanoate, isodecyl isononanoate, tridecyl isononanoate; hexyl laurate, 2-hexyldecyl laurate; isopropyl myristate, isocetyl myristate, isotridecyl myristate, 2-octyldodecyl myristate; isopropyl palmitate, 2-ethylhexyl palmitate, isooctyl palmitate, isocetyl palmitate, isodecyl palmitate, isostearyl palmitate, 2-octyldecyl palmitate; isopropyl isostearate, 2-ethylhexyl hydroxystearate, 2-octyldodecyl stearate, isostearyl isostearate; 2-octyldodecyl erucate; and mixtures thereof.

More preferably, use will be made of an ester oil chosen from isodecyl neopentanoate; isocetyl octanoate; isononyl isononanoate; isopropyl isostearate, 2-ethylhexyl hydroxystearate, 2-octyldodecyl stearate, isostearyl isostearate; and mixtures thereof.

Preferably, the dispersion of bismuth oxychloride comprises 2-ethylhexyl hydroxystearate.

b) Polar Oils

According to another embodiment, the bismuth oxychloride is dispersed in a highly polar oil, otherwise known as a polar oil whose solubility parameter at 25° C., δa, is greater than 6 $(J/cm^3)^{1/2}$.

For the purposes of the present invention, the term "polar oil" means an oil whose solubility parameter at 25° C., δa, is other than 0 $(J/cm^3)^{1/2}$.

The definition and calculation of the solubility parameters in the Hansen three-dimensional solubility space are described in the article by C. M. Hansen: "The three dimensional solubility parameters". J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

As examples of polar oils whose solubility parameter at 25° C., δa, is greater than 6 $(J/cm^3)^{1/2}$, mention may especially be made of the following oils:

esters, such as triisodecyl trimellitate, dioctyl (2-ethylhexyl) carbonate, caprylyl carbonate (Cetiol CC), polyglyceryl-10 nonaisostearate, triisoarachidyl citrate, oxypropylenated (3 OP) myristyl diadipate, diethylhexyl adipate, propylene glycol dipelargonate, neopentyl glycol dicaprate, dipentaerythrityl hexacaprylate/hexacaprate, triisostearyl citrate, tri(2-ethylhexyl) trimellitate, glyceryl triisononanoate, 2-octyldodecyl hydroxystearate, dicaprylyl maleate, propylene glycol dioctanoate, caprylic/capric triglyceride, polyglyceryl-2 triisostearate, pentaerythrityl tetra(2-ethylhexanoate), triisocetyl citrate, diethylene glycol diisononanoate, glyceryl trioctanoate, tricaprylin, diisostearyl malate, glyceryl triheptanoate, dipropylene glycol dibenzoate, octyl hydroxystearate, 2-ethylhexyl palmitate glyceryl ether, propylene glycol monoisostearate, isostearyl lactate, polyglyceryl-2 diisostearate, oxyethylenated (7 OE) glyceryl triacetate, C12-13 alkyl lactate, polyglyceryl-3 diisostearate, glyceryl triacetate and polyglyceryl-2 isostearate;

plant oils such as castor oil;

oils comprising PEG or POE groups such as PPG-10 butanediol, PEG (8 OE), PEG (6OE), PEG (4 OE).

According to one preferred embodiment, use will be made, as polar oil with $\delta_a > 6$, of octyl hydroxystearate or 2-ethylhexyl hydroxystearate.

According to another particular embodiment, use will be made, as polar oil with $\delta_a > 6$, of castor oil.

According to one particular and preferred embodiment, the composition according to the invention thus comprises, in a physiologically acceptable medium:

a. at least one aqueous phase forming from 30% to 70% by weight relative to the total weight of said composition, and at least 5% by weight, relative to the total weight of the composition, of at least one $C_2$-$C_8$ monoalcohol; and b. at least bismuth oxychloride dispersed in at least one oil chosen from 2-ethylhexyl hydroxystearate, or castor oil, preferably 2-ethylhexyl hydroxystearate, c. and advantageously at least one oil chosen from hydrocarbon-based oils having a refractive index greater than 1.42 and a solubility parameter at 25° C., δa, greater than 1 (J/cm3)½, silicone oils, in particular phenyl silicone oils, and mixtures thereof.

According to one particular and preferred embodiment, the composition according to the invention thus comprises, in a physiologically acceptable medium:

a. at least one soft-focus agent; and b. at least bismuth oxychloride dispersed in at least one oil chosen from 2-ethylhexyl hydroxystearate, or castor oil, preferably 2-ethylhexyl hydroxystearate, c. and advantageously at least one oil chosen from hydrocarbon-based oils having a refractive index greater than 1.42 and a solubility parameter at 25° C., δa, greater than 1 (J/cm3)½, silicone oils, in particular phenyl silicone oils, and mixtures thereof.

According to one particular and preferred embodiment, the composition according to the invention thus comprises, in a physiologically acceptable medium:
a. at least one colorant chosen from goniochromatic colouring agents, photochromic colouring agents, fluorescent agents, optical brighteners, lakes, organic pigments, composite pigments, or at least one soft-focus agent, and mixtures thereof; and
b. at least bismuth oxychloride dispersed in at least one oil chosen from 2-ethylhexyl hydroxystearate, or castor oil, preferably 2-ethylhexyl hydroxystearate,
c. and advantageously at least one oil chosen from hydrocarbon-based oils having a refractive index greater than 1.42 and a solubility parameter at 25° C., δa, greater than 1 (J/cm3)½, silicone oils, in particular phenyl silicone oils, and mixtures thereof.

The bismuth oxychloride will generally be present in the dispersion (pre-dispersion) in the presence of the oily dispersant (oil), in a content by weight ranging from 50% to 90%, especially from 60% to 80%, and better still from 65% to 75% by weight relative to the total weight of the dispersion. The oily dispersant will consequently be present in the dispersion in a content ranging from 10% to 50% by weight, in particular from 20% to 40% by weight, and better still from 25% to 35% by weight.

According to one particular embodiment, use is made of a dispersion (pre-dispersion) comprising bismuth oxychloride and an oily dispersant in a weight ratio ranging from 2 to 3.

According to one preferred embodiment, use is made of a dispersion (pre-dispersion) comprising 68% to 72% by weight of bismuth oxychloride in 28% to 32% by weight of 2-ethylhexyl hydroxystearate, relative to the total weight of the dispersion, i.e. a bismuth oxychloride/oily dispersant weight ratio of greater than or equal to 2, preferably of between 2 and 2.6.

Such a dispersion (pre-dispersion) is especially sold under the name Biron® Liquid Silver by the company MERCK.

The dispersion (pre-dispersion) of bismuth oxychloride will be used in a content of raw material ranging from 0.05% to 30% by weight, preferably from 0.2% to 25%, more preferably from 0.5% to 20% and better still from 1% to 15% by weight relative to the total weight of said composition according to the invention.

A composition according to the invention could thus comprise bismuth oxychloride in a content of raw material ranging from 0.035% to 21% by weight, preferably from 0.14% to 17.5% by weight, more preferably from 0.35% to 14% by weight, and better still from 0.7% to 10.5% by weight of active material relative to the total weight of said composition with a bismuth oxychloride/ethylhexyl hydroxystearate weight ratio ranging from 2 to 3, preferably from 2 to 2.6.

According to one particular embodiment, the dispersion (pre-dispersion) of bismuth oxychloride will be used in a content of raw material ranging from 0.01% to 15% by weight, preferably from 0.5% to 10% by weight relative to the total weight of said composition according to the invention.

In other words, the total content of bismuth oxychloride and of associated oil, as defined previously (oily dispersant), will range from 0.01% to 15% by weight, preferably from 0.5% to 10% by weight relative to the total weight of said composition according to the invention, in particular with a bismuth oxychloride/oily dispersant (associated oil) weight ratio ranging from 2 to 3.

According to one particular embodiment, these values do not take into account the contents of the optional additional oils present in the final composition.

The raw material content of the dispersion (pre-dispersion) of bismuth oxychloride will be able to be adjusted by a person skilled in the art according to whether or not the composition also contains colorants.

By way of example, when the composition according to the invention is not coloured and is for example used as a care and/or makeup base, the raw material content of the dispersion (pre-dispersion) of bismuth oxychloride will generally range from 0.01% to 30%, especially from 0.1% to 30%, in particular from 1% to 30%, preferably from 2% to 20%, better still from 5% to 15% by weight of raw material relative to the total weight of said composition according to the invention.

According to one preferred embodiment, when the composition according to the invention is not coloured the raw material content of the dispersion (pre-dispersion) of bismuth oxychloride, in other words the total content of bismuth oxychloride and of associated oil as defined previously, will generally range from 0.01% to 15%, preferably from 0.1% to 10% by weight relative to the total weight of said composition according to the invention, in particular with a bismuth oxychloride/oily dispersant (associated oil) weight ratio ranging from 2 to 3.

And when the composition according to the invention is coloured, that is to say that it also comprises colorants (pigments, nacres, dyes), the raw material content of the dispersion (pre-dispersion) of bismuth oxychloride will generally range from 0.01% to 20%, especially from 0.05% to 20%, preferably from 0.2% to 15%, better still from 0.5% to 10% by weight of raw material relative to the total weight of said composition according to the invention.

According to one particular embodiment, when the composition according to the invention is coloured, that is to say that it also comprises colorants (pigments, nacres, dyes) for example in a content ranging from 0.01% to 8% by weight relative to the total weight of said composition, the raw material content of the dispersion (pre-dispersion) of bismuth oxychloride, in other words the total content of bismuth oxychloride and of associated oil as defined previously, will generally range from 0.05% to 12%, preferably from 1% to 11% by weight of raw material relative to the total weight of said composition according to the invention. For a larger content of additional colorants, for example ranging from 8% to 25% by weight relative to the total weight of said composition, the raw material content of the dispersion (pre-dispersion) of bismuth oxychloride, in other words the total content of bismuth oxychloride and of associated oil as defined previously, will generally range from 1.2% to 15% by weight, preferably from 1.5% to 12% by weight relative to the total weight of said composition.

According to one particular embodiment, these values do not take into account the contents of the optional additional oils present in the final composition.

Oil Having a Refractive Index>1.42

The composition according to the invention also comprises at least one specific oil, characterized by a refractive index greater than 1.42, especially greater than 1.43, preferably greater than 1.45 and more preferably greater than 1.46.

Such an oil gives the composition according to the invention a luminosity or radiance effect after application to the skin.

The term "oil" means any fatty substance that is in liquid form at room temperature (20-25° C.) and at atmospheric pressure.

The oil having a refractive index greater than 1.42 may be chosen from polar hydrocarbon-based oils ($\delta_a$>1), silicone oils, advantageously phenyl silicone oils, and mixtures thereof.

Polar Hydrocarbon-Based Oils ($\delta_a$>1) Having a Refractive Index>1.42

Mention may especially be made of the following oils:
ethers, such as dicaprylyl ether and 2-ethylhexyl glyceryl ether palmitate;
oils comprising PEG or POE groups such as oxypropylenated (3 OP) myristyl diadipate, oxyethylenated (7 OE) glyceryl triacetate, PEG (4 OE), PEG (6 OE), octyldodecyl PPG-3 myristyl ether dimer dilinoleate and PEG (8 OE);
esters such as:
linear fatty acid esters with a total carbon number ranging from 35 to 70, for instance pentaerythrityl tetrapelargonate (MW=697 g/mol);
hydroxylated esters such as for example polyglyceryl-2 triisostearate (MW=965 g/mol), triisocetyl citrate (MW=864 g/mol), diisostearyl malate (MW=639 g/mol);
aromatic esters such as for example tridecyl trimellitate (MW=757 g/mol);
$C_{24}$-$C_{28}$ branched fatty alcohol or fatty acid esters such as those described in patent application EP-A-0 955 039, and especially triisoarachidyl citrate (MW=1033.76 g/mol), pentaerythrityl tetraisononanoate (MW=697 g/mol), glyceryl triisostearate (MM=891 g/mol), glyceryl tris(2-decyl)tetradecanoate (MW=1143 g/mol), pentaerythrityl tetraisostearate (MW=1202 g/mol), polyglyceryl-2 tetraisostearate (MW=1232 g/mol) or pentaerythrityl tetrakis(2-decyl)tetradecanoate (MW=1538 g/mol);
a polyester resulting from the esterification of at least one triglyceride of hydroxylated carboxylic acid(s) with an aliphatic monocarboxylic acid and with an aliphatic dicarboxylic acid, which is optionally unsaturated, for instance the succinic acid and isostearic acid castor oil sold under the reference Zenigloss by Zenitech;
esters of a diol dimer and of a diacid dimer of general formula HO—$R^1$—(—OCO—$R^2$—COO—$R^1$—)$_h$—OH, in which:
$R^1$ represents a diol dimer residue obtained by hydrogenation of dilinoleic diacid,
$R^2$ represents a hydrogenated dilinoleic diacid residue, and h represents an integer ranging from 1 to 9,
especially the esters of dilinoleic diacids and of dilinoleyl diol dimers sold by the company Nippon Fine Chemical under the trade names Lusplan DD-DA5® and DD-DA7®;
oils of plant origin such as for example sesame seed oil (MW=820 g/mol), arara oil, jojoba oil, pracaxi oil, virgin olive oil, *Limnanthes* (meadowfoam) oil, sesame seed oil, *Ximenia* oil, soybean oil, macadamia oil, castor oil;
vinylpyrrolidone copolymers such as the vinylpyrrolidone/1-hexadecene copolymer, Antaron V-216 sold or manufactured by the company ISP (MW=7300 g/mol);
and mixtures thereof.

As an oil having a refractive index>1.42, mention may especially be made of isodecyl neopentanoate.

As oils having a refractive index>1.43, mention may especially be made of:

dicaprylyl ether;
esters such as glyceryl triacetate, 2-ethylhexyl 2-ethylhexanoate, isopropyl myristate, propylene glycol dioctanoate, caprylyl carbonate (Cetiol CC), dioctyl (2-ethylhexyl) carbonate, isononyl isononanoate, isopropyl palmitate, isopropyl stearate, isodecyl isononanoate and neopentyl glycol dicaprate;
and mixtures thereof.

As oils having a refractive index>1.44, mention may especially be made of:
esters such as propylene glycol dipelargonate, isopropyl isostearate, octyldodecyl neopentanoate, diethylene glycol diisononanoate, butyl stearate, C12-13 alkyl lactate, glyceryl triheptanoate, isostearyl neopentanoate, cetyl 2-ethylhexanoate, glyceryl trioctanoate, tridecyl isononanoate, diethylhexyl adipate, 2-ethylhexyl palmitate, tricaprylin, caprylic/capric triglyceride, dicaprylyl maleate, isostearyl isononanoate, glyceryl triisononanoate and pentaerythrityl tetra(2-ethylhexanoate);
and mixtures thereof.

As oils having a refractive index>1.45, mention may especially be made of:
2-ethylhexyl glyceryl ether palmitate;
esters such as isostearyl lactate, isostearyl palmitate, octyldodecyl neodecanoate, isocetyl stearate, propylene glycol monoisostearate, 2-ethylhexyl isostearate, octyldodecyl stearate, octyldodecyl myristate, diisostearyl adipate, octyl hydroxystearate, glyceryl triisostearate, octyldodecyl stearoyl stearate, diisocetyl dodecanedioate, dipentaerythrityl hexacaprylate/hexacaprate, 2-octyldodecyl hydroxystearate, pentaerythrityl tetraoctyldodecanoate, triisostearyl citrate, pentaerythrityl tetra(2-hexyldecanoate) and propylene glycol diisostearate;
oxypropylenated (3 OP) myristyl diadipate, oxyethylenated (7 OE) glyceryl triacetate and PEG (4 OE);
and mixtures thereof.

As oils having a refractive index>1.46, mention may especially be made of:
esters such as tridecyltetradecanoin, isostearyl isostearate, isofol-24 isostearate, triisocetyl citrate, diisopropyl dimer dilinoleate, pentaerythrityl tetradecyltetradecanoate, diisostearyl malate, diisoarachidyl dodecanedioate, octyldodecyl erucate, triisoarachidyl citrate, polyglyceryl-2 tetraisostearate, polyglyceryl-2 triisostearate, polyglyceryl-2 diisostearate, hexyldecyl myristoyl methylaminopropionate, pentaerythrityl tetraisostearate, trimethylolpropane triisostearate, oleyl erucate, ditrimethylolpropane tetraisostearate, polyglyceryl-2 isostearate, dioctyldodecyl dimer dilinoleate, polyglyceryl-10 nonaisostearate, polyglyceryl-3 diisostearate, ethyl panthenol, sucrose containing 6-8 soybean fatty chains, triisostearyl trilinoleate, 2-octyldodecyl benzoate, 2-ethylhexyl benzoate, isofol-12 trimellitate, C12-C15 alkylbenzoate, the hydrogenated dimer dilinoleyl/dimethylcarbonate copolymer, triisodecyl trimellitate, tridecyl trimellitate, tri(2-ethylhexyl) trimellitate, castor oil benzoate (ratio 1/1.5) and dipropylene glycol dibenzoate;
plant oils such as arara oil, jojoba oil, pracaxi oil, virgin olive oil, *Limnanthes* (meadowfoam) oil, sesame seed oil, *Ximenia* oil, soybean oil, macadamia oil and castor oil;
oils comprising PEG or POE groups, such as PEG (6 OE), octyldodecyl PPG-3 myristyl ether dimer dilinoleate and PEG (8 OE);
the PVP/hexadecene copolymer;
and mixtures thereof.

The hydrocarbon-based oil having a refractive index>1.42 may also be an oligomer of a triglyceride of hydroxylated fatty acid and of saturated diacid.

Such an oligomer is obtained by reaction of a triglyceride of hydroxylated fatty acid (such as hydrogenated castor oil) and of a saturated diacid.

According to the invention, the diacid is said to be saturated when the hydrocarbon-based chain from which it is constituted does not have an unsaturated group, i.e. a carbon-carbon double bond. The term "diacid" means a hydrocarbon-based compound comprising two —COOH carboxyl functions. The diacid can be a single diacid or a mixture of several diacids.

Likewise, in the meaning of the invention, the oligomer can be a mixture of several oligomers.

Among the saturated diacids that can be used, mention may be made of sebacic acid (or 1,10-decanedioic acid), succinic acid, adipic acid, azelaic acid, octadecamethylene dicarboxylic acid and eicosadicarboxylic acid.

More particularly, the oligomer can be an oligoester whose monomers are represented by the following formulae (A) of triglyceride and (B) of diacid:

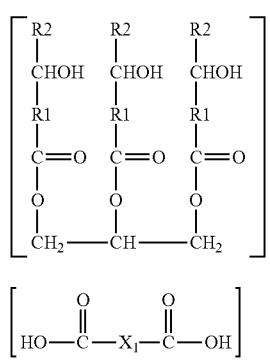

in which:
$R_1$ represents a saturated or unsaturated, linear or branched alkylene group comprising for example from 1 to 18 carbon atoms, and $R_2$ represents a saturated or unsaturated, linear or branched alkyl group comprising for example from 1 to 12 carbon atoms;
$R_1$ preferably represents a group —$(CH_2)_n$—, where n can vary from 1 to 20 and especially from 3 to 16, for example from 6 to 12;
$R_2$ preferably represents a group —$(CH_2)_m CH_3$, where m can vary from 0 to 11 and especially from 2 to 11, for example from 3 to 9.

According to one embodiment, n=10 and m=5, and the group

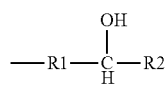

represents the alkyl residue of 12-hydroxystearic acid (the major component of hydrogenated castor oil);
$X_1$ is a linear or branched alkylene group, for example a linear alkylene group —$(CH_2)_x$—,
where x can vary from 1 to 30 and especially from 3 to 15.
When the diacid is sebacic acid, x is equal to 8.

The average degree of polymerization of the oligomer may vary between 3 and 12.

The oligoester of hydrogenated castor oil and of sebacic acid is especially sold by the company CRODA under various names depending on the degree of polymerization.

Among the oligoesters formed from hydrogenated castor oil and sebacic acid, the one with a degree of polymerization of about 4.6 is available under the trade name "CROMADOL CWS-5" and the one with a degree of polymerization of about 9.5 is available under the trade name "CROMADOL CWS-10", sold by Croda Japan K.K.

Mention may also be made of the oligomer of hydrogenated castor oil and sebacic acid sold under the name CRODABOND-CSA (MW=3500) by the company CRODA.

Mention may also be made, as oil having a refractive index greater than 1.42, of oils preferably having a high molar mass ranging from 650 to 10 000 g/mol, and preferably between 750 and 7500 g/mol, chosen from:
lipophilic polymers such as:
polybutylenes such as Indopol H-100 (of molar mass or MM=965 g/mol), Indopol H-300 (MM=1340 g/mol) and Indopol H-1500 (MM=2160 g/mol) sold or manufactured by the company Amoco,
hydrogenated polyisobutylenes such as Panalane H-300 E sold or manufactured by the company Amoco (MM=1340 g/mol), Viseal 20000 sold or manufactured by the company Synteal (MM=6000 g/mol) and Rewopal PIB 1000 sold or manufactured by the company Witco (MM=1000 g/mol),
polydecenes and hydrogenated polydecenes such as: Puresyn 10 (MM=723 g/mol) and Puresyn 150 (MM=9200 g/mol) sold or manufactured by the company Mobil Chemicals,
vinylpyrrolidone copolymers such as the vinylpyrrolidone/1-hexadecene copolymer, Antaron V-216 sold or manufactured by the company ISP (MM=7300 g/mol),
esters such as:
linear fatty acid esters with a total carbon number ranging from 35 to 70, for instance pentaerythrityl tetrapelargonate (MM=697 g/mol);
hydroxylated esters such as polyglyceryl-2 triisostearate (MM=965 g/mol),
aromatic esters such as tridecyl trimellitate (MM=757 g/mol),
$C_{24}$-$C_{28}$ branched fatty alcohol or fatty acid esters, such as those described in patent application EP-A-0 955 039 and especially triisoarachidyl citrate (MM=1033.76 g/mol), pentaerythrityl tetraisononanoate (MM=697 g/mol), glyceryl triisostearate (MM=891 g/mol), glyceryl tris(2-decyl)tetradecanoate (MM=1143 g/mol), pentaerythrityl tetraisostearate (MM=1202 g/mol), polyglyceryl-2 tetraisostearate (MM=1232 g/mol) or alternatively pentaerythrityl tetrakis(2-decyl)tetradecanoate (MM=1538 g/mol),
a polyester resulting from the esterification of at least one triglyceride of hydroxylated carboxylic acid(s) with an aliphatic monocarboxylic acid and with an aliphatic dicarboxylic acid, which is optionally unsaturated, for instance the succinic acid and isostearic acid castor oil sold under the reference Zenigloss by Zenitech;
esters of a diol dimer and of a diacid dimer of general formula HO—$R^1$—(—OCO—$R^2$—COO—$R^1$—)$_n$—OH, in which:
$R^1$ represents a diol dimer residue obtained by hydrogenation of dilinoleic diacid, $R^2$ represents a hydrogenated dilinoleic diacid residue, and h represents an integer ranging from 1 to 9,
especially the esters of dilinoleic diacids and of dilinoleyl diol dimers sold by the company Nippon Fine Chemical under the trade names Lusplan DD-DA5® and DD-DA7®,
silicone oils such as phenyl silicones, for instance Belsil PDM 1000 from the company Wacker (MM=9000 g/mol),
oils of plant origin, such as sesame oil (820 g/mol),
and mixtures thereof.

According to one particular embodiment of the invention, the composition comprises, as oil having a refractive index>1.42 or additional oil, at least one silicone oil or silicone gum.

In particular, it will be a phenyl silicone oil.

Silicone Oils

According to a second embodiment, the compositions according to the invention comprise at least one non-volatile silicone oil.

The non-volatile silicone oil that may be used in the invention may be chosen from silicone oils with a viscosity at 25° C. of greater than or equal to 9 centistokes (cSt) ($9 \times 10^{-6}$ m$^2$/s) and less than 800 000 cSt, preferably between 50 and 600 000 cSt and preferably between 100 and 500 000 cSt. The viscosity of this silicone may be measured according to standard ASTM D-445.

Among these silicone oils, two types of oil may be distinguished, according to whether or not they contain phenyl.

Representative examples of these non-volatile linear silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

Thus, non-phenyl non-volatile silicone oils that may be mentioned include:
PDMSs comprising alkyl or alkoxy groups, which are pendent and/or at the end of the silicone chain, these groups each containing from 2 to 24 carbon atoms,
PDMSs comprising aliphatic groups, or functional groups such as hydroxyl, thiol and/or amine groups,
polyalkylmethylsiloxanes optionally substituted with a fluorinated group, such as polymethyltrifluoropropyldimethylsiloxanes,
polyalkylmethylsiloxanes substituted with functional groups such as hydroxyl, thiol and/or amine groups,
polysiloxanes modified with fatty acids, fatty alcohols or polyoxyalkylenes, and mixtures thereof.

According to one embodiment, a composition according to the invention contains at least one non-phenyl linear silicone oil.

The non-phenyl linear silicone oil may be chosen especially from the silicones of formula:

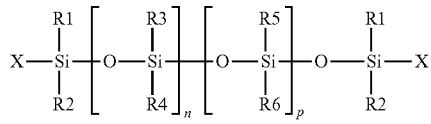

in which:
$R_1$, $R_2$, $R_5$ and $R_6$ are, together or separately, an alkyl radical containing 1 to 6 carbon atoms,
$R_3$ and $R_4$ are, together or separately, an alkyl radical containing from 1 to 6 carbon atoms, a vinyl radical, an amine radical or a hydroxyl radical,
X is an alkyl radical containing from 1 to 6 carbon atoms, a hydroxyl radical or an amine radical,
n and p are integers chosen so as to have a fluid compound.

As non-volatile silicone oils that may be used according to the invention, mention may be made of those for which:
the substituents $R_1$ to $R_6$ and X represent a methyl group, and p and n are such that the viscosity is 500 000 cSt, such as the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning,
the substituents $R_1$ to $R_6$ and X represent a methyl group, and p and n are such that the viscosity is 60 000 cSt, such as the product sold under the name Dow Corning 200 Fluid 60000 CS by the company Dow Corning, and the product sold under the name Wacker Belsil DM 60 000 by the company Wacker,
the substituents $R_1$ to $R_6$ and X represent a methyl group, and p and n are such that the viscosity is 350 cSt, such as the product sold under the name Dow Corning 200 Fluid 350 CS by the company Dow Corning,
the substituents $R_1$ to $R_6$ represent a methyl group, the group X represents a hydroxyl group, and n and p are such that the viscosity is 700 cSt, such as the product sold under the name Baysilone Fluid T0.7 by the company Momentive.

Silicone Gums

The silicone gum that may be used in the invention may be chosen from silicone gums with a viscosity at 25° C. of greater than 800 000 centistokes (cSt), especially between 800 000 and 10 000 000 cSt, preferably between 1 000 000 and 5 000 000 cSt and preferably between 1 000 000 and 2 500 000 cSt. The viscosity of this silicone may be measured according to standard ASTM D-445.

The molecular weight of the silicone gums is generally greater than 350 000 g/mol, between 350 000 and 800 000 g/mol and preferably from 450 000 to 700 000 g/mol.

The silicone gum may be chosen especially from the silicones of formula:

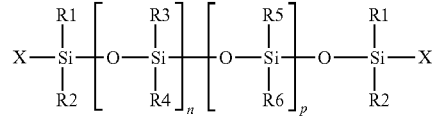

in which:
$R_1$, $R_2$, $R_5$ and $R_6$ are, together or separately, an alkyl radical containing 1 to 6 carbon atoms,
$R_3$ and $R_4$ are, together or separately, an alkyl radical containing from 1 to 6 carbon atoms, a vinyl radical, an amine radical or a hydroxyl radical,
X is an alkyl radical containing from 1 to 6 carbon atoms, a hydroxyl radical or an amine radical,
n and p being integers chosen such that the viscosity of the compound is greater than 800 000 cSt.

As silicone gums that may be used according to the invention, mention may be made of those for which:
the substituents $R_1$ to $R_6$ represent a methyl group, the group X represents a methyl group, and n and p are such that the molecular weight of the polymer is 600 000 g/mol, such as the product sold under the name Mirasil C-DPDM by the company Bluestar;

the substituents $R_1$ to $R_6$ represent a methyl group, the group X represents a hydroxyl group, and n and p are such that the molecular weight of the polymer is 600 000 g/mol, such as the product sold under the name SGM 36 by the company Dow Corning;

dimethicones of the (polydimethylsiloxane)(methylvinylsiloxane) type, such as SE63 sold by GE Bayer Silicones, poly(dimethylsiloxane)(diphenyl)(methylvinylsiloxane) copolymers, and mixtures thereof.

According to one preferred embodiment, the composition comprises at least one phenyl silicone oil.

Phenyl Silicone Oils

The term "phenyl silicone" (also referred to as phenyl silicone oil) means an organopolysiloxane substituted with at least one phenyl group.

The phenyl silicone is preferably non-volatile. The term "non-volatile" refers to an oil whose vapour pressure at room temperature and atmospheric pressure is non-zero and is less than 0.02 mmHg (2.66 Pa) and better still less than $10^{-3}$ mmHg (0.13 Pa).

The phenyl silicone oil may be chosen from phenyl trimethicones, phenyl dimethicones, phenyltrimethylsiloxydiphenylsiloxanes, diphenyl dimethicones, diphenylmethyldiphenyltrisiloxanes, triméthylpentaphenyltrisiloxane and 2-phenylethyl trimethylsiloxysilicates.

The silicone oil may correspond to the formula:

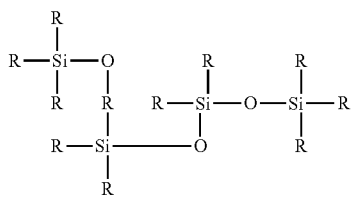

in which the R groups represent, independently of each other, a methyl or a phenyl. Preferably, in this formula, the silicone oil comprises at least three, for example at least four, at least five or at least six, phenyl groups.

According to another embodiment, the silicone oil corresponds to the formula:

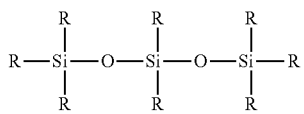

in which the R groups represent, independently of each other, a methyl or a phenyl.

Preferably, in this formula, said organopolysiloxane comprises at least three, for example at least four or at least five, phenyl groups.

Mixtures of the phenyl organopolysiloxanes described previously may be used.

Examples that may be mentioned include mixtures of triphenyl, tetraphenyl or pentaphenyl organopolysiloxanes.

According to another embodiment, the silicone oil corresponds to the formula:

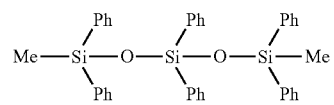

in which Me represents methyl and Ph represents phenyl. Such a phenyl silicone is especially manufactured by Dow Corning under the reference Dow Corning 555 Cosmetic Fluid (INCI name: trimethyl pentaphenyl trisiloxane). The reference Dow Corning 554 Cosmetic Fluid may also be used.

According to another embodiment, the silicone oil corresponds to the formula:

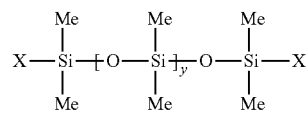

in which Me represents methyl, y is between 1 and 1000 and X represents —$CH_2$—$CH(CH_3)$(Ph).

According to another embodiment, the silicone oil corresponds to the formula:

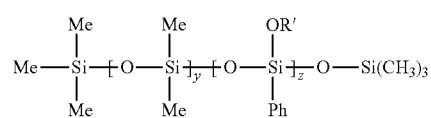

in which —OR' represents —O—$SiMe_3$, y is between 1 and 1000 and z is between 1 and 1000.

The phenyl silicone oil may be chosen from the phenyl silicones of formula (VI) below:

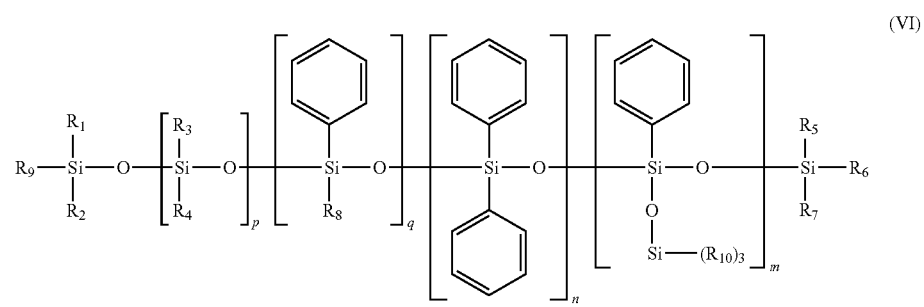

(VI)

in which:
R$_1$ to R$_{10}$, independently of each other, are saturated or unsaturated, linear, cyclic or branched C$_1$-C$_{30}$ hydrocarbon-based radicals,
m, n, p and q are, independently of each other, integers between 0 and 900, with the proviso that the sum m+n+q is other than 0.

Preferably, the sum m+n+q is between 1 and 100. Preferably, the sum m+n+p+q is between 1 and 900 and better still between 1 and 800. Preferably, q is equal to 0.

The phenyl silicone oil may be chosen from the phenyl silicones of formula (VII) below:

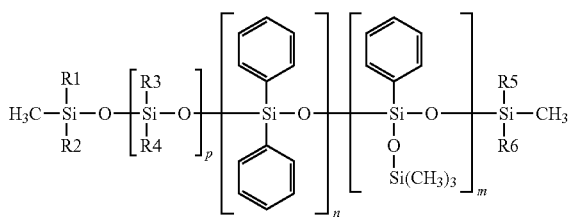

(VII)

in which:
R1 to R6, independently of each other, are saturated or unsaturated, linear, cyclic or branched C$_1$-C$_{30}$ hydrocarbon-based radicals,
m, n and p are, independently of each other, integers between 0 and 100, with the proviso that the sum n+m is between 1 and 100.

Preferably, R1 to R6, independently of each other, represent a saturated, linear or branched C$_1$-C$_{30}$ and especially C$_1$-C$_{12}$ hydrocarbon-based radical, and in particular a methyl, ethyl, propyl or butyl radical.

R1 to R6 may especially be identical, and may also be a methyl radical.

Preferably, the value m=1 or 2 or 3, and/or n=0 and/or p=0 or 1 may apply, in formula (VII).

A phenyl silicone oil of formula (VI) with a viscosity at 25° C. of between 5 and 1500 mm$^2$/s (i.e. 5 to 1500 cSt), and preferably with a viscosity of between 5 and 1000 mm$^2$/s (i.e. 5 to 1000 cSt) may be used.

As phenyl silicone oils of formula (VII), it is especially possible to use phenyl trimethicones such as DC556 from Dow Corning (22.5 cSt), the oil Silbione 70663V30 from Rhône-Poulenc (28 cSt) or diphenyl dimethicones such as Belsil oils, especially Belsil PDM1000 (1000 cSt), Belsil PDM 200 (200 cSt) and Belsil PDM 20 (20 cSt) from Wacker. The values in parentheses represent the viscosities at 25° C.

The non-volatile silicone oil may be chosen from the silicones of formula:

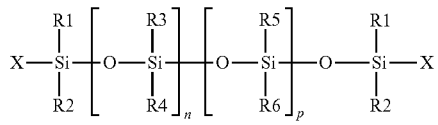

in which:
R$_1$, R$_2$, R$_5$ and R$_6$ are, together or separately, an alkyl radical containing 1 to 6 carbon atoms,
R$_3$ and R$_4$ are, together or separately, an alkyl radical containing from 1 to 6 carbon atoms or an aryl radical,
X is an alkyl radical containing from 1 to 6 carbon atoms, a hydroxyl radical or a vinyl radical,
n and p being chosen so as to give the oil a weight-average molecular weight of less than 200 000 g/mol, preferably less than 150 000 g/mol and more preferably less than 100 000 g/mol.

The refractive index of the phenyl silicone oil will be preferably >1.42. Preferably, the index will be advantageously greater than 1.43, preferably greater than 1.45 and more preferably greater than 1.46.

The hydrocarbon-based oil having a refractive index>1.42 and having $\delta_a$>1 and/or the phenyl silicone oil according to the invention is present in the composition in a content ranging from 0.1% to 50% by weight relative to the total weight of said composition, preferably from 0.5% to 30% by weight, and better still from 1% to 20% by weight relative to the total weight of the composition.

Galenic Form

The present invention relates to cosmetic compositions, especially of emulsion type, which may be in the form of a composition for caring for and/or making up keratin materials, in particular the skin, or else in the form of a sun protection composition.

It may then be in a colourless form, optionally containing cosmetic or dermatological active agents. It may then be used as a care or makeup base for keratin materials, in particular the skin.

A composition of the invention may also be in the form of a coloured product for making up keratin materials, in particular for making up skin, such as a foundation in particular to be applied to the face or the neck, a concealer, a complexion corrector, a tinted cream or a body makeup composition.

The composition according to the invention may be in various forms, in particular in the form of an anhydrous composition, dispersion or emulsion, especially such as a water/oil or oil/water emulsion or multiple emulsion.

A composition of the invention is preferably an emulsion, in particular a direct or inverse emulsion, or an anhydrous composition.

A dispersion may be made as an aqueous phase or as an oily phase.

An emulsion may have an oily or aqueous continuous phase. Such an emulsion may be, for example, an inverse (W/O) emulsion or a direct (O/W) emulsion, or alternatively a multiple emulsion (W/O/W or O/W/O).

In the case of emulsions, inverse (W/O) emulsions are preferred.

An anhydrous composition is a composition containing less than 5% by weight of water, or even less than 2% of water, and is especially free of water. Where appropriate, such small amounts of water may especially be introduced by ingredients of the composition that may contain residual amounts thereof.

In particular, the composition according to the invention may be in the form of an oil-in-water (O/W) emulsion, a water-in-oil (W/O) emulsion, or a multiple emulsion, preferably a water-in-oil (W/O) emulsion.

The composition according to the invention may form a base composition, or a care and/or makeup composition, or a composition to be applied under or on top of another makeup and/or care composition, in small touches in order to unify the complexion.

In the case where the composition according to the invention is a care and/or makeup base, it will advantageously be unpigmented, allowing the use in said base of a high content of dispersion (pre-dispersion) of bismuth oxychloride in 2-ethylhexyl hydroxystearate. This care and/or makeup base may be applied to the whole of the face, before the application of a care composition and/or of a makeup composition. According to another embodiment, said care and/or makeup base will be used as touches of makeup before (underneath) of after (on top of) the application of a layer of a care or makeup composition (foundation).

According to one particular embodiment, said composition is applied in touches to the areas of the face exhibiting skin defects; this application may take place before the subsequent application of a foundation or afterwards. According to another particular embodiment, it may be applied around the eyes in order to illuminate the eye area or above the lips, on the cupid's bow, to give a curved shape.

According to one particular embodiment, said composition is applied to people with skin that has visible and/or tactile unevenness and/or a heterogeneity of the complexion.

According to one particular embodiment of the invention, said composition is applied to people with oily skin.

According to another particular embodiment of the invention, said composition is applied to people with aged skin or mature skin.

According to another particular embodiment of the invention, said composition is applied to people with Asiatic skin.

Physiologically Acceptable Medium

Besides the compounds indicated previously, a composition according to the invention comprises a physiologically acceptable medium.

The term "physiologically acceptable medium" is intended to denote a medium that is particularly suitable for applying a composition of the invention to keratin materials, in particular the skin.

The physiologically acceptable medium is generally adapted to the nature of the support onto which the composition is to be applied, and also to the form in which the composition is to be packaged.

Aqueous Phase

A composition of the invention may comprise an aqueous phase in a content ranging from 0 to 80%, in particular from 1% to 80% by weight, in particular from 10% to 80% and more particularly from 20% to 60% by weight, in particular from 30% to 50% by weight relative to the total weight of the composition.

According to one particular embodiment, a composition of the invention comprises an aqueous phase in a content ranging from 10% to 80% and more particularly from 20% to 60% by weight, especially from 30% to 50% by weight relative to the total weight of the composition.

The aqueous phase generally comprises water such as: a demineralized water, a water from a natural source, such as La Roche-Posay water, a floral water such as cornflower water and/or a spring water.

According to one embodiment, a composition of the invention may also comprise at least one water-miscible, organic solvent.

The water-miscible, organic solvent(s) suitable for the invention may be chosen from $C_{1-8}$, and especially $C_{1-5}$, monoalcohols, especially ethanol, isopropanol, tert-butanol, n-butanol, polyols as described previously, and mixtures thereof.

A composition of the invention may also comprise at least one salt, for example sodium chloride, magnesium chloride or magnesium sulphate.

A composition of the invention may comprise from 0.05% to 1.5%, in particular from 0.1% to 1.0% and more particularly from 0.15% to 0.8% by weight of salts relative to the total weight of the composition.

According to one particular embodiment, the aqueous phase forms at least 30% by weight, in particular at least 45% by weight, or more than 50% by weight and especially more than 60% by weight of the total weight of the composition according to the invention. Preferably, the aqueous phase is present in the emulsion according to the invention in a content ranging from 30% to 70% by weight, preferably ranging from 40% to 60% by weight, and better still from 50% to 60% by weight, relative to the total weight of the emulsion.

The composition may also comprise, in particular when the composition comprises an aqueous phase representing at least 30% by weight relative to the total weight of the composition, at least one lower $C_2$ to $C_8$ monoalcohol.

The lower monoalcohols that are more particularly suitable for use in the invention comprise from 2 to 8 carbon atoms, especially from 2 to 6 carbon atoms and in particular from 2 to 4 carbon atoms, for instance ethanol, isopropanol, propanol and butanol.

Ethanol and isopropanol are thus very particularly suitable for the invention, preferably ethanol.

As specified previously, this alcohol is present in a proportion of at least 5%, in particular of at least 7%, especially in a proportion of at least 10% by weight relative to the total weight of the composition.

For reasons of comfort, a content of less than or equal to 20% by weight and especially less than or equal to 15% by weight of monoalcohol relative to the total weight of the compositions according to the invention will be favoured, in other words a content of less than or equal to 40% by weight and especially less than or equal to 30% by weight relative to the total weight of the aqueous phase of said compositions.

Thus, the monoalcohol may represent at least 10% by weight, or even 20% by weight and up to 40% by weight of the aqueous phase.

Liquid Fatty Phase

A cosmetic composition in accordance with the present invention may comprise at least one liquid and/or solid fatty phase and especially at least one oil as mentioned below.

The term "oil" means any fatty substance that is in liquid form at room temperature (20-25° C.) and at atmospheric pressure.

A composition of the invention may comprise a liquid fatty phase in a content ranging from 5% to 95%, in particular from 10% to 80%, in particular from 15% to 70% and more particularly from 20% to 65% by weight relative to the total weight of the composition.

The oily phase that is suitable for preparing the cosmetic compositions according to the invention may comprise hydrocarbon-based oils, silicone oils, fluoro oils or non-fluoro oils, or mixtures thereof.

The oils may be volatile or non-volatile.

They may be of animal, plant, mineral or synthetic origin.

For the purposes of the present invention, the term "volatile oil" means an oil (or non-aqueous medium) capable of evaporating on contact with the skin in less than one hour, at room temperature and at atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg), and preferentially ranging from 1.3 Pa to 1300 Pa (0.01 to 10 mmHg).

For the purposes of the present invention, the term "non-volatile oil" means an oil with a vapour pressure of less than 0.13 Pa.

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulphur and/or phosphorus atoms, for example in the form of hydroxyl or acid radicals.

Volatile Oils

The volatile oils may be chosen from hydrocarbon-based oils containing from 8 to 16 carbon atoms, and especially $C_8$-$C_{16}$ branched alkanes (also known as isoparaffins), for instance isododecane (also known as 2,2,4,4,6-pentamethylheptane), isodecane and isohexadecane, and for example the oils sold under the trade names ISOPAR® or PERMETHYL®, volatile linear alkanes, and mixtures thereof.

According to one advantageous embodiment, the volatile linear alkanes that are suitable for the invention have an evaporation rate ranging from 0.01 to 3.5 mg/cm²/min, at room temperature (25° C.) and atmospheric pressure (760 mmHg), and comprise from 9 to 14 carbon atoms. By way of example, mention may be made of n-nonane (C9), n-decane (C10), n-undecane (C11), n-dodecane (C12), n-tridecane (C13) and n-tetradecane (C14), and mixtures thereof. According to one particular embodiment, the volatile linear alkane is chosen from n-nonane, n-undecane, n-dodecane, n-tridecane and n-tetradecane, and mixtures thereof. Preferably, the volatile linear alkane(s) are chosen from n-undecane, n-dodecane, n-tridecane and n-tetradecane, and mixtures thereof. According to one preferred embodiment, the composition according to the invention comprises dodecane. According to another preferred embodiment, the composition according to the invention comprises tetradecane. According to another preferred embodiment, mention may be made of mixtures of n-undecane (C11) and of n-tridecane (C13) obtained in Examples 1 and 2 of patent application WO 2008/155059 by the company Cognis. Mention may also be made of n-dodecane (C12) and n-tetradecane (C14) such as those sold by Sasol under the references, respectively, Parafol 12-97 and Parafol 14-97, and also mixtures thereof.

Volatile oils that may also be used include volatile silicones, for instance volatile linear or cyclic silicone oils, especially those with a viscosity≤8 centistokes (cSt) (8×10⁻⁶ m²/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyl-octyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethyl-cyclopentane, and mixtures thereof, may also be used.

Non-Volatile Oils

The non-volatile oils may be chosen especially from non-volatile hydrocarbon-based, fluoro and/or silicone oils.

Non-volatile hydrocarbon-based oils that may especially be mentioned include:

hydrocarbon-based oils of animal origin, hydrocarbon-based oils of plant origin, such as phytostearyl esters, such as phytostearyl oleate, phytostearyl isostearate and lauroylloctyldodecyl/phytostearyl glutamate (Ajinomoto, Eldew PS203), triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, millet oil, barley oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camelina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, *quinoa* oil, musk rose oil, sesame oil, soybean oil, sunflower oil, castor oil and watermelon oil, and mixtures thereof, or alternatively caprylic/capric acid triglycerides, such as those sold by the company STEARINERIES DUBOIS or those sold under the names MIGLYOL 810®, 812® and 818® by the company Dynamit Nobel;

synthetic ethers containing from 10 to 40 carbon atoms, such as dicaprylyl ether;

synthetic esters, for instance oils of formula $R_1COOR_2$, in which $R_1$ represents a linear or branched fatty acid residue containing from 1 to 40 carbon atoms, and $R_2$ represents a hydrocarbon-based chain that is especially branched, containing from 1 to 40 carbon atoms provided that $R_1+R_2 \geq 10$. The esters may be chosen especially from alcohol fatty acid esters, for instance cetostearyl octanoate, Isopropyl alcohol esters, such as isopropyl myristate, isopropyl palmitate, ethyl palmitate, 2-ethylhexyl palmitate, isopropyl stearate, octyl stearate, hydroxylated esters, for instance isostearyl lactate, octyl hydroxystearate, alcohol or polyalcohol ricinoleates, hexyl laurate, neopentanoic acid esters, for instance isodecyl neopentanoate, isotridecyl neopentanoate, and isononanoic acid esters, for instance isononyl isononanoate and isotridecyl isononanoate.

polyol esters and pentaerythritol esters, for instance dipentaerythrityl tetrahydroxystearate/tetraisostearate, fatty alcohols that are liquid at room temperature, with a branched and/or unsaturated carbon-based chain containing from 12 to 26 carbon atoms, for instance 2-octyldodecanol, isostearyl alcohol and oleyl alcohol;

$C_{12}$-$C_{22}$ higher fatty acids, such as oleic acid, linoleic acid or linolenic acid, and mixtures thereof;

dialkyl carbonates, the two alkyl chains possibly being identical or different, such as dicaprylyl carbonate sold under the name CETIOL CC® by Cognis; and oils of high molar mass, in particular with a molar mass ranging from about 400 to about 2000 g/mol and in particular from about 650 to about 1600 g/mol. As oils of high molar mass that may be used in the present invention, mention may be made especially of linear fatty acid esters with a total carbon number ranging from 35 to 70, for instance pentaerythrityl tetrapelargonate, hydroxylated esters, such as polyglyceryl-2 triisostearate, aromatic esters, such as tridecyl trimellitate, branched $C_{24}$-$C_{28}$ fatty alcohol or fatty acid esters, such as those described in U.S. Pat. No. 6,491,927, and pentaerythritol esters, and especially triisoarachidyl citrate, glyceryl triisostearate, glyceryl tris(2-decyl)tetradecanoate, polyglyceryl-2 tetraisostearate or pentaerythrityl tetrakis(2-decyl)tetradecanoate; phenyl silicones, such as Belsil PDM 1000 from the company Wacker (MM=9000 g/mol), non-volatile polydimethylsiloxanes (PDMS), PDMSs comprising alkyl or alkoxy groups that are pendent and/or at the end of the silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, dimethicones or phenyl trimethicones with a viscosity of less than or equal to 100 cSt, and mixtures thereof; and also mixtures of these various oils.

Surfactants

A composition according to the invention generally comprises at least one surfactant, chosen especially from amphoteric, anionic, cationic and nonionic surfactants, used alone or as a mixture.

The surfactants are generally present in the composition in a proportion that may range, for example, from 0.3% to 20% by weight, in particular from 0.5% to 15% by weight and more particularly from 1% to 10% by weight of surfactants relative to the total weight of the composition.

Needless to say, the surfactant is chosen so as to effectively stabilize the emulsions more particularly under consideration according to the invention, namely of O/W, W/O or O/W/O type. This choice falls within the competence of a person skilled in the art.

Examples that may be mentioned for the O/W emulsions include nonionic surfactants, and especially esters of polyols and of fatty acids with a saturated or unsaturated chain containing, for example, from 8 to 24 carbon atoms and better still from 12 to 22 carbon atoms, and the oxyalkylenated derivatives thereof, i.e. derivatives containing oxyethylenated and/or oxypropylenated units, such as the glyceryl esters of $C_8$-$C_{24}$ fatty acids, and the oxyalkylenated derivatives thereof; the polyethylene glycol esters of $C_8$-$C_{24}$ fatty acids, and the oxyalkylenated derivatives thereof; the sorbitol esters of $C_8$-$C_{24}$ fatty acids, and the oxyalkylenated derivatives thereof; the sugar (sucrose, glucose or alkylglucose) esters of $C_8$-$C_{24}$ fatty acids, and the oxyalkylenated derivatives thereof; fatty alcohol ethers; the sugar ethers of $C_8$-$C_{24}$ fatty alcohols, and mixtures thereof.

Glyceryl esters of fatty acids that may especially be mentioned include glyceryl stearate (glyceryl monostearate, distearate and/or tristearate) (CTFA name: glyceryl stearate) or glyceryl ricinoleate, and mixtures thereof.

Polyethylene glycol esters of fatty acids that may especially be mentioned include polyethylene glycol stearate (polyethylene glycol monostearate, distearate and/or tristearate) and more especially polyethylene glycol 50 OE monostearate (CTFA name: PEG-50 stearate) and polyethylene glycol 100 OE monostearate (CTFA name: PEG-100 stearate), and mixtures thereof.

Mixtures of these surfactants may also be used, for instance the product containing glyceryl stearate and PEG-100 stearate, sold under the name Arlacel 165 by the company Uniqema, and the product containing glyceryl stearate (glyceryl mono-distearate) and potassium stearate, sold under the name Tegin by the company Goldschmidt (CTFA name: glyceryl stearate SE).

Fatty acid esters of glucose or of alkylglucose that may be mentioned in particular include glucose palmitate, alkylglucose sesquistearates, for instance methylglucose sesquistearate, alkylglucose palmitates, for instance methylglucose palmitate or ethylglucose palmitate, fatty esters of methylglucoside and more especially the diester of methylglucoside and of oleic acid (CTFA name: methyl glucose dioleate); the mixed ester of methylglucoside and of the oleic acid/hydroxystearic acid mixture (CTFA name: methyl glucose dioleate/hydroxysterate); the ester of methylglucoside and of isostearic acid (CTFA name: methyl glucose isostearate); the ester of methylglucoside and of lauric acid (CTFA name: methyl glucose laurate); the mixture of the monoester and diester of methylglucoside and of isostearic acid (CTFA name: methyl glucose sesquiisostearate); the mixture of the monoester and diester of methylglucoside and of stearic acid (CTFA name: methyl glucose sesquistearate) and in particular the product sold under the name Glucate SS by the company Amerchol, and mixtures thereof.

Examples of oxyethylenated ethers of a fatty acid and of glucose or of alkylglucose that may be mentioned include the oxyethylenated ethers of a fatty acid and of methylglucose, and in particular the polyethylene glycol ether of the diester of methyl glucose and of stearic acid containing about 20 mol of ethylene oxide (CTFA name: PEG-methyl glucose distearate), such as the product sold under the name Glucam E-20 distearate by the company Amerchol; the polyethylene glycol ether of the mixture of monoester and diester of methylglucose and of stearic acid containing about 20 mol of ethylene oxide (CTFA name: PEG-20 methyl glucose sesquistearate) and in particular the product sold under the name Glucamate SSE-20 by the company Amerchol, and the product sold under the name Grillocose PSE-20 by the company Goldschmidt, and mixtures thereof.

Examples of sucrose esters that may be mentioned include sucrose palmitostearate, sucrose stearate and sucrose monolaurate.

Examples of fatty alcohol ethers that may be mentioned include polyethylene glycol ethers of fatty alcohols containing from 8 to 30 carbon atoms and especially from 10 to 22 carbon atoms, such as polyethylene glycol ethers of cetyl alcohol, of stearyl alcohol or of cetearyl alcohol (mixture of cetyl alcohol and stearyl alcohol). Examples that may be mentioned include ethers comprising from 1 to 200 and preferably from 2 to 100 oxyethylene groups, such as those of CTFA name Ceteareth-20 and Ceteareth-30, and mixtures thereof.

Sugar ethers that may especially be mentioned are alkylpolyglucosides, for example decylglucoside, for instance the product sold under the name Mydol 10 by the company Kao Chemicals, the product sold under the name Plantaren 2000 by the company Henkel, and the product sold under the name Oramix NS 10 by the company SEPPIC; caprylyl/capryl glucoside, for instance the product sold under the name Oramix CG 110 by the company SEPPIC or under the name Lutensol GD 70 by the company BASF; laurylglucoside, for instance the products sold under the names Plantaren 1200 N and Plantacare 1200 by the company Henkel; cocoglucoside, for instance the product sold under the name Plantacare 818/UP by the company Henkel; cetostearyl glucoside optionally as a mixture with cetostearyl alcohol, sold, for example, under the name Montanov 68 by the company SEPPIC, under the name Tego-Care CG90 by the company Goldschmidt and under the name Emulgade KE3302 by the company Henkel; arachidyl glucoside, for example in the form of the mixture of arachidyl alcohol and behenyl alcohol and arachidyl glucoside, sold under the name Montanov 202 by the company SEPPIC; cocoyleth-ylglucoside, for example in the form of the mixture (35/65) with cetyl alcohol and stearyl alcohol, sold under the name Montanov 82 by the company SEPPIC; and mixtures thereof.

For the W/O emulsions, hydrocarbon-based or silicone surfactants may be used.

According to one embodiment variant, hydrocarbon-based surfactants are preferred.

Examples of hydrocarbon-based surfactants that may be mentioned include polyester polyols, for instance PEG-30 dipolyhydroxystearate sold under the reference Arlacel P 135 by the company Uniqema, and polyglyceryl-2 dipoly-hydroxystearate sold under the reference Dehymuls PGPH by the company Cognis.

Examples of silicone surfactants that may be mentioned include alkyl dimethicone copolyols such as lauryl methi-cone copolyol sold under the name Dow Corning 5200 Formulation Aid by the company Dow Corning and cetyl dimethicone copolyol sold under the name Abil EM 90 by the company Goldschmidt, or the polyglyceryl-4 isostearate/cetyl dimethicone copolyol/hexyl laurate mixture sold under the name Abil WE 09 by the company Goldschmidt.

One or more co-emulsifiers may also be added thereto. The co-emulsifier may be chosen advantageously from the group comprising polyol alkyl esters. Polyol alkyl esters that may especially be mentioned include glycerol and/or sorbi-tan esters, for example the polyglyceryl-3 diisostearate sold under the name Lameform TGI by the company Cognis, polyglyceryl-4 isostearate, such as the product sold under the name Isolan GI 34 by the company Goldschmidt, sor-bitan isostearate, such as the product sold under the name Arlacel 987 by the company ICI, sorbitan glyceryl isoste-arate, such as the product sold under the name Arlacel 986 by the company ICI, and mixtures thereof.

A crosslinked elastomeric solid organopolysiloxane comprising at least one oxyalkylene group, such as the products obtained according to the procedure of Examples 3, 4 and 8 of document U.S. Pat. No. 5,412,004 and the examples of document U.S. Pat. No. 5,811,487, especially the product of Example 3 (synthetic example) of U.S. Pat. No. 5,412,004, and as sold under the reference KSG 21 by the company Shin-Etsu, may also be used as surfactants for W/O emulsions.

Surfactants of the amphiphilic polymer type are also suitable for the invention.

The term "amphiphilic polymer" is intended to mean any polymer comprising both a hydrophilic portion and a hydrophobic portion and having the property of forming a film separating two liquids of different polarity and thus making it possible to stabilize liquid-liquid dispersions of direct, inverse or multiple type. These polymers may be water-soluble or water-dispersible.

Use may more particularly be made of acrylate/$C_{10}$-$C_{30}$ alkyl acrylate copolymers, such as the products sold under the names Pemulen TR1, Pemulen TR2 and Carbobol 1382 by the company Goodrich, or else blends thereof. Use may also be made of the acrylate/steareth-20 itaconate copolymers and acrylate/ceteth-20 itaconate copolymers sold under the names Structure 2001 and Structure 3001 by the company National Starch. By way of terpolymers that can be used, mention may be made of the terpolymer of methacrylic acid/methyl acrylate/dimethyl m-isopropenylbenzyl isocya-nate of ethoxylated behenyl alcohol comprising 40 OE (i.e. comprising 40 oxyethylenated groups), sold by the company Amerchol under the names Viscophobe DB 1000 NP3-NP4.

Mention may also be made of crosslinked terpolymers of methacrylic acid, of ethyl acrylate and of polyethylene glycol (10 OE) ether of stearyl alcohol (Steareth 10), in particular those sold by the company Allied Colloids under the name Salcare SC 80.

The anionic polymers that can be used according to the invention are, for example, isophthalic acid or sul-phoisophthalic acid polymers, and in particular the copolymers of phthalate/sulphoisophthalate/glycol (for example diethylene glycol/phthalate/isophthalate/1,4-cyclohexanedi-methanol) sold under the names Eastman AQ polymer (AQ35S, AQ38S, AQ55S, AQ48 Ultra) by the company Eastman Chemical.

According to one particular embodiment, a silicone surfactant, in particular chosen from dimethicone copolyols, may be used.

Dimethicone Copolyol

The dimethicone copolyol according to the invention is an oxypropylenated and/or oxyethylenated polydimethylmeth-ylsiloxane.

Dimethicone copolyols that may be used are those corresponding to formula (II) below:

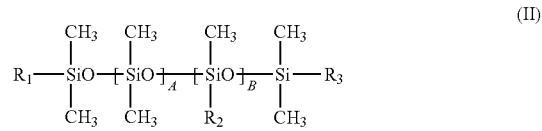

in which:

$R_1$, $R_2$ and $R_3$, independently of each other, represent a $C_1$-$C_6$ alkyl radical or a radical —$CH_2)_x$—$(OCH_2CH_2)_y$—$(OCH_2CH_2CH_2)_z$—$OR_4$, at least one radical $R_1$, $R_2$ or $R_3$ not being an alkyl radical; $R_4$ being a hydrogen, a $C_1$-$C_3$ alkyl radical or a $C_2$-$C_4$ acyl radical;

A is an integer ranging from 0 to 200;

B is an integer ranging from 0 to 50; on condition that A and B are not simultaneously equal to zero;

x is an integer ranging from 1 to 6;

y is an integer ranging from 1 to 30;

z is an integer ranging from 0 to 5.

According to one preferred embodiment of the invention, in the compound of formula (II), $R_1$=$R_3$=methyl radical, x is an integer ranging from 2 to 6 and y is an integer ranging from 4 to 30. $R_4$ is in particular a hydrogen.

Examples of compounds of formula (II) that may be mentioned include the compounds of formula (III):

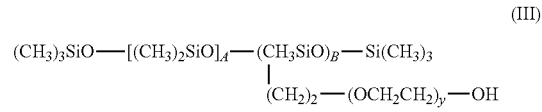

in which A is an integer ranging from 20 to 105, B is an integer ranging from 2 to 10 and y is an integer ranging from 10 to 20.

Examples of silicone compounds of formula (II) that may also be mentioned include the compounds of formula (IV):

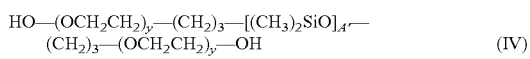

in which A' and y are integers ranging from 10 to 20.

Dimethicone copolyols that may be used include those sold under the names DC 5329, DC 7439-146, DC 2-5695 and Q4-3667 by the company Dow Corning; KF-6013, KF-6015, KF-6016 and KF-6017 by the company Shin-Etsu.

The compounds DC 5329, DC 7439-146 and DC 2-5695 are compounds of formula (III) in which, respectively, A is 22, B is 2 and y is 12; A is 103, B is 10 and y is 12; A is 27, B is 3 and y is 12.

The dimethicone copolyol may be present in the emulsion according to the invention in a content ranging from 1% to 6% by weight, preferably ranging from 1.5% to 4% by weight and preferentially ranging from 2% to 3% by weight, relative to the total weight of the emulsion.

According to one preferred embodiment variant of the invention, the aforementioned dimethicone copolyol may be combined with at least one α,ω-substituted oxyalkylenated silicone.

α,ω-Substituted Oxyalkylenated Silicone

In the text hereinbelow or hereinabove, the term "silicone" is intended to denote, in accordance with what is generally accepted, any organosilicon polymer or oligomer of linear or cyclic, branched or crosslinked structure, of variable molecular weight, obtained by polymerization and/or polycondensation of suitably functionalized silanes, and consisting essentially of a repetition of main units in which the silicon atoms are linked together via oxygen atoms (≡Si—O—Si≡ siloxane bond), optionally substituted hydrocarbon-based radicals being directly bonded via a carbon atom to said silicon atoms. The most common hydrocarbon-based radicals are alkyl radicals, especially $C_1$-$C_{10}$ alkyl radicals, and in particular methyl radicals, fluoroalkyl radicals and aryl radicals and in particular phenyl radicals. They may for example be substituted by $C_1$-$C_{40}$ ester or ether groups or $C_7$-$C_{60}$ aralkyl groups.

Thus, the α,ω-substituted oxyalkylenated silicone that can be used according to the invention is an organosilicon polymer as defined above, having a linear structure, which is substituted at the two ends of the main chain by oxyalkylenated groups linked to the Si atoms by means of a hydrocarbon-based group.

Preferably, the α,ω-substituted oxyalkylenated silicone corresponds to the general formula (I) below:

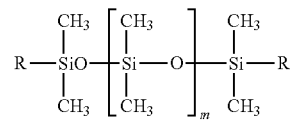

in which: R=—$(CH_2)_pO$—$(C_2H_4O)_x$ $(C_3H_6O)_yR^1$ where:
$R^1$ represents H, $CH_3$ or $CH_2CH_3$;
p is an integer ranging from 1 to 5, x varies from 1 to 100, y varies from 0 to 50;
it being possible for the units $(C_2H_4O)$ and $(C_3H_6O)$ to be distributed randomly or in blocks;
the R2 radicals represent a C1-C3 alkyl radical or a phenyl radical;
5≤m≤300, Preferably, the α,ω-substituted oxyalkylenated silicone used according to the present invention corresponds to the general formula (I) for which all the $R^2$ radicals are methyl radicals, and:
p ranges from 2 to 4,
x ranges from 3 to 100,
m ranges from 50 to 200, More preferably, the average molecular weight of R ranges from 800 to 2600.

Preferably, the weight ratio of the $C_2H_4O$ units relative to the $C_3H_6O$ units ranges from 100/10 to 20/80. Advantageously, this ratio is around 42/58.

More preferably, $R^1$ is the methyl group.

More preferably still, the emulsion according to the invention comprises the α,ω-substituted oxyalkylenated silicone of the following formula:

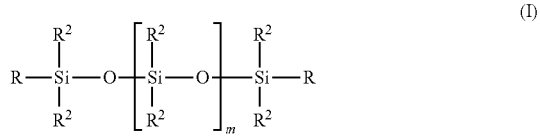

in which:
m=100,
R=$(CH_2)_3$—O—$(C_2H_4O)_x$—$(C_3H_6O)_y$—$CH_3$, where x ranges from 3 to 100, y ranges from 1 to 50, the weight ratio of the number of $C_2H_4O$ to the number of $C_3H_6O$ being around 42/58, the average molecular weight of R ranging from 800 to 1000.

The α,ω-substituted oxyalkylenated silicone as defined above may be used according to the invention in a proportion ranging from 0.5% to 5% in particular from 1% to 4% by weight and more particularly from 2% to 3% by weight relative to the total weight of the composition.

Among the commercial products which may contain all or some of the α,ω-substituted oxyalkylenated silicones that can be used according to the invention as emulsifier, mention may especially be made of those sold under the names Abil EM 97 by the company Goldschmidt, or else KF 6009, X22-4350, X22-4349 or KF 6008 by the company Shin-Etsu.

In particular, it may be the cetyl dimethicone copolyol.

This silicone surfactant is advantageously present in a content ranging from 0.5% to 5% by weight relative to the total weight of said composition.

Gelling Agents

Depending on the fluidity of the composition that it is desired to obtain, it is possible to incorporate one or more gelling agents into a composition of the invention.

A gelling agent suitable for the invention may be hydrophilic, i.e. soluble or dispersible in the water.

These may especially be chosen from: modified or unmodified carboxyvinyl polymers, such as the Carbopols (CTFA name: carbomer) sold by the company Goodrich; polyacrylates and polymethacrylates, such as the products sold under the names Lubrajel and Norgel by the company Guardian; polyacrylamides; polymers and copolymers of 2-acrylamido-2-methylpropanesulphonic acid, which are optionally crosslinked and/or neutralized, such as the poly (2-acrylamido-2-methylpropanesulphonic acid) sold by the company Clariant under the name Hostacerin AMPS (CTFA name: ammonium polyacryldimethyltauramide); crosslinked anionic acrylamide/AMPS copolymers, in the form of a W/O emulsion, such as those sold under the name Sepigel 305 (CTFA name: Polyacrylamide/$C_{13-14}$ Isoparaffin/Laureth-7) and under the name Simulgel 600 (CTFA name: Acrylamide/Sodium acryloyldimethyltaurate copolymer/Isohexadecane/Polysorbate 80) by the company SEPPIC; polysaccharide biopolymers, for instance xanthan gum, guar gum, carob gum, acacia gum, scleroglucans, chitin and chitosan derivatives, carrageenans, gellans, alginates, celluloses such as microcrystalline cellulose, carboxymethyl cellulose, hydroxymethyl cellulose and hydroxypropyl cellulose; and mixtures thereof.

A gelling agent suitable for the invention may be lipophilic. A lipophilic gelling agent may be inorganic or organic.

As lipophilic gelling agents, mention may, for example, be made of modified clays, such as modified magnesium silicate (Bentone gel VS38 from Rheox), hectorite modified with disteardimethylammonium chloride (CTFA name: Disteardimonium hectorite) sold under the name Bentone 38 CE by the company Rheox.

As inorganic lipophilic gelling agent, mention may be made of optionally modified clays, such as hectorites modified with a $C_{10}$ to $C_{22}$ fatty acid ammonium chloride, for instance hectorite modified with disteardimethylammonium chloride, such as, for example, that sold under the name Bentone 38V® by the company Elementis.

The polymeric organic lipophilic gelling agents are, for example, partially or completely crosslinked elastomeric organopolysiloxanes with a three-dimensional structure, such as those sold under the names KSG6®, KSG16® and KSG18® by the company Shin-Etsu, Trefil E-505C® and Trefil E-506C® by the company Dow Corning, Gransil SR-CYC®, SR DMF10, SR-DC556®, SR 5CYC Gel®, SR DMF 10 Gel® and SR DC 556 Gel® by the company Grant Industries, SF 1204® and JK 113® by the company General Electric; block copolymers of "diblock", "triblock" or "radial" type, of the polystyrene/polyisoprene or polystyrene/polybutadiene type, such as those sold under the name Luvitol HSB® by the company BASF, of the polystyrene/copoly(ethylene-propylene) type, such as those sold under the name Kraton® by the company Shell Chemical Co, or else of the polystyrene/copoly(ethylene-butylene) type, blends of triblock and radical (star) copolymers in isododecane, such as those sold by the company Penreco under the name Versagel® for instance the mixture of butylene/ethylene/styrene triblock copolymer and of ethylene/propylene/styrene star copolymer in isododecane (Versagel M 5960).

Among the lipophilic gelling agents that may be used in a cosmetic composition of the invention, mention may also be made of esters of dextrin and of a fatty acid, such as dextrin palmitates, in particular such as those sold under the name Rheopearl TL®, Rheopearl TL2-OR® or Rheopearl KL® by the company Chiba Flour.

By way of lipophilic gelling agent suitable for the invention, mention may also be made of hydrogenated plant oils, such as hydrogenated castor oil.

By way of lipophilic gelling agent also suitable for the invention, mention may be made of fatty alcohols, in particular $C_8$ to $C_{26}$ fatty alcohols, and more particularly $C_{12}$ to $C_{22}$ fatty alcohols.

According to one embodiment, a fatty alcohol suitable for the invention may be selected from mysrityl alcohol, cetyl alcohol, stearyl alcohol and behenyl alcohol By way of lipophilic gelling agent also suitable for the invention, mention may be made of fatty acid esters of glycerols, such as glyceryl stearate.

According to one embodiment, a composition of the invention may comprise at least one lipophilic gelling agent, in particular selected from modified hectorites.

Colorants

A composition according to the invention may also comprise at least one colorant, in particular a pulverulent colorant.

A cosmetic composition in accordance with the invention may advantageously Incorporate at least one colorant selected from organic or Inorganic colorants, in particular such as pigments or nacres conventionally used in cosmetic compositions, which may be fat-soluble or water-soluble, and mixtures thereof.

The term "pigments" should be understood to mean white or coloured, inorganic or organic particles which are insoluble in an aqueous solution and are intended for colouring and/or opacifying the resulting film.

The pigments may be present in a proportion of from 0.01% to 40% by weight, especially from 0.1% to 20% by weight and in particular from 1% to 15% by weight relative to the total weight of the cosmetic composition.

As inorganic pigments that can be used in the invention, mention may be made of titanium oxides, zirconium oxides or cerium oxides, and also zinc oxides, iron oxides or chromium oxides, ferric blue, manganese violet, ultramarine blue and chromium hydrate.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPPs) described in documents EP-A-542 669, EP-A-787 730, EP-A-787 731 and WO-A-96/08537.

The cosmetic composition according to the invention may also comprise water-soluble or fat-soluble dyes. The fat-soluble dyes are, for example, Sudan red, DC Red 17, DC Green 6, β-carotene, Sudan brown, DC Yellow 11, DC Violet 2, DC Orange 5 and quinoline yellow. The water-soluble dyes are, for example, beetroot juice and caramel.

According to one particular embodiment, the composition of the invention comprises at least one particular colorant chosen from goniochromatic colouring agents, photochromic colouring agents, fluorescent agents, optical brighteners, lakes, organic pigments, composite pigments, and mixtures thereof.

Goniochromatic Colouring Agents

The term "goniochromatic colouring agent" denotes, within the meaning of the present invention, a colouring agent which makes it possible to obtain, when the composition containing it is spread over a support, a colour trajectory in the a*b* plane of the CIE 1976 colorimetric space that corresponds to a variation Dh in the hue angle h of at least 20° C. when the angle of observation relative to the normal is varied between 0° and 80°, for an incident light angle of 45°.

The goniochromatic colouring agent may be chosen, for example, from multilayer interference structures and liquid-crystal colouring agents.

In the case of a multilayer structure, it may comprise, for example, at least two layers, each layer, which may or may not be independent of the other layer(s), being made, for example, from at least one material chosen from the group consisting of the following materials: $MgF_2$, $CeF_3$, $ZnS$, $ZnSe$, $Si$, $SiO_2$, $Ge$, $Te$, $Fe_2O_3$, $Pt$, $Va$, $Al_2O_3$, $MgO$, $Y_2O_3$, $S_2O_3$, $SiO$, $HfO_2$, $ZrO_2$, $CeO_2$, $Nb_2O_5$, $Ta_2O_5$, $TiO_2$, $Ag$, $Al$, $Au$, $Cu$, $Rb$, $Ti$, $Ta$, $W$, $Zn$, $MoS_2$, cryolite, and alloys, polymers and combinations thereof.

The goniochromatic agents having multilayer structures are especially those described in the following documents: U.S. Pat. No. 3,438,796, EP-A-227 423, U.S. Pat. No. 5,135,812, EP-A-170 439, EP-A-341 002, U.S. Pat. No. 4,930,866, U.S. Pat. No. 5,641,719, EP-A-472 371, EP-A-395 410, EP-A-753 545, EP-A-768 343, EP-A-571 836, EP-A-708 154, EP-A-579 091, U.S. Pat. No. 5,411,586, U.S.

Pat. No. 5,364,467, WO-A-97/39066, DE-A-4 225 031, WO 95/17479 (BASF) and DE-A-196 14 637. They are in the form of flakes, with a metallic colour.

The multilayer structures that can be used in the invention are, for example, the following structures: $Al/SiO_2/Al/SiO_2/Al$; $Cr/MgF_2/Al/MgF_2/Al$; $MoS_2/SiO_2/Al/SiO_2/MoS_2$; $Fe_2O_3/SiO_2/Al/SiO_2/Fe_2O_3$; $Fe_2O_3/SiO/Fe_2O_3/Fe_2O_3/SiO_2/Fe_2O_3$; $MoS_2/SiO_2/mica$ $oxide/SiO_2/MoS_2$; $Fe_2O_3/SiO_2/mica$ $oxide/SiO_2/Fe_2O_3$. Different colours are obtained depending on the thickness of the various layers. Thus, with the $Fe_2O_3/SiO_2/Al/SiO_2/Fe_2O_3$ structure, the colour changes from greenish gold to reddish grey for $SiO_2$ layers of 320 to 350 nm; from red to gold for $SiO_2$ layers of 380 to 400 nm; from violet to green for $SiO_2$ layers of 410 to 420 nm; from copper to red for $SiO_2$ layers of 430 to 440 nm.

As a result, the multilayer structure may be essentially inorganic or organic. Different colours are obtained depending on the thickness of each of the various layers.

The goniochromatic pigments having a multilayer interference structure are especially those described in the following documents: U.S. Pat. No. 3,438,796, EP-A-227 423, U.S. Pat. No. 5,135,812, EP-A-170 439, EP-A-341 002, U.S. Pat. No. 4,930,866, U.S. Pat. No. 5,641,719, EP-A-472 371, EP-A-395 410, EP-A-753 545, EP-A-768 343, EP-A-571 836, EP-A-708 154, EP-A-579 091, U.S. Pat. No. 5,411,586, U.S. Pat. No. 5,364,467, WO-A-97/39066, DE-A-4 225 031, WO 95/17479 (BASF), DE-A-196 14 637, and combinations thereof. They are in the form of flakes, with a metallic colour.

Preferably, the goniochromatic pigment having a multilayer interference structure according to the invention is chosen from the group formed by the following commercial goniochromatic pigments: Infinite Colors manufactured or sold by the company Shiseido, Sicopearl Fantastico manufactured or sold by the company BASF, Colorstream manufactured or sold by the company MERCK, Colorglitter manufactured or sold by the company 3M, Chromaflair manufactured or sold by the company FLEX, and Xiraollic and Xirona manufactured or sold by the company MERCK, and mixtures thereof.

As goniochromatic agents with a multilayer structure mention may be made of those sold under the name Sicopearl.

As regards the liquid crystal goniochromatic particles capable of being used in the composition according to the invention, they may in particular be based on a polymer obtainable by polymerizing a mixture of monomers comprising:

a) at least one first monomer A of formula (I) Y1-A1-M1-A2-Y2 in which:
i) Y1 and Y2, which are identical or different, represent a polymerizable group selected from acrylate or methacrylate groups, an epoxy group or an isocyanate, hydroxyl, vinyl ether (—O—CH=$CH_2$) or vinyl ester (—CO—O—CH=$CH_2$) group, and
ii) A1 and A2, which are identical or different, represent a group of formula —$CnH_2n$-, in which n is an integer ranging from 0 to 20, it being possible for one or more methylene groups of said —$CnH_2n$- group to be replaced by one or more oxygen atoms, and
iii) M1 denotes a group of general formula (I') —$R_1$—$X_1$—$R_2$—$X_2$—$R_3$—$X_3$—$R_4$—, in which $R_1$, $R_2$, $R_3$ and $R_4$, which are identical or different, denote a divalent group selected from —O—, —COO—, —CONH—, —CO—, —S—, —C≡C—, —CH=CH—, —N=N— and —N=N(O)—, it being possible for —$R_2$—$X_2$—$R_3$— or —$R_2$—$X_2$— or —$R_2$—$X_2$—$R_3$—$X_3$— also to be a single covalent bond, and $X_1$, $X_2$ and $X_3$ are identical or different groups selected from the 1,4-phenylene group, the 1,4-cyclohexylene group, arylene or heteroarylene groups having an aryl nucleus comprising from 6 to 10 atoms which are optionally substituted by B1 and/or B2 and/or B3, said heteroarylene containing from 1 to 3 heteroatoms selected from the O, N and S atoms, or cycloalkylene groups having from 3 to 10 carbon atoms which are optionally substituted by —B1 and/or —B2 and/or —B3, —B1, —B2 and —B3, which are identical or different, being selected from $C_1$-$C_{20}$ alkyl, $C_1$-$C_{20}$ alkoxy, $C_1$-$C_{20}$ alkylthio, ($C_1$-$C_2$)alkyl carbonyl, ($C_1$-$C_{20}$)alkoxy carbonyl, ($C_1$-$C_{20}$)alkyl thiocarbonyl, —OH, —F, —Cl, —Br, —I, —CN, —$NO_2$, formyl, acetyl, and alkyl, alkoxy or alkylthio groups having from 1 to 20 carbon atoms which are interrupted by one or more oxygen atom(s) or one or more sulphur atom(s) or one or more ester group(s),
and
b) at least one chiral second monomer B of formula (II) V1-A'1-W1-Z—W2-A'2-V2, in which:
i) V1 and V2, which are identical or different, denote a group selected from an acrylate or methacrylate group, an epoxy group, a vinyl ether or vinyl ester group, an isocyanate group, a $C_1$-$C_{20}$ alkyl, a $C_1$-$C_{20}$ alkoxy, a $C_1$-$C_{20}$ alkylthio, a ($C_1$-$C_{20}$)alkoxy carbonyl, a ($C_1$-$C_{20}$)alkyl thiocarbonyl, —OH, —F, —Cl, —Br, —I, —CN, —$NO_2$, formyl, acetyl and alkyl, alkoxy or alkylthio groups having from 1 to 20 carbon atoms which are interrupted by one or more oxygen atom(s) or one or more sulphur atom(s) or one or more ester (—CO—O—) group(s),
and at least V1 or V2 denotes a polymerizable group selected from acrylate or methacrylate groups, an epoxy group or an isocyanate, hydroxyl, vinyl ether (—O—CH=$CH_2$) or vinyl ester (—CO—O—CH=$CH_2$) group,
ii) A'1 and A'2, which are identical or different, represent a group of formula —$C_nH_{2n}$—, in which n is an integer ranging from 0 to 20, it being possible for one or more methylene groups of said $C_nH_{2n}$ group to be replaced by one or more oxygen atoms, and
iii) W1 and W2 denote a divalent group of general formula $R'_1$—$X'_1$—$R'_2$—$X'_2$—$R'_3$— in which $R'_1$, $R'_2$ and $R'_3$, which are identical or different, denote a divalent group selected from —O—, —COO—, —CONH—, —CO—, —S—, —C≡C—, —CH=CH—, —N=N— and —N=N(O)—, and $R'_1$, $R'_2$, $R'_3$ or $R'_2$—$X'_2$ can also be a single covalent bond, and $X'_1$ and $X'_2$ are Identical or different groups selected from the 1,4-phenylene group, the 1,4-cyclohexylene group, arylene or heteroarylene groups having an aryl nucleus comprising from 6 to 10 atoms which are optionally substituted by B'1 and/or B'2 and/or B'3, said heteroarylene containing from 1 to 3 heteroatoms selected from the O, N and S atoms, or cycloalkylene groups having from 3 to 10 carbon atoms which are optionally substituted by —B'1 and/or —B'2 and/or —B'3, —B'1, —B'2, and —B'3, which are identical or different, being selected from $C_1$-$C_{20}$ alkyl, $C_1$-$C_{20}$ alkoxy, $C_1$-$C_{20}$ alkylthio, ($C_1$-$C_{20}$)alkyl carbonyl, ($C_1$-$C_{20}$)alkoxy carbonyl, ($C_1$-$C_{20}$)alkyl thiocarbonyl, —OH, —F, —Cl, —Br, —I, —CN, —$NO_2$, formyl, acetyl, and alkyl, alkoxy or alkylthio groups having from 1 to 20 carbon atoms which are interrupted by one or more oxygen atom(s) or one or more sulphur atom(s) or one or more ester group(s), and Z denotes a chiral divalent group comprising at least 4 carbon atoms, in particular from 4 to 20 carbon atoms and more preferably from 4 to 10 carbon atoms (the chiral divalent group comprising at least one asymmetric carbon, especially one or two asymmetric carbons and in particular two asymmetric carbons), and in particular a chiral divalent group originating from the group of the dianhydrohexites, hexoses, pentoses, binaphthyl derivatives (binaphthyl groups), biphenyl derivatives (biphenyl groups), tartaric acid derivatives or glycols which are optically active.

Preferably, the particles of liquid crystal polymer have a larger size ranging from 1 μm to 3 mm, and preferably ranging from 30 μm to 500 μm. These particles are advantageously in the form of flakes.

Such polymers and their particles are disclosed in application EP-A-1 046 692.

Use may be made in particular, as particles of liquid crystal polymer, of those known under the CTFA name Polyacrylate-4 and sold under the names Helicone® HC Sapphire, Helicone® HC Scarabeus, Helicone® HC Jade, Helicone® HC Maple, Helicone® HC XL Sapphire, Helicone® HC XL Scarabeus, Helicone® HC XL Jade and Helicone® HC XL Maple by Wacker.

Photochromic Colouring Agents

A photochromic colouring agent is an agent which has the property of changing colour when it is lit by ultraviolet light and of regaining its initial colour when it is no longer lit by this light, or else of passing from an uncoloured state to a coloured state, and vice versa. In particular this agent exhibits different colours depending on whether it is lit with natural light or artificial light.

The photochromic agents that can be used in the invention are, in particular, those described in documents JP-A-09/165532, EP-A-709 728, JP-A-07/258580, JP-A-07/223816, EP-A-624 553, JP-A-08/337422, JP-A-07/025617 and EP-A-359 909.

More specifically the photochromic colouring agents that can be used in the invention are spirooxazines and derivatives thereof such as spiroindolinonaphthooxazines, spironaphthoxazines, naphthopyran and its derivatives, spiropyrans, such as indolinospirobenzopyrans, nitrobenzylpyridines, spirolans, titanium oxide or zinc oxide doped with iron. By way of example mention may be made of photochromic agents of the type derived from naphthopyran, sold by the company PPG under the references Photosol 5-68 Photochromic Dye, Photosol 7-49 Photochromic Dye, Photosol 7-106 Photochromic Dye, Photosol 0265 Photochromic Dye, Photosol 0272 Photochromic Dye, these agents exhibiting two different colours depending on whether they are excited or not by UV rays. Use may also be made of doped aluminosilicates, doped in particular with the groups S, Se, $SO_4^{2-}$, $WO_4^{2-}$ or OH, or else with metal ions, especially Fe, Cr, Mn, Co or Ni ions, such as those described in application EP-A-847 751.

Fluorescent Agents (or Substances)

Fluorescent agents are well known to those skilled in the art. They may be pigments or dyes. The term "pigments" is understood to mean inorganic or organic particles that are insoluble in the composition. The term "dye" is understood to mean chemical compounds dissolved in the composition. The dyes may be water-soluble or fat-soluble. Fluorescent substances are, for example, described in "Luminescent materials (fluorescent daylight)", Encyclopedia of Chemical Technology, Kirk-Othmer, vol. 14, pp. 546-569, 3rd edition, 1981, Wiley.

For the purposes of the present invention a fluorescent agent is a substance which, under the effect of ultraviolet rays and/or of visible light, re-emits in the visible range the portion of light which it has absorbed under the same colour as that which it reflects naturally. The naturally reflected colour is thus reinforced by the re-emitted colour and appears extremely bright.

As fluorescent agent use may be made of inorganic fluorescent substances such as those described in application JP 05-117127 and, in particular, inorganic fluorescent substances based on zinc oxide.

As fluorescent agents it is also possible to use organic fluorescent substances such as daylight-fluorescent pigments; these pigments are generally manufactured from fluorescent dyes, which are dissolved beforehand in a support resin to give a solid solution, which is subsequently ground to a powder of resin particles exhibiting fluorescent properties. The preparation of such fluorescent pigments is described in EP 0 370 470, U.S. Pat. No. 2,851,424, U.S. Pat. No. 3,711,604, U.S. Pat. No. 3,856,550 and U.S. Pat. No. 2,938,878.

Fluorescent pigments particularly suitable for the present invention may thus be selected from coloured polyamide and/or formaldehyde/benzoguanamine and/or melamine/formaldehyde/sulphonamide resins, from coloured aminotriazine/formaldehyde/sulphonamide co-condensates and/or from metallized polyester flakes and/or mixtures thereof. These fluorescent pigments may also be present in the form of aqueous dispersions of fluorescent pigments.

As fluorescent pigments particularly suitable for the present invention mention may be made of the pink-coloured fluorescent aminotriazine/formaldehyde/sulphonamide co-condensate with a mean particle size of 3-4 microns sold under the trade name Fiesta Astral Pink FEX-1 and the blue-coloured fluorescent aminotriazine/formaldehyde/sulphonamide co-condensate with a mean particle size of 3-4.5 microns sold under the trade name Fiesta Comet Blue FTX-60 by the company Swada, or alternatively the yellow-coloured benzoguanamine/formaldehyde resin covered with formaldehyde/urea resin sold under the trade name FB-205 Yellow and the red-coloured benzoguanamine/formaldehyde resin covered with formaldehyde/urea resin sold under the trade name FB-400 Orange Red by the company UK Seung Chemical, and the orange-coloured polyamide resin sold under the trade name Flare 911 Orange 4 by the company Sterling Industrial Colors.

Optical Brighteners

The fluorescent agents may also be selected from optical brighteners, which are white organic fluorescent substances.

Optical brighteners are compounds that are well known to those skilled in the art. Such compounds are described in "Fluorescent Whitening Agent, Encyclopedia of Chemical Technology, Kirk-Othmer", vol. 11, pp. 227-241, 4th Edition, 1994, Wiley.

They may be defined more particularly as compounds that absorb essentially in the UVA range between 300 and 390 nm and re-emit essentially between 400 and 525 nm.

Their lightening effect resides more particularly in an emission of energy of between 400 and 480 nm, which corresponds to an emission in the blue part of the visible region, which contributes to lightening the skin visually when this emission takes place on the skin.

Optical brighteners that are especially known include stilbene derivatives, in particular polystyrylstilbenes and triazinylstilbenes, coumarin derivatives, in particular hydroxycoumarins and aminocoumarins, oxazole, benzoxazole, imidazole, triazole and pyrazoline derivatives, pyrene derivatives, porphyrin derivatives and mixtures thereof.

Such compounds are widespread in commerce. They include in particular the following derivatives:

the stilbene derivative of naphthotriazole, sold under the trade name Tinopal GS, the disodium 4,4'-distyrylbiphenylsulphonate (CTFA name: disodium distyrylbiphenyl disulphonate) sold under the trade name Tinopal CBS-X, the cationic aminocoumarin derivative sold under the trade name Tinopal SWN CONC., the sodium 4,4'-bis[(4,6 dianilino-1,3,5-triazin-2-yl)amino]stilbene-2,2'-disulphonate sold under the trade name Tinopal SOP, the 4,4'-bis[(4-anilino-6-bis(2-hydroxyethyl)amino-1,3,5-triazin-2-yl)amino]stilbene-2,2'-disulphonic acid sold under the trade name Tinopal UNPA-GX, the 4,4'-bis[(anilino-6-morpholine-1,3,5-triazin-2-yl)amino]stilbene sold under the trade name Tinopal AMS-GX, and the disodium 4,4'-bis[(4-anilino-6-(2-hydroxyethyl)methylamino-1,3,5-triazin-2-yl)amino]stilbene-2,2'-sulphonate sold under the trade name Tinopal 5BM-GX, all by the company CIBA Specialty Chemicals;

the 2,5-thiophenediylbis(5-tert-butyl-1,3-benzoxazole) sold under the trade name Uvitex OB by the company CIBA;

the anionic derivative of diaminostilbene in dispersion in water, sold under the trade name Leucophor BSB liquide by the company Clariant; and mixtures thereof.

The optical brighteners that can be used in the present invention may also be in the form of copolymers, for example of acrylates and/or methacrylates, grafted with optical brightener groups as described in application FR 99/10942.

Organic Lakes

The organic lakes may be chosen, in a known manner, from insoluble sodium, potassium, calcium, barium, aluminium, zirconium, strontium or titanium salts of acidic dyes such as azo, anthraquinone, indigoid, xanthene, pyrene, quinoline, triphenylmethane or fluorane dyes. These dyes generally comprise at least one carboxylic or sulphonic acid group.

The organic lakes may also be supported by any compatible support such as a mineral support, for instance particles of alumina, of clay, of zirconia or of metal oxides, in particular of zinc oxide or of titanium oxide, of talc, of calcium carbonate or of barium sulphate. Preferably, the mineral support is chosen from alumina, titanium oxide and barium sulphate.

Among the organic lakes, mention may in particular be made of those known under the following names: D&C Red No. 2 Aluminium lake, D&C Red No. 3 Aluminium lake, D&C Red No. 4 Aluminium lake, D&C Red No. 6 Aluminium lake, D&C Red No. 6 Barium lake, D&C Red No. 6 Barium/Strontium lake, D&C Red No. 6 Strontium lake, D&C Red No. 6 Potassium lake, D&C Red No. 7 Aluminium lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminium lake, D&C Red No. 9 Barium lake, D&C Red No. 9 Barium/Strontium lake, D&C Red No. 9 Zirconium lake, D&C Red No. 10 Sodium lake, D&C Red No. 19 Aluminium lake, D&C Red No. 19 Barium lake, D&C Red No. 19 Zirconium lake, D&C Red No. 21 Aluminium lake, D&C Red No. 21 Zirconium lake, D&C Red No. 22 Aluminium lake, D&C Red No. 27 Aluminium lake, D&C Red No. 27 Aluminium/Titanium/Zirconium lake, D&C Red No. 27 Barium lake, D&C Red No. 27 Calcium lake, D&C Red No. 27 Zirconium lake, D&C Red No. 28 Aluminium lake, D&C Red No. 30 lake, D&C Red No. 31 Calcium lake, D&C Red No. 33 Aluminium lake, D&C Red No. 34 Calcium lake, D&C Red No. 36 lake, D&C Red No. 40 Aluminium lake, D&C Blue No. 1 Aluminium lake, D&C Green No. 3 Aluminium lake, D&C Orange No. 4 Aluminium lake, D&C Orange No. 5 Aluminium lake, D&C Orange No. 5 Zirconium lake, D&C Orange No. 10 Aluminium lake, D&C Orange No. 17 Barium lake, D&C Yellow No. 5 Aluminium lake, D&C Yellow No. 5 Zirconium lake, D&C Yellow No. 6 Aluminium lake, D&C Yellow No. 7 Zirconium lake, D&C Yellow No. 10 Aluminium lake, FD&C Blue No. 1 Aluminium lake, FD&C Red No. 4 Aluminium lake, FD&C Red No. 40 Aluminium lake, FD&C Yellow No. 5 Aluminium lake, FD&C Yellow No. 6 Aluminium lake, and mixtures thereof.

The chemical compounds corresponding to each of the organic pigments cited previously are mentioned in the publication "International Cosmetic Ingredient Dictionary and Handbook", 1997 edition, pages 371 to 386 and 524 to 528, published by "The Cosmetic, Toiletry and Fragrance Association", the content of which is incorporated into the present application by way of reference.

Organic Pigments

Mention may especially be made of the organic pigments of azo dyes, anthraquinone dyes, indigoid dyes, xanthene dyes, pyrene dyes, quinoline dyes, triphenylmethane dyes and fluorane dyes.

Among the organic pigments that may especially be mentioned are those known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6, D&C Black 2 (carbon black) and phthalocyanine blue, and mixtures thereof.

Composite Pigments

According to one particularly preferred embodiment, the composition of the invention contains, as particular colorant associated with the bismuth oxychloride dispersed in at least one specific oil as defined above, at least one composite pigment as described below.

Structure

A composite pigment according to the invention may be composed, in particular, of particles comprising:
    an inorganic core,
    at least one, at least partial, coating of at least one organic colorant.

At least one binder may advantageously contribute to the attachment of the organic colorant to the inorganic core. This binder may advantageously act without the formation of covalent bonds.

The composite pigment particles may have varied forms. These particles may especially be in platelet or globular, in particular spherical, form and may be hollow or solid. The term "in platelet form" denotes particles having a ratio of the largest dimension to the thickness of greater than or equal to 5.

A composite pigment according to the invention can, for example, have a specific surface area of between 1 and 1000 m²/g, especially between 10 and 600 m²/g approximately and in particular between 20 and 400 m²/g approximately. The specific surface area is the value measured by the BET method.

Inorganic Core

The inorganic core can be of any form suitable for the attachment of particles of organic colorant, for example spherical, globular, granular, polyhedral, acicular, spindle-shaped, flattened in the fleck, rice grain or flake form, and a combination of these forms, this list not being limiting.

Preferably, the ratio of the largest dimension of the core to its smallest dimension is between 1 and 50.

The inorganic core may have an average size of between approximately 5 nm and approximately 100 nm, or even between approximately 5 nm and approximately 75 nm, for example between approximately 10 nm and approximately 50 nm, especially around 20 or 25 nm.

The term "average size" denotes the dimension given by statistical particle size distribution for half the population, referred to as D50. The average size may be a number-average size determined by image analysis (electron microscopy).

The inorganic core may be made of a material chosen from the non-limiting list comprising metal salts and metal oxides, in particular titanium, zirconium, cerium, zinc, iron, ferric blue, aluminium and chromium oxides, aluminas, glasses, ceramics, graphite, silicas, silicates, in particular aluminosilicates and borosilicates, synthetic mica, and mixtures thereof.

In particular, the inorganic core of said composite pigment comprises a metal oxide chosen from a titanium, zirconium, cerium, zinc, iron, ferric blue, chromium and aluminium oxide, in particular a titanium oxide.

According to one particular embodiment of the invention, the inorganic core is a titanium oxide.

Titanium oxides, especially $TiO_2$, iron oxides, especially $Fe_2O_3$, cerium oxides, zinc oxides, aluminium oxides or silicates, especially aluminosilicates and borosilicates, are very particularly suitable.

The inorganic core may have a specific surface area, measured by the BET method, of, for example, between approximately 1 m²/g and approximately 1000 m²/g, better still between approximately 10 m²/g and approximately 600 m²/g, for example between approximately 20 m²/g and approximately 400 m²/g.

The specific surface area is for example between 30 and 70 m²/g, for example close to 50 m²/g, in particular in the case of $TiO_2$ cores having a size close to 20 or 25 nm.

The inorganic core can be coloured, if appropriate.

The refractive index of the inorganic core is advantageously greater than or equal to 2, or even greater than or equal to 2.1 or 2.2.

The weight proportion of the inorganic core within the composite pigment may exceed 50%, being, for example, between 50% and 70%, or 50% and 60%.

Organic Colorant

The organic colorant may be chosen, for example, from particulate compounds that are insoluble in the physiologically acceptable medium of the composition.

The organic colorant may comprise, for example, organic pigments that may be chosen from the compounds below, and mixtures thereof:

cochineal carmine, organic pigments of azo, anthraquinone, indigoid, xanthene, pyrene, quinoline, triphenylmethane or fluorane dyes, organic lakes or insoluble organic sodium, potassium, calcium, barium, aluminium, zirconium, strontium or titanium salts of acidic dyes such as azo, anthraquinone, indigoid, xanthene, pyrene, quinoline, triphenylmethane or fluorane dyes, these dyes possibly comprising at least one carboxylic or sulphonic acid group.

Among the organic pigments that may especially be mentioned are those known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6, D&C Black 2 (carbon black) and phthalocyanine blue, and mixtures thereof.

According to one particular embodiment, use is made of the organic pigment D&C Red No. 7.

According to another embodiment, use is made of the organic pigment D&C Red No. 28.

According to another particular embodiment, use is made of the organic pigment FD&C Yellow No. 5.

The organic colorant may comprise an organic lake supported on an organic support such as rosin or aluminium benzoate, for example.

Among the organic lakes that may be mentioned in particular are those known under the following names: D&C Red No. 2 Aluminium lake, D&C Red No. 3 Aluminium lake, D&C Red No. 4 Aluminium lake, D&C Red No. 6 Aluminium lake, D&C Red No. 6 Barium lake, D&C Red No. 6 Barium/Strontium lake, D&C Red No. 6 Strontium lake, D&C Red No. 6 Potassium lake, D&C Red No. 7 Aluminium lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminium lake, D&C Red No. 9 Barium lake, D&C Red No. 9 Barium/Strontium lake, D&C Red No. 9 Zirconium lake, D&C Red No. 10 Sodium lake, D&C Red No. 19 Aluminium lake, D&C Red No. 19 Barium lake, D&C Red No. 19 Zirconium lake, D&C Red No. 21 Aluminium lake, D&C Red No. 21 Zirconium lake, D&C Red No. 22 Aluminium lake, D&C Red No. 27 Aluminium lake, D&C Red No. 27 Aluminium/Titanium/Zirconium lake, D&C Red No. 27 Barium lake, D&C Red No. 27 Calcium lake, D&C Red No. 27 Zirconium lake, D&C Red No. 28 Aluminium lake, D&C Red No. 30 lake, D&C Red No. 31 Calcium lake, D&C Red No. 33 Aluminium lake, D&C Red No. 34 Calcium lake, D&C Red No. 36 lake, D&C Red No. 40 Aluminium lake, D&C Blue No. 1 Aluminium lake, D&C Green No. 3 Aluminium lake, D&C Orange No. 4 Aluminium lake, D&C Orange No. 5 Aluminium lake, D&C Orange No. 5 Zirconium lake, D&C Orange No. 10 Aluminium lake, D&C Orange No. 17 Barium lake, D&C Yellow No. 5 Aluminium lake, D&C Yellow No. 5 Zirconium lake, D&C Yellow No. 6 Aluminium lake, D&C Yellow No. 7 Zirconium lake, D&C Yellow No. 10 Aluminium lake, FD&C Blue No. 1 Aluminium lake, FD&C Red No. 4 Aluminium lake, FD&C Red No. 40 Aluminium lake, FD&C Yellow No. 5 Aluminium lake, FD&C Yellow No. 6 Aluminium lake, and mixtures thereof.

According to one particular embodiment, use is made of the organic lake FD&C Blue No. 1 Aluminium lake or D&C Blue No. 1 Aluminium lake.

According to another particular embodiment, use is made of the organic lake D&C Red No. 28 Aluminium lake.

According to another embodiment, use is made of the organic lake FD&C Yellow No. 5 Aluminium lake.

The chemical compounds corresponding to each of the organic colorants cited previously are mentioned in the publication "International Cosmetic Ingredient Dictionary and Handbook", 1997 edition, pages 371 to 386 and 524 to 528, published by The Cosmetic, Toiletry and Fragrance Association, the content of which is incorporated into the present patent application by reference.

The weight proportion of organic colorant may be between around 10 parts and around 500 parts by weight per 100 parts of the inorganic core, or even between around parts and around 250 parts by weight, for example between around 40 parts and around 125 parts by weight per 100 parts of the inorganic core.

In certain exemplary embodiments, the total organic colorant content of the composition is less than or equal to 10% by weight relative to the total weight of the composition.

The organic colorant represents, for example, between 30% and 50% by weight of the composite pigment relative to the total weight thereof, for example between 30% and 40%.

Binder

The binder may be of any type, provided that it allows the organic colorant to adhere to the surface of the inorganic core.

According to one particular and preferred embodiment, the binder is organic.

The binder may especially be chosen from a non-limiting list comprising silicone compounds, polymeric, oligomeric or similar compounds, and in particular from organosilanes, fluoroalkylated organosilanes and polysiloxanes, for example polymethylhydrosiloxane, and various coupling agents, such as coupling agents based on silanes, on titanates, on aluminates or on zirconates, and mixtures thereof.

Preferably, the organic binder is chosen from silicone compounds.

The silicone compound may be chosen from a non-limiting list comprising in particular:

organosilanes (1) obtained from alkoxysilanes,
modified or unmodified polysiloxanes (2) chosen from a non-limiting list comprising:
modified polysiloxanes (2A) comprising at least one radical chosen from, in particular, polyethers, polyesters and epoxy compounds (they will be referred to as "modified polysiloxanes"),
polysiloxanes (2B) bearing, on a silicon atom located at the end of the polymer, at least one group chosen from a non-limiting list comprising carboxylic acids, alcohols or hydroxyl groups, and
fluoroalkylated organosilane compounds (3) obtained from fluoroalkylsilanes.

The organosilane compounds (1) may be obtained from alkoxysilane compounds represented by the formula (I):

$$R^1{}_a Si X_{4-a} \qquad (I)$$

in which:
$R^1$ represents $C_6H_5-$, $(CH_3)_2CH-CH_2-$ or a radical of $C_bH_{2b+1}-$ type (where b varies from 1 to 18), X represents $CH_3O-$ or $C_2H_5O-$, and
a varies from 0 to 3.

Specific examples of alkoxysilane compounds may include the alkoxysilanes chosen from: methyltriethoxysilane, dimethyldiethoxysilane, phenyltriethyoxysilane, diphenyldiethoxysilane, methyltrimethoxysilane, dimethyldimethoxysilane, phenyl-trimethoxysilane, diphenyldimethoxysilane, isobutyltrimethoxysilane, decyltrimethoxysilane and the like, in particular from methyltriethoxysilane, phenyltriethoxysilane, methyltrimethoxysilane, dimethyldimethoxysilane, isobutyltrimethoxysilane, and better still methyltriethoxysilane, methyltrimethoxysilane and phenyltriethoxysilane.

The polysiloxanes (2) may especially correspond to the formula (II):

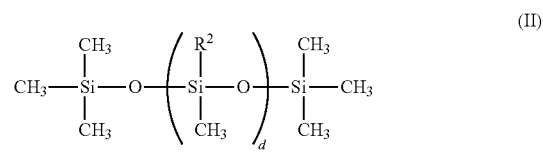

in which $R^2$ represents $H-$ or $CH_3-$ and d varies from 15 to 450.

Among these polysiloxanes, those for which $R^2$ represents H are preferred.

The modified polysiloxanes (2A) may especially correspond to the following formulae:
($a^1$) modified polysiloxanes bearing polyethers, represented by formula (III):

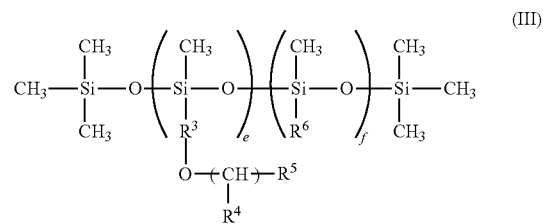

in which $R^3$ represents $-(CH_2)_h-$; $R^4$ represents $-(CH_2)_i-CH_3$; $R^5$ represents $-OH$, $-COOH$, $-CH=CH_2$, $-C(CH_3)=CH_2$ or $-(CH_2)-CH_3$; Re represents $-(CH_2)_k-CH_3$; g and h varying independently from 1 to 15; j and k varying independently from 0 to 15; e varying from 1 to 50 and f varying from 1 to 300.

($a^2$) modified polysiloxanes bearing polyesters, represented by formula (IV):

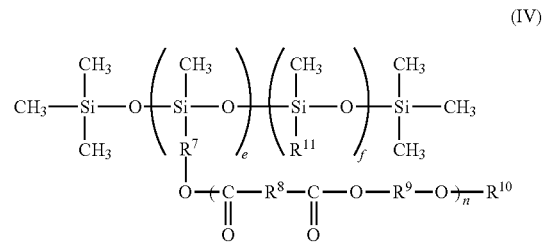

in which $R^7$, $R^8$ and $R^9$ independently represent $-(CH_2)_q-$; $R^{10}$ represents $-OH$; $-COOH$, $-CH=CH_2$, —C(CH$_3$)=CH$_2$ or —(CH$_2$)$_r$—CH$_3$; R$^{11}$ represents —(CH$_2$)$_s$—CH$_3$; n and q varying independently from 1 to 15, r and s varying independently from 0 to 15; e varying from 1 to 50 and f varying from 1 to 300, (a$^3$) modified polysiloxanes bearing epoxy radicals represented by formula (V):

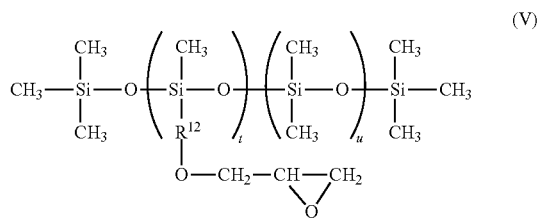

in which R$^{12}$ represents —(CH$_2$)$_v$—; v varying from 1 to 15; t varying from 1 to 50 and u varying from 1 to 300; or mixtures thereof.

Among the modified polysiloxanes (2A), the modified polysiloxanes bearing polyethers of formula (III) are preferred.

The polysiloxanes modified on the terminal part (2B) may correspond to formula (VI):

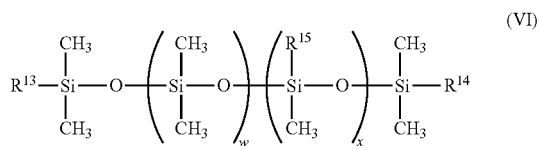

in which R$^{13}$ and R$^{14}$ may represent —OH, R$^{16}$—OH or R$^{17}$—COOH, independently of one another; R$^{15}$ represents —CH$_3$ or —C$_6$H$_5$; R$^{16}$ and R$^{17}$ represent —(CH$_2$)$_y$—; y varying from 1 to 15; w varying from 1 to 200 and x varying from 0 to 100.

Among these polysiloxanes modified at at least one end, those bearing at least radical (R$^{16}$ and/or R$^{17}$) bearing a carboxylic acid group on at least one terminal silicon atom are more preferred.

The fluoroalkylated organosilane compounds (3) may be obtained from fluoroalkylsilanes represented by formula (VII):

CF$_3$(CF$_2$)$_z$CH$_2$CH$_2$(R$^{18}$)$_a$SiX$_{4-a}$ (VII)

in which:
R$^{18}$ represents CH$_3$—, C$_2$H$_5$—, CH$_3$O— or C$_2$H$_5$O—,
X represents CH$_3$O— or C$_2$H$_5$O—,
Z varies from 0 to 15 and a varies from 0 to 3.

The fluoroalkylsilanes may especially be chosen from a non-limiting list comprising, in particular, trifluoropropyltrimethoxysilane, tridecafluorooctyltrimethoxysilane, heptadecafluorodecyltrimethoxysilane, heptadecafluorodecylmethyldimethoxysilane, trifluoropropyltriethoxysilane, tridecafluorooctyltriethoxysilane, heptadecafluorodecyl-triethoxysilane, heptadecafluorodecylmethyldiethoxysilane and the like, in particular trifluoropropyltrimethoxysilane, tridecafluorooctyltrimethoxysilane and heptadecafluorodecyltrimethoxysilane, and better still trifluoropropyltrimethoxysilane and tridecafluorooctyltrimethoxysilane.

The silane-based coupling agents may be chosen from a non-limiting list especially comprising vinyltrimethoxysilane, vinyltriethoxysilane, γ-aminopropyltriethoxysilane, γ-glycidoxypropyltrimethoxysilane, γ-mercaptopropyltrimethoxysilane, γ-methacryloxy-propyltrimethoxysilane, N-β-(aminoethyl)-γ-aminopropyltrimethoxysilane, γ-glycidoxy-propylmethyldimethoxysilane and γ-chloropropyltrimethoxysilane, and the like.

The titanate-based coupling agents may be chosen from the list comprising isopropylstearoyl titanate, isopropyltris(dioctylpyrophosphate) titanate, isopropyltris(N-aminoethylaminoethyl) titanate, tetraoctylbis(ditridecylphosphate) titanate, tetrakis(2,2-diaryloxymethyl-1-butyl)bis(ditridecyl)phosphate titanate, bis(dioctylpyrophosphate)oxyacetate titanate and bis(dioctylpyrophosphate)ethylene titanate, and the like.

The aluminate-based coupling agents may be chosen from acetoalkoxyaluminium diisopropylate, aluminium diisopropoxymonoethylacetoacetate, aluminium tris(ethylacetoacetate) and aluminium tris(acetylacetonate), and the like.

The zirconate-based coupling agents may be chosen from a list especially comprising zirconium tetrakis(acetylacetonate), zirconium dibutoxybis(acetylacetonate), zirconium tetrakis(ethylacetoacetate), zirconium tributoxymonoethylacetoacetate and zirconium tributoxyacetylacetonate, and the like.

The compounds used as binder may especially have a molar mass that may range between 300 and 100 000.

In order to obtain a layer that covers the inorganic cores uniformly, the binder is preferably in a form that is liquid or soluble in water or in various solvents.

According to one particular embodiment, the organic binder is a polymethylhydrosiloxane.

The amount of binder may range from 0.01% to 15%, especially from 0.02% to 12.5% and in particular from 0.03% to 10% by weight (calculated relative to C or Si) relative to the weight of the particles comprising the core and the binder. For further details regarding the way of calculating the relative amount of the binder, reference may be made to patent application EP 1 184 426 A2.

The relative weight proportion of binder may be less than or equal to 5%, or even to 3%, relative to the total weight of the composite pigment.

Preparation of the Composite Pigment

The composite pigment may be prepared by any suitable process, for example a mechanicochemical process or a solution precipitation process, with dissolution of an organic colorant substance and precipitation at its surface of the core.

The composite pigment may be made, for example, via one of the processes described in European patent applications EP 1 184 426 and EP 1 217 046, the contents of which are incorporated herein by reference, advantageously via the process described in patent application EP 1 184 426.

In one exemplary embodiment, the particles intended to form the inorganic core are first of all mixed with the binder.

So that the binder adheres uniformly to the surface of the inorganic core, it is preferable to first pass these particles into a mill in order to break them up.

The mixing and stirring conditions are chosen so that the core is uniformly covered with binder. These conditions may be controlled so that the linear load is between 19.6 and 19 160 N/cm, in particular between 98 and 14 170 N/cm and better still between 147 and 980 N/cm; the treatment time is especially between 5 min and 24 hours and better still from 10 min to 20 hours; the rotational speed may be between 2 and 1000 rpm, in particular between 5 and 1000 rpm and better still between 10 and 800 rpm.

After the binder has covered the inorganic core, the organic colorant is added and mixed, with stirring, in order to adhere to the layer of binder.

The methods of addition may be, for example, an addition in large amount, continuously or in small amount.

The mixing and the stirring, whether of the inorganic cores with the binder or of the organic colorant with the binder-covered inorganic cores, may be carried out using a machine that makes it possible to apply a spatular and/or compressive shearing force to the powder mixture. Such machines are, for example, gear mixers, blade mixers, and the like. Gear mixers are very particularly suitable. A list of machines that may be suitable is given in patent application EP 1 184 426 A2.

Another method of manufacturing a composite pigment is described in patent JP 3286463, which discloses a solution precipitation process.

The organic colorant is dissolved in ethanol, the inorganic cores are then dispersed in this ethanolic solution.

Next, added slowly to these mixtures is an alkaline aqueous solution of sodium or potassium carbonate, then lastly, an ethanolic solution of calcium chloride is slowly added, the whole process being carried out with stirring.

According to one particular embodiment, the composite pigment is chosen from composite pigments comprising:
an inorganic core comprising a titanium oxide,
advantageously a silicone binder, and
at least one, at least partial, coating of at least one organic colorant chosen from lakes.

As examples of composite pigments that can be used according to the invention, alone or as a mixture, mention may especially be made of:
titanium dioxide (CI177891), blue lake FD&C Blue Aluminium lake (CI42090) and polymethylhydrosiloxane (58.1/40.7/1.2);
titanium dioxide (CI177891), D&C Red No. 7 (CI15850) and polymethylhydrosiloxane (65.8/32.9/1.3);
titanium dioxide (C177891), D&C Red No. 28 (CI145410) and polymethylhydrosiloxane (65.8/32.9/1.3);
titanium dioxide (CI177891), yellow lake FD&C Yellow 5 Aluminium lake (CI191140) and polymethylhydrosiloxane (65.8/32.9/1.3);
titanium dioxide (CI177891), D&C Red No. 7 and D&C Red No. 28 Aluminium lake (CI15850 and CI145410) and polymethylhydrosiloxane.

According to one particular embodiment, the composite pigment is chosen from composite pigments comprising:
an inorganic core comprising a titanium oxide,
advantageously a silicone binder, and
at least one, at least partial, coating of at least one organic colorant chosen from lakes, in particular those with the name D&C Blue No. 1 Aluminium lake, FD&C Blue No. 1 Aluminium lake, FD&C Red No. 4 Aluminium lake, FD&C Red No. 40 Aluminium lake, Red No. 28 Aluminium lake, or organic pigments, in particular those with the name D&C Red No. 7, D&C Red No. 28, and mixtures thereof.

According to one preferred embodiment, the composition according to the invention comprises a composite pigment. By way of example, use is made of the composite pigment comprising titanium dioxide (CI177891), blue lake FD&C Blue Aluminium lake (CI42090) and polymethylhydrosiloxane (58.1/40.7/1.2).

According to one particularly preferred embodiment, the composition of the invention comprises, in a physiologically acceptable medium:

at least two composite pigments that are different due to the nature of the organic colorant of the coating, and
at least bismuth oxychloride dispersed in at least one oil chosen from monoesters of formula $R_1COOR_2$ in which $R_1$ represents a linear or branched hydrocarbon-based chain comprising from 4 to 40 carbon atoms, preferably from 4 to 30 carbon atoms, and preferentially from 7 to 20 carbon atoms, and $R_2$ represents a branched hydrocarbon-based chain containing from 3 to 40 carbon atoms, preferably from 10 to 30 carbon atoms, and preferentially from 16 to 26 carbon atoms; and polar oils whose solubility parameter at 25° C., δa, is greater than 6 $(J/cm^3)^{1/2}$.

Advantageously, the two composite pigments comprise organic colorants having different colours respectively in order to provide the skin with a multiple colour effect.

In particular, said composition comprises:
(i) at least one first composite pigment comprising titanium dioxide, a blue lake, and advantageously a silicone binder, and
(ii) at least one second composite pigment comprising titanium dioxide, a red organic pigment and a red organic lake, and advantageously a silicone binder, and
(iii) at least bismuth oxychloride dispersed in at least one oil as defined previously, in particular 2-ethylhexyl hydroxystearate.

According to one preferred embodiment, use is made of a first titanium oxide/Blue No. 1 Aluminium lake composite pigment and a second titanium oxide/Red No. 28 Aluminium lake and D&C Red No. 7 composite pigment.

This particular combination of composite pigments makes it possible to impart a natural and fresh radiance with a natural colour effect to the skin on which the composition of the invention is applied, in addition to the light effect provided by the pre-dispersion of bismuth oxychloride described previously.

The particular colorant(s) described previously, chosen from goniochromatic colouring agents, photochromic colouring agents, fluorescent agents, optical brighteners, lakes, organic pigments, composite pigments, and mixtures thereof, is (are) present in said composition in a content ranging from 0.001% to 3%, preferably from 0.05% to 2% by weight relative to the total weight of said composition.

Advantageously, for a raw material content of a mixture of bismuth oxychloride and of an oil as defined previously, and in particular of 2-ethylhexyl hydroxystearate, ranging from 0.01% to 8% by weight of raw material, relative to the total weight of said composition, use will be made of a content of a particular colorant, and in particular of composite pigment(s), ranging from 0.001% to 2%, preferentially from 0.01% to 1% by weight relative to the total weight of said composition.

According to another embodiment, for a raw material content of a mixture of bismuth oxychloride and of an oil as defined previously, and in particular of 2-ethylhexyl hydroxystearate, ranging from 8% to 15% by weight of raw material, relative to the total weight of said composition, use will be made of a content of a particular colorant, and in particular of composite pigment(s), ranging from 0.1% to 3%, preferentially from 0.5% to 2.5% by weight relative to the total weight of said composition.

In particular, the weight ratio (A)/(B) between (A) the mixture of bismuth oxychloride and of oil as defined previously and (B) the material with an optical effect, will be greater than or equal to 1, in particular will range from 2 to 15 000, especially from 3 to 500, in particular from 5 to 100, or even from 10 to 50, and better still from 15 to 30.

Advantageously, the composition will also be able to comprise at least one additional colorant and/or reflective material, different from the particular colorant described previously, and bismuth oxychloride dispersed in a specific oil.

The term "reflective materials" denotes, within the meaning of the present invention, particles whose size, structure, especially the thickness of the layer(s) of which they are constituted and their physical and chemical natures, and the surface appearance, enable them to reflect incident light with a sufficient intensity to be able to create at the surface of the composition claimed, when the latter is applied to the support to be made up, points of brightness that are visible to the naked eye, i.e. more luminous points that contrast with their surroundings by appearing to shine.

The reflective particles may disrupt the visual perception of the curvature of the made-up support, by tending to prevent lasting visual focusing, the points of brightness being liable to appear or disappear at random when the made-up support and the observer are moving.

Said additional colorant may be chosen from organic or inorganic colorants, especially such as the inorganic pigments or nacres conventionally used in cosmetic compositions, particles with metallic glints, fat-soluble or water-soluble dyes, and mixtures thereof.

The additional reflective material may be chosen from particles with a metallic glint.

Needless to say, a person skilled in the art will adjust the choice of the additional colorants and/or reflective materials and the respective contents thereof as a function of the desired effect without adversely affecting the luminous effect and the radiance provided by the combination described above.

These additional colorants and/or reflective materials, when they are present, are in a content ranging from 0.01% to 30% by weight, preferably from 0.1% to 20% by weight, and especially from 1% to 10% by weight, relative to the total weight of said composition.

The term "pigments" should be understood to mean white or coloured, inorganic or organic particles which are insoluble in an aqueous solution and are intended for colouring and/or opacifying the resulting film.

As inorganic pigments that can be used in the invention, mention may be made of titanium oxides, zirconium oxides or cerium oxides, and also zinc oxides, iron oxides or chromium oxides, ferric blue, manganese violet, ultramarine blue and chromium hydrate.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30. Mention may also be made of the structures of pigments of $BaSO_4/TiO_2/FeSO_3$ type under the reference SILSEEM from Nihon Koken and of silica/iron oxide type XIRONA Le Rouge from Merck.

The colorant may also comprise a pigment having a structure which may be, for example, of the type such as silica microspheres containing iron oxide. An example of a pigment having this structure is the product sold by the company Miyoshi under the reference PC Ball PC-LL-100 P, this pigment being constituted of silica microspheres containing yellow iron oxide.

The term "nacres" should be understood as meaning iridescent or non-iridescent coloured particles of any form, especially produced by certain molluscs in their shell or alternatively synthesized, which have a colour effect via optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic colorants.

Examples of nacres that may also be mentioned include natural mica coated with titanium oxide, with iron oxide, with natural pigment or with bismuth oxychloride.

Among the commercially available nacres, mention may be made of the Timica, Flamenco and Duochrome (mica-based) nacres sold by the company BASF, the Timiron nacres sold by the company Merck, the Prestige mica-based nacres sold by the company Eckart, the following nacres based on natural mica: Sunpearl from the company Sun Chemical, KTZ from the company Kobo and Sunprizma from the company Sun Chemical, the Sunshine and Sunprizma nacres based on synthetic mica sold by the company Sun Chemical, and the Timiron Synwhite nacres based on synthetic mica sold by the company MERCK.

The nacres may more particularly have a yellow, pink, red, bronze, orange, brown, gold and/or coppery colour or glint.

As illustrations of nacres that may be used in the context of the present invention, mention may be made of gold-coloured nacres sold especially by the company BASF under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the names Bronze fine (17384) (Colorona) and Bronze (17353) (Colorona) and by the company BASF under the name Super bronze (Cloisonne); the orange nacres sold especially by the company BASF under the names Orange 363C (Cloisonne) and Orange MCR 101 (Cosmica) and by the company Merck under the names Passion orange (Colorona) and Matte orange (17449) (Microna); the brown-tinted nacres sold especially by the company BASF under the names Nuantique copper 340XB (Cloisonne) and Brown CL4509 (Chromalite); the nacres with a copper tint sold especially by the company BASF under the name Copper 340A (Timica); the nacres with a red tint sold especially by the company Merck under the name Sienna fine (17386) (Colorona); the nacres with a yellow tint sold especially by the company BASF under the name Yellow (4502) (Chromalite); the red-tinted nacres with a golden tint sold especially by the company BASF under the name Sunstone G012 (Gemtone); the pink nacres sold especially by the company BASF under the name Tan opale G005 (Gemtone); the black nacres with a golden tint sold especially by the company BASF under the name Nu antique bronze 240 AB (Timica); the blue nacres sold especially by the company Merck under the name Matte blue (17433) (Microna); the white nacres with a silvery tint sold especially by the company Merck under the name Xirona Silver; and the golden-green pinkish-orange nacres sold especially by the company Merck under the name Indian summer (Xirona), and mixtures thereof.

Among the particles with a metallic glint, mention may be made especially of:

particles of at least one metal and/or of at least one metal derivative, particles comprising a single-material or multi-material organic or inorganic substrate, at least partially coated with at least one layer with a metallic glint comprising at least one metal and/or at least one metal derivative, and mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" is intended to denote compounds derived from metals, especially oxides, fluorides, chlorides and sulphides.

Illustrations of these particles that may be mentioned include aluminium particles, such as those sold under the names Starbrite 1200 EAC® by the company Siberline and Metalure® by the company Eckart.

Mention may also be made of metal powders of copper or of alloy mixtures such as the references 2844 sold by the company Radium Bronze, metallic pigments, for instance aluminium or bronze, such as those sold under the names Rotosafe 700 from the company Eckart, silica-coated aluminium particles sold under the name Visionaire Bright Silver from the company Eckart, and metal alloy particles, for instance the silica-coated bronze (alloy of copper and zinc) powders sold under the name Visionaire Bright Natural Gold from the company Eckart.

They may also be particles comprising a glass substrate such as those sold by the company Nippon Sheet Glass under then names Microglass Metashine, Xirona from the company Merck, Ronastar from the company Merck, Reflecks from the company BASF and Mirage from the company BASF.

The goniochromatic colouring agent may be chosen, for example, from multilayer interference structures and liquid-crystal colouring agents.

Examples of symmetrical multilayer interference structures that may be used in the compositions prepared in accordance with the invention are, for example, the following structures: $Al/SiO_2/Al/SiO_2/Al$, pigments having this structure being sold by the company DuPont de Nemours; $Cr/MgF_2/Al/MgF_2/Cr$, pigments having this structure being sold under the name Chromaflair by the company Flex; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being sold under the name Sicopearl by the company BASF; $MoS_2/SiO_2/mica-oxide/SiO_2/MoS_2$; $Fe_2O_3/SiO_2/mica-oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO/TiO/mica/SnO$, pigments having these structures being sold under the name Xirona by the company Merck (Darmstadt). By way of example, these pigments may be the pigments of silica/titanium oxide/tin oxide structure sold under the name Xirona Magic by the company Merck, the pigments of silica/brown iron oxide structure sold under the name Xirona Indian Summer by the company Merck and the pigments of silica/titanium oxide/mica/tin oxide structure sold under the name Xirona Caribbean Blue by the company Merck. Mention may also be made of the Infinite Colors pigments from the company Shiseido. Different effects are obtained depending on the thickness and the nature of the various layers. Thus, with the $Fe_2O_3/SiO_2/Al/SiO_2/Fe_2O_3$ structure, the colour changes from greenish gold to reddish grey for $SiO_2$ layers of 320 to 350 nm; from red to gold for $SiO_2$ layers of 380 to 400 nm; from violet to green for $SiO_2$ layers of 410 to 420 nm; from copper to red for $SiO_2$ layers of 430 to 440 nm.

Examples of pigments with a polymeric multilayer structure that may be mentioned include those sold by the company 3M under the name Color Glitter. Mention may also be made of the flakes resulting from a polymeric multilayer structure: Disco from the company Glitterex and Microglitter from the company Venture Chemical.

Fillers

A composition in accordance with the invention may also comprise at least one filler of organic or mineral nature.

The term "filler" should be understood to mean colourless or white solid particles of any shape which are in a form that is insoluble and dispersed in the medium of the composition. They are mineral or organic in nature and make it possible to confer softness and mattness on the composition and a uniform makeup result.

The fillers used in the compositions according to the present invention may be in lamellar, globular or spherical form, in the form of fibres or in any other intermediate form between these defined forms.

The fillers according to the invention may or may not be surface-coated, and in particular they may be surface-treated with silicones, amino acids, fluoro derivatives or any other substance that promotes the dispersion and compatibility of the filler in the composition.

Among the mineral fillers that can be used in the compositions according to the invention, mention may be made of talc, mica, silica, trimethyl siloxysilicate, kaolin, bentone, calcium carbonate, magnesium hydrogen carbonate, hydroxyapatite, boron nitride, hollow silica microspheres (Silica Beads from Maprecos), glass or ceramic microcapsules, silica-based fillers, for instance Aerosil 200 or Aerosil 300; Sunsphere H-33 and Sunsphere H-51 sold by Asahi Glass; Chemicelen sold by Asahi Chemical; composites of silica and of titanium dioxide, for instance the TSG series sold by Nippon Sheet Glass, and mixtures thereof.

A filler suitable for the invention may preferentially be calcium carbonate.

Among the organic fillers that can be used in the compositions according to the invention, mention may be made of polyamide powders (Nylon® Orgasol from Atochem), poly-β-alanine and polyethylene powders, polytetrafluoroethylene (Teflon®) powders, lauroyllysine, starch, tetrafluoroethylene polymer powders, hollow polymer microspheres, such as EXPANCEL (NOBEL INDUSTRIE), metal soaps derived from organic carboxylic acids containing from 8 to 22 carbon atoms, preferably from 12 to 18 carbon atoms, for example zinc stearate, magnesium stearate or lithium stearate, zinc laurate, magnesium myristate, Polypore® L 200 (Chemdal Corporation), silicone resin microbeads (Tospearl® from Toshiba, for example), polyurethane powders, in particular powders of crosslinked polyurethane comprising a copolymer, said copolymer comprising trimethylol hexyllactone, for instance the hexamethylene diisocyanate/trimethylol hexyllactone polymer sold under the name Plastic Powder D-400® or Plastic Powder D-800® by the company Toshiki, carnauba microwaxes, such as the product sold under the name MicroCare 350® by the company Micro Powders, microwaxes of synthetic wax, such as the product sold under the name MicroEase 114S® by the company Micro Powders, microwaxes constituted of a mixture of carnauba wax and of polyethylene wax, such as those sold under the names MicroCare 300® and 310® by the company Micro Powders, microwaxes constituted of a mixture of carnauba wax and of synthetic wax, such as the product sold under the name MicroCare 325® by the company Micro Powders, polyethylene microwaxes, such as those sold under the names Micropoly 200, 220), 220L® and 250S® by the company Micro Powders; and mixtures thereof.

According to one particular embodiment, the composition also comprises at least one soft-focus agent. Preferably, in this case, it will be an anhydrous composition.

Soft-Focus Agent

The term "soft-focus agent" according to the invention is understood to mean an agent intended to give greater transparency to the complexion and a soft-focus effect. In particular, the soft-focus agent enables the composition that contains it to reduce, via an optical effect, the skin micro-relief, and in particular skin defects such as marks, wrinkles and fine lines.

This agent may especially be chosen from inorganic fillers, organic fillers, composite colouring agents, silicone elastomers, and mixtures thereof.

The soft-focus agents that can be used in the composition according to the invention may especially comprise or be constituted of particles having a number-average size of less than or equal to 15 µm, especially less than or equal to 10 µm, in particular less than or equal to 7.5 µm, or even less than or equal to 5 µm, for example between 1 µm and 5 µm.

The term "number-average size" denotes the dimension given by statistical particle size distribution for half the population, referred to as D50.

These particles may be in any form and in particular may be spherical or non-spherical. The soft-focus agents according to the invention may be of any chemical nature as long as they are compatible with a cosmetic use and they do not adversely affect the anticipated properties of the composition.

They may thus be chosen from silica and silicate powders, especially alumina powder, powders of polymethyl methacrylate (PMMA) type, talc, silica/$TiO_2$ or silica/zinc oxide composites, polyethylene powders, starch powders, polyamide powders, styrene/acrylic copolymer powders and silicone elastomers, and mixtures thereof.

In particular, the soft-focus agent is chosen from polytetrafluoroethylene powders, polyurethane powders, camauba microwaxes, synthetic wax microwaxes, silicone resin powders, hollow hemispherical silicone particles, acrylic copolymer powders, expanded vinylidene/acrylonitrile/methylene methacrylate microspheres, polyethylene powders, especially comprising at least one ethylene/acrylic acid copolymer, crosslinked elastomeric organopolysiloxane powders, crosslinked elastomeric organopolysiloxane powders coated with silicone resin, polyamide powders, powders of silica and silicates, especially of alumina, talc having a number-average size of less than or equal to 3 microns, silica/TiO2 composites, barium sulphate particles, boron nitride particles, silica particles surface-treated with an inorganic wax at 1 to 2%, amorphous silica microspheres, silica microbeads, talc/$TiO_2$/alumina/silica composite powders, sericite/$TiO_2$/brown iron oxide/silica composite pigments, silicone elastomers, and mixtures thereof.

Preferably, the soft-focus agent is chosen from a sericite/$TiO_2$/brown iron oxide/silica composite pigment, a polyurethane powder, a silicone elastomer, and mixtures thereof.

Examples of soft-focus fillers, composite colouring agents and silicone elastomers are given below.

Soft-Focus Fillers

According to one embodiment, the composition according to the invention may comprise a filler as a soft-focus agent.

In particular, the soft-focus agent is a filler chosen from polytetrafluoroethylene powders, polyurethane powders, camauba microwaxes, synthetic wax microwaxes, silicone resin powders, hollow hemispherical silicone particles, acrylic copolymer powders, vinylidene/acrylonitrile/methylene methacrylate expanded microspheres, polyethylene powders, especially comprising at least one ethylene/acrylic acid copolymer, crosslinked elastomeric organopolysiloxane powders, crosslinked elastomeric organopolysiloxane powders coated with silicone resin, polyamide powders, powders of silica and silicates, especially of alumina, talc having a number-average size of less than or equal to 3 microns, silica/TiO2 composites, barium sulphate particles, boron nitride particles, silica particles surface-treated with an inorganic wax at 1 to 2%, amorphous silica microspheres, silica microbeads, talc/$TiO_2$/alumina/silica composite powders, for instance those sold under the name Coverleaf AR-80® and mixtures thereof.

As soft-focus fillers that can be used according to the invention, mention may especially be made of:

a) organic fillers such as polytetrafluoroethylene powders, for instance the PTFEs Ceridust 9205F® from Clariant having an average size of 8 µm;

polyurethane powders, such as powders of crosslinked polyurethane comprising a copolymer, said copolymer comprising trimethylol hexyllactone, such as the hexamethylene diisocyanate/trimethylol hexyllactone polymer sold under the name Plastic Powder D-400® or Plastic Powder D-800® by the company Toshiki, camauba microwaxes such as the product sold under the name MicroCare 350® by the company Micro Powders, and synthetic wax microwaxes, such as the product sold under the name MicroEase 114S® by the company Micro Powders;

silicone resin powders, for instance the silicone resin Tospearl 145A® from GE Silicone, with an average size of 4.5 µm;

hollow hemispherical silicone particles, for instance NLK 500®, NLK 506® and NLK 510® from Takemoto Oil and Fat;

powders of acrylic copolymers, especially of polymethyl (meth)acrylate, for instance the PMMA particles Jurimer MBI® from Nihon Junyoki, with an average size of 8 µm, the hollow PMMA spheres sold under the name Covabead LH85® by the company Wackherr, the PMMA particles Ganzpearl GMP0820® from the company Ganz Chemical and vinylidene/acrylonitrile/methylene methacrylate expanded microspheres sold under the name Expancel®;

polyethylene powders, especially comprising at least one ethylene/acrylic acid copolymer, and in particular consisting of ethylene/acrylic acid copolymers, for instance the particles Flobeads EA 209® from Sumitomo (with an average size of 10 µm;

crosslinked elastomeric organopolysiloxane powders, such as Dow Corning 9701 Cosmetic Powder® from the company Dow Corning (INCI name: dimethicone/vinyl dimethicone crosspolymer);

crosslinked elastomeric organopolysiloxane powders coated with silicone resin, especially with silsesquioxane resin, as described, for example, in U.S. Pat. No. 5,538,793. Such elastomer powders are sold under the names KSP-100®, KSP-101®, KSP-102®, KSP-103®, KSP-104® and KSP-105® by the company Shin-Etsu;

polyamide powders, such as Nylon® 12 powder, especially the product sold under the name Orgasol 2002 Extra D Nat Cos® by the company Atochem;

b) inorganic fillers such as:
powders of silica and silicates, especially of alumina,
talc, in particular talc having a number-average size of less than or equal to 3 microns, for example talc having a number-average size of 1.8 microns and especially the product sold under the trade name Talc P3® by the company Nippon Talc,
silica/TiO2 composites such as the composites NPT30K3TA from Nippon Sheet Glass or STMCAS-152010 from Catalysts & Chemicals, or silica/zinc oxide composites,
barium sulphate particles,
boron nitride particles,
silica particles surface-treated with an inorganic wax at 1 to 2% (INCI name: hydrated silica (and) paraffin) such as those sold by the company Degussa,
amorphous silica microspheres, such as those sold under the name Sunsphere, for example with the reference H-53®, by the company Asahi Glass,
silica microbeads, such as those sold under the name SB-700® or SB-150® by the company Miyoshi,
talc/$TiO_2$/alumina/silica composite powders such as those sold under the name Coverleaf AR-80® by the company Catalyst & Chemicals,
and mixtures thereof.

According to one preferred embodiment, the composition comprises at least one soft-focus organic filler chosen from polytetrafluoroethylene powders, polyurethane powders, silicone resin powders, hollow hemispherical silicone particles, acrylic copolymer powders, polyethylene powders, crosslinked elastomeric organopolysiloxane powders, crosslinked elastomeric organopolysiloxane powders coated with silicone resin, especially with silsesquioxane resin, polyamide powders, and mixtures thereof.

Soft-Focus Colouring Agent

According to another embodiment, the composition according to the invention may comprise, as soft-focus agent, a soft-focus colouring agent, of composite type.

This colouring agent may comprise a pigment having a structure that may be, for example, of sericite/brown iron oxide/titanium dioxide/silica type. Such a pigment is sold, for example, under the reference Coverleaf NS or JS or MF by the company Chemicals and Catalysts.

The colouring agent may also comprise a pigment having a structure that may be for example of the type of silica microspheres containing iron oxide, such as the product sold by the company Miyoshi under the reference PC BALL PC-LL-100 P, this pigment being constituted of silica microspheres containing yellow iron oxide.

According to one preferred embodiment, use will be made of a composite colouring agent having a structure of sericite/brown iron oxide/titanium dioxide/silica type such as the product sold under the reference Coverleaf MF by the company Chemicals and Catalysts.

Soft-Focus Silicone Elastomers

According to another embodiment, the composition according to the invention may comprise, as soft-focus agent, at least one silicone elastomer or elastomeric organopolysiloxane, preferably at least partially crosslinked.

The elastomeric organopolysiloxanes used in the composition according to the invention are preferably partially or completely crosslinked. They are in the form of particles. In particular, the elastomeric organopolysiloxane particles have a size ranging from 0.1 to 500 µm, preferably from 3 to 200 µm and better still from 3 to 50 µm. These particles may have any form and may for example be spherical, flat or amorphous.

The elastomeric crosslinked organopolysiloxane may be obtained via a crosslinking addition reaction of a diorganopolysiloxane containing at least one hydrogen atom bonded to a silicon atom and of a diorganopolysiloxane containing at least two ethylenically unsaturated groups bonded to different silicon atoms, especially in the presence of a platinum catalyst; or via a dehydrogenation crosslinking condensation reaction between a hydroxyl-terminated diorganopolysiloxane and a diorganopolysiloxane containing at least one hydrogen atom bonded to a silicon atom, especially in the presence of an organotin compound; or via a crosslinking condensation reaction of a hydroxyl-terminated diorganopolysiloxane and of a hydrolysable organopolysilane; or via thermal crosslinking of organopolysiloxane, especially in the presence of an organoperoxide catalyst; or via crosslinking of organopolysiloxane by high-energy radiation such as gamma rays, ultraviolet rays or an electron beam.

The elastomer obtained may be a non-emulsifying elastomer or an emulsifying elastomer.

The term "non-emulsifying" defines organopolysiloxane elastomers that do not contain a hydrophilic chain. The term "emulsifying" means crosslinked organopolysiloxane elastomers having at least one hydrophilic chain.

The elastomeric crosslinked organopolysiloxane particles may be conveyed in the form of a gel constituted of an elastomeric organopolysiloxane included in at least one hydrocarbon-based oil and/or one silicone oil. In these gels, the organopolysiloxane particles are often non-spherical particles.

The elastomeric crosslinked organopolysiloxane particles may also be in the form of a powder, especially in the form of a spherical powder, in particular coated with silicone resin, especially with silsesquioxane resin, as described for example in U.S. Pat. No. 5,538,793. Such elastomers are sold under the names KSP-100, KSP-101, KSP-102, KSP-103, KSP-104 and KSP-105 by the company Shin-Etsu.

Other elastomeric crosslinked organopolysiloxanes in the form of powders may be powders of a hybrid silicone functionalized with fluoroalkyl groups, sold especially under the name KSP-200 by the company Shin-Etsu; or powders of hybrid silicones functionalized with phenyl groups, sold especially under the name KSP-300 by the company Shin-Etsu.

According to one particular embodiment of the invention, the soft-focus agent is an emulsifying silicone elastomer, i.e. a partially or completely crosslinked elastomeric organopolysiloxane (silicone elastomer), comprising at least one hydrophilic chain.

The emulsifying silicone elastomer may be chosen from polyoxyalkylenated silicone elastomers.

The polyoxyalkylenated silicone elastomer is a crosslinked organopolysiloxane that may be obtained by a crosslinking addition reaction of diorganopolysiloxane containing at least one hydrogen bonded to silicon and of a polyoxyalkylene containing at least two ethylenically unsaturated groups.

Preferably, the polyoxyalkylenated crosslinked organopolysiloxane is obtained by a crosslinking addition reaction (A1) of diorganopolysiloxane containing at least two hydrogens each bonded to a silicon, and (B1) of polyoxyalkylene containing at least two ethylenically unsaturated groups, especially in the presence (C1) of a platinum catalyst, as described, for example, in U.S. Pat. No. 5,236,986 and U.S. Pat. No. 5,412,004.

In particular, the organopolysiloxane may be obtained by reaction of dimethylvinylsiloxy-terminated polyoxyalkylene (especially polyoxyethylene and/or polyoxypropylene) and of trimethylsiloxy-terminated methylhydropolysiloxane, in the presence of a platinum catalyst.

The organic groups bonded to the silicon atoms of compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A1) may thus be chosen from trimethylsiloxy-terminated methylhydropolysiloxanes, trimethylsiloxy-terminated dimethylsiloxane/methylhydrosiloxane copolymers, dimethylsiloxane/methylhydrosiloxane cyclic copolymers, and trimethylsiloxy-terminated dimethylsiloxane/methylhydrosiloxane/laurylmethylsiloxane copolymers.

Compound (C1) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated silicone elastomers may be formed from divinyl compounds, in particular polyoxyalkylenes containing at least two vinyl groups, reacting with Si—H bonds of a polysiloxane.

The polyoxyalkylenated silicone elastomer according to the invention is conveyed in the form of a gel in at least one hydrocarbon-based oil and/or one silicone oil. In these gels, the polyoxyalkylenated elastomer is in the form of non-spherical particles.

Polyoxyalkylenated elastomers are especially described in U.S. Pat. No. 5,236,986, U.S. Pat. No. 5,412,004, U.S. Pat. No. 5,837,793 and U.S. Pat. No. 5,811,487, the content of which is incorporated by reference.

Polyoxyalkylenated silicone elastomers that may be used include those sold under the names KSG-21, KSG-20, KSG-30, KSG-31, KSG-32, KSG-33, KSG-210, KSG-310, KSG-320, KSG-330, KSG-340 and X-226146 by the company Shin-Etsu, and DC9010 and DC9011 by the company Dow Corning.

According to one preferred embodiment, use is made of the polyoxyalkylenated silicone elastomer sold under the reference KSG-210 by the company Shin-Etsu.

The emulsifying silicone elastomer may also be chosen from polyglycerolated silicone elastomers.

The polyglycerolated silicone elastomer is a crosslinked elastomeric organopolysiloxane that may be obtained by a crosslinking addition reaction of diorganopolysiloxane containing at least one hydrogen bonded to silicon and of polyglycerolated compounds containing ethylenically unsaturated groups, especially in the presence of a platinum catalyst.

Preferably, the crosslinked elastomeric organopolysiloxane is obtained by a crosslinking addition reaction (A) of diorganopolysiloxane containing at least two hydrogens each bonded to a silicon, and (B) of glycerolated compounds containing at least two ethylenically unsaturated groups, especially in the presence (C) of a platinum catalyst.

In particular, the organopolysiloxane may be obtained by reaction of a dimethylvinylsiloxy-terminated polyglycerolated compound and of trimethylsiloxy-terminated methylhydropolysiloxane, in the presence of a platinum catalyst.

Compound (A) is the base reactant for the formation of elastomeric organopolysiloxane, and the crosslinking takes place via an addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, especially a linear-chain or branched-chain structure or a cyclic structure.

Compound (A) may have a viscosity at 25° C. ranging from 1 to 50 000 centistokes, especially so as to be miscible with compound (B).

The organic groups bonded to the silicon atoms of compound (A) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. Preferably, said organic group is chosen from methyl, phenyl and lauryl groups.

Compound (A) may thus be chosen from trimethylsiloxy-terminated methylhydropolysiloxanes, trimethylsiloxy-terminated dimethylsiloxane/methylhydrosiloxane copolymers, dimethylsiloxane/methylhydrosiloxane cyclic copolymers, and trimethylsiloxy-terminated dimethylsiloxane/methylhydrosiloxane/laurylmethylsiloxane copolymers.

Compound (B) may be a polyglycerolated compound corresponding to formula (B') below:

$$C_mH_{2m-1}—O—[Gly]n-C_mH_{2m-1} \quad (B')$$

in which m is an integer ranging from 2 to 6, n is an integer ranging from 2 to 200, preferably ranging from 2 to 100, preferably ranging from 2 to 50, preferably n ranging from 2 to 20, preferably ranging from 2 to 10 and preferentially ranging from 2 to 5, and in particular n is equal to 3; Gly denotes:

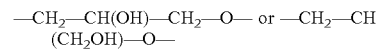

—CH$_2$—CH(OH)—CH$_2$—O— or —CH$_2$—CH(CH$_2$OH)—O—

Advantageously, the sum of the number of ethylenic groups per molecule in compound (B) and of the number of hydrogen atoms bonded to silicon atoms per molecule in compound (A) is at least 4.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C) is preferably added in an amount of from 0.1 to 1000 parts by weight and better still from 1 to 100 parts by weight, as clean platinum metal, per 1000 parts by weight of the total amount of compounds (A) and (B).

The polyglycerolated silicone elastomer according to the invention is generally mixed with at least one hydrocarbon-based oil and/or one silicone oil to form a gel. In these gels, the polyglycerolated elastomer is often in the form of non-spherical particles.

Such elastomers are described especially in patent application WO 2004/024798.

Polyglycerolated silicone elastomers that may be used include those sold under the names KSG-710, KSG-810, KSG-820, KSG-830 and KSG-840 by the company Shin-Etsu.

According to one particular embodiment, the composition according to the invention comprises at least one non-emulsifying, non-spherical silicone elastomer mixed with at least one hydrocarbon-based oil and/or one silicone oil to form a gel.

According to one preferred embodiment, use is made of the polyglycerolated silicone elastomer sold under the reference KSG-710 by the company Shin-Etsu.

According to another embodiment of the invention, the soft-focus agent used is a non-emulsifying silicone elastomer.

The term "non-emulsifying" silicone elastomers means organopolysiloxane elastomers that do not contain a hydrophilic chain, such as polyoxyalkylene or polyglycerol units.

The non-emulsifying silicone elastomer is an elastomeric crosslinked organopolysiloxane which may be obtained via a crosslinking addition reaction of diorganopolysiloxane containing at least one hydrogen bonded to silicon and of diorganopolysiloxane containing ethylenically unsaturated groups bonded to silicon, especially in the presence of a platinum catalyst; or via a dehydrogenation crosslinking condensation reaction between a hydroxyl-terminated diorganopolysiloxane and a diorganopolysiloxane containing at least one hydrogen bonded to silicon, especially in the presence of an organotin compound; or via a crosslinking condensation reaction of a hydroxyl-terminated diorganopolysiloxane and of a hydrolysable organopolysilane; or via thermal crosslinking of organopolysiloxane, especially in the presence of an organoperoxide catalyst; or via crosslinking of organopolysiloxane by high-energy radiation such as gamma rays, ultraviolet rays or an electron beam.

Preferably, the elastomeric crosslinked organopolysiloxane is obtained by a crosslinking addition reaction (A2) of a diorganopolysiloxane containing at least two hydrogens each bonded to a silicon, and (B2) of a diorganopolysiloxane containing at least two ethylenically unsaturated groups bonded to silicon, especially in the presence (C2) of a platinum catalyst, for instance as described in patent application EP-A-295 886.

In particular, the organopolysiloxane may be obtained by reaction of dimethylvinylsiloxy-terminated dimethylpolysiloxane and of trimethylsiloxy-terminated methylhydropolysiloxane, in the presence of a platinum catalyst.

Compound (A2) is the base reactant for the formation of an elastomeric organopolysiloxane and the crosslinking takes place via an addition reaction of compound (A2) with compound (B2) in the presence of the catalyst (C2).

Compound (A2) is advantageously a diorganopolysiloxane containing at least two lower (for example of C2-C4) alkenyl groups; the lower alkenyl group may be chosen from vinyl, allyl and propenyl groups. These lower alkenyl groups may be located in any position of the organopolysiloxane molecule, but are preferably located at the ends of the organopolysiloxane molecule. The organopolysiloxane (A2) may have a branched chain, linear chain, cyclic or network structure, but the linear chain structure is preferred. Compound (A2) may have a viscosity ranging from the liquid state to the gum state. Preferably, compound (A2) has a viscosity of at least 100 centistokes at 25° C.

The organopolysiloxanes (A2) may be chosen from methylvinylsiloxanes, methylvinylsiloxane/dimethylsiloxane copolymers, dimethylvinylsiloxy-terminated dimethylpolysiloxanes, dimethylvinylsiloxy-terminated dimethylsiloxane/methylphenylsiloxane copolymers, dimethylvinylsiloxy-terminated dimethylsiloxane/diphenyl-siloxane/methylvinylsiloxane copolymers, trimethylsiloxy-terminated dimethyl-siloxane/methylvinylsiloxane copolymers, trimethylsiloxy-terminated dimethyl-siloxane/methylphenylsiloxane/methylvinylsiloxane copolymers, dimethylvinylsiloxy-terminated methyl(3,3,3-trifluoropropyl)polysiloxanes, and dimethylvinylsiloxy-terminated dimethylsiloxane/methyl(3,3,3-trifluoropropyl)siloxane copolymers.

Compound (B2) is in particular an organopolysiloxane containing at least two hydrogens bonded to silicon in each molecule and is thus the crosslinking agent for compound (A2). Advantageously, the sum of the number of ethylenic groups per molecule in compound (A2) and the number of hydrogen atoms bonded to silicon per molecule in compound (B2) is at least 4.

Compound (B2) may be in any molecular structure, especially in a linear chain, branched chain or cyclic structure.

Compound (B2) may have a viscosity at 25° C. ranging from 1 to 50 000 centistokes, especially so as to be miscible with compound (A).

It is advantageous for compound (B2) to be added in an amount such that the molecular ratio between the total amount of hydrogen atoms bonded to silicon in compound (B2) and the total amount of all the ethylenically unsaturated groups in compound (A2) is in the range from 1/1 to 20/1.

Compound (B2) may be chosen from trimethylsiloxy-terminated methylhydropolysiloxanes, trimethylsiloxy-terminated dimethylsiloxane/methylhydrosiloxane copolymers and dimethylsiloxane/methylhydrosiloxane cyclic copolymers.

Compound (C2) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is preferably added in an amount of from 0.1 to 1000 parts by weight and better still from 1 to 100 parts by weight, as clean platinum metal, per 1000 parts by weight of the total amount of compounds (A2) and (B2).

Other organic groups may be bonded to silicon in the organopolysiloxanes (A2) and (B2) described previously, for instance alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

According to one preferred embodiment, the non-emulsifying silicone elastomer is mixed with at least one hydrocarbon-based oil and/or silicone oil to form a gel. In these gels, the non-emulsifying elastomer is in the form of non-spherical particles.

Non-emulsifying elastomers that may be used include those sold under the names KSG-6, KSG-15, KSG-16, KSG-18, KSG-31, KSG-32, KSG-33, KSG-41, KSG-42, KSG-43, KSG-44, USG-105 and USG-106 by the company Shin-Etsu, DC 9040, DC9041, DC9045, DC 9509, DC9505 DC 9506, DC5930, DC9350, DC9045 and DC9043 by the company Dow Corning, Gransil by the company Grant Industries, and SFE 839 by the company General Electric.

According to one preferred embodiment, use will be made, as non-emulsifying elastomer, of the product sold under the reference DC9045 by the company Dow Corning.

Advantageously, the composition according to the invention may contain at least two soft-focus agents chosen from polyurethane powders, silicone elastomers, composite colouring agents, and mixtures thereof.

In particular, the composition according to the invention may contain an emulsifying silicone elastomer and a non-emulsifying silicone elastomer.

Depending on the nature of the soft-focus agent, a person skilled in the art will adjust its content in the composition in order to obtain the desired effect.

By way of example, the soft-focus filler may be present in the composition according to the invention in a content ranging from 0.1% to 80% by weight and especially ranging from 1% to 70% by weight relative to the total weight of the composition, especially between 5% and 30%, for example of the order of 8%.

The soft-focus colouring agent may be present in the composition according to the invention in a content ranging from 0.1% to 30% by weight and especially ranging from 1% to 20% by weight relative to the total weight of the composition, especially between 5% and 15%, for example of the order of 8%.

The soft-focus silicone elastomer may be present in the composition according to the invention in a content of active material ranging from 0.01% to 8% by weight, preferably ranging from 2% to 7% by weight and more preferentially ranging from 3% to 6% by weight relative to the total weight of the composition.

Additives

A cosmetic composition according to the invention may also comprise, in addition, any additive usually used in the field concerned, chosen, for example, from film-forming agents, and where appropriate auxiliary film-forming agents, gums, semicrystalline polymers, antioxidants, vitamins, essential oils, preserving agents, fragrances, neutralizers, antiseptic agents and UV protection agents, and mixtures thereof.

A composition according to the invention may especially be in the form of a product for caring for and/or making up the skin, in particular the skin of the body or of the face.

According to one embodiment, a composition of the invention may advantageously be in the form of a foundation or a complexion corrector.

A composition of the invention may be obtained via any preparation process known to those skilled in the art.

The present invention will be understood more clearly by means of the examples that follow.

These examples are given as illustrations of the invention and should not be interpreted as limiting the scope thereof.

The values are expressed as % by weight.

EXAMPLES

Example 1: Cream (W/O Emulsion)

|  | 1A (comparative) | 1B (invention) | 1C (invention) |
| --- | --- | --- | --- |
| Water | 36.9 | 35.335 | 33.6 |
| Cyclopentadimethylsiloxane (Dow Corning 245 Fluid from Dow Corning) | 27.4 | 25.9 | 24.57 |
| Polyglyceryl-4 isostearate/cetyl dimethicone copolyol/hexyl laurate mixture sold under the name Abil WE 09 by the company Goldschmidt | 9 | 8.55 | 8.1 |

-continued

|  | 1A (comparative) | 1B (invention) | 1C (invention) |
| --- | --- | --- | --- |
| Ethanol | 5 | 4.75 | 4.5 |
| Glycerol | 5 | 4.75 | 4.5 |
| Isododecane | 5 | 4.75 | 4.5 |
| Mixture of polydiphenyldimethylsiloxane (gum - viscosity >1 000 000 cSt - MW: 600 000) and of cyclopentadimethylsiloxane (15/85) sold under the name Silbione by Bluestar | 4 | 3.8 | 3.6 |
| Phenyl trimethicone | 1.6 | 1.37 | 1.14 |
| Distearyldimethylammonium-modified hectorite (Bentone 38 VCG from Elementis) | 1.2 | 1.14 | 1.08 |
| Corn starch esterified with octenylsuccinic anhydride, aluminium salt (Dry Flo Plus from Akzo Nobel) | 1 | 0.95 | 0.9 |
| Protected 2-ethylhexyl 4-methoxycinnamate (Parsol MCX from DSM Nutritional Products) | 1 | 0.95 | 0.9 |
| Magnesium sulphate | 0.7 | 0.665 | 0.63 |
| Preserving agents | 0.7 | 0.665 | 0.63 |
| Cellulose gum | 0.5 | 0.475 | 0.45 |
| Tristearin and acetylated glycol stearate | 0.5 | 0.475 | 0.45 |
| Expanded vinylidene chloride/acrylonitrile/PMMA microspheres containing isobutane (Expancel 551 from Expancel) | 0.3 | 0.285 | 0.27 |
| Nylon-12 | 0.2 | 0.19 | 0.18 |
| Dispersion of bismuth oxychloride in 2-ethylhexyl hydroxystearate (70:30) (Timiron Liquid Silver ®) from Merck | 0 | 5 | 10 |

Procedure:

The dispersion of bismuth oxychloride in 2-ethylhexyl hydroxystearate is introduced into the fatty phase. The aqueous phase is prepared, then, using a Rayneri mixer equipped with a deflocculator, the emulsion is produced, with vigorous stirring and at room temperature.

Makeup Evaluation:

The compositions are applied to several panels of 10 women aged from 25 to 55 years old. The evaluations are made by making up the faces of said women (self-evaluations, evaluations by the formulators, evaluation by aestheticians). The formulae are therefore compared with one another regarding the criteria of makeup effect and especially the luminosity.

The formulae containing the dispersion of bismuth oxychloride in 2-ethylhexyl hydroxystearate are evaluated as being more luminous than the formulae that do not contain this ingredient. Indeed, the formulae containing the dispersion of bismuth oxychloride in 2-ethylhexyl hydroxystearate reflect the light more, in a uniform and continuous manner.

This luminous effect is intensified with the increase in the amount of this ingredient in the formulae.

Example 2: Concealer for Masking Visible Unevenness of the Face

| Name | 2F (invention) | 2E (invention) | 2D (comparative) |
| --- | --- | --- | --- |
| Magnesium sulphate | 0.6 | 0.6 | 0.6 |
| Distearyldimethylammonium-modified hectorite (Bentone 38 VCG from Elementis) | 0.6 | 0.6 | 0.6 |

-continued

| Name | 2F (invention) | 2E (invention) | 2D (comparative) |
|---|---|---|---|
| Vinylidene chloride/acrylonitrile/PMMA microspheres expanded with isobutane (Expancel 551 from Expancel) | 0.4 | 0.4 | 0.4 |
| Phenyl trimethicone | 1.2 | 1.2 | 1.2 |
| Preserving agents | 2.18 | 2.18 | 2.18 |
| Pigments: Yellow, red and black iron oxides coated with aluminium stearoyl glutamate and anatase titanium oxide coated with aluminium stearoyl glutamate (references NAI-C33-9001-10 NAI-C33-8001-10, NAI-C33-7001-10 and NAI-TAO-77891 from the company Miyoshi Kasei) | 3 | 7.2 | 11.34 |
| Deodorized isodecyl neopentanoate | 1.2 | 1.2 | 1.2 |
| Dispersion of bismuth oxychloride in 2-ethylhexyl hydroxystearate (70:30) (Timiron Liquid Silver ®) from Merck | 15 | 10.8 | 0 |
| Hydrogenated isoparaffin (6-8 mol of isobutylene) (Parleam from Nof Corporation) | 10 | 10 | 10 |
| Cyclopentadimethylsiloxane (Dow Corning 245 Fluid from Dow Corning) | 14.5 | 14.5 | 18 |
| Water | 38.32 | 37.32 | 40.48 |
| Glycerol | 5 | 5 | 5 |
| Propylene glycol | 3 | 3 | 3 |
| Sorbitan monoisostearate (Arlacel 987 from Croda) | 5 | 6 | 6 |

Procedure:

The procedure described in Example 1 is followed.

Makeup Evaluation:

The makeup result of the compositions is evaluated as described in Example 1.

The formulae containing the dispersion of bismuth oxychloride in 2-ethylhexyl hydroxystearate are evaluated as being more luminous than the formulae that do not contain this ingredient: they reflect the light more, in a uniform and continuous manner.

This luminous effect is intensified with the increase in the amount of this ingredient in the formulae.

Example 3: Pigmented Emulsion

| Name | 3H (invention) | 3G (comparative) |
|---|---|---|
| Magnesium sulphate | 1 | 1 |
| Glyceryl esters of plant, isostearic and adipic fatty acids (Softisan 649 from Sasol) | 0.2 | 0.2 |
| Pigments: Yellow, red and black iron oxides coated with aluminium stearoyl glutamate and anatase titanium oxide coated with aluminium stearoyl glutamate (references NAI-C33-9001-10 NAI-C33-8001-10, NAI-C33-7001-10 and NAI-TAO-77891 from the company Miyoshi Kasei) | 11 | 11 |
| Preserving agents | 1.25 | 1.25 |
| Protected 2-ethylhexyl 4-methoxycinnamate (Parsol MCX from DSM Nutritional Products) | 5 | 5 |
| Nacres | 0.04 | 0.44 |
| HDI/Trimethylol hexyllactone crosspolymer | 5 | 5 |
| Dispersion of bismuth oxychloride in 2-ethylhexyl hydroxystearate (70:30) (Timiron Liquid Silver ®) from Merck | 0.5 | 0 |
| Cyclopentadimethylsiloxane (Dow Corning 245 Fluid from Dow Corning) | 15 | 15 |
| Phenyl trimethicone | 1 | 1 |
| Dimethicone | 5 | 5 |
| Oxyethylenated polydimethylsiloxane (DP: 70 - Viscosity: 500 cSt) | 2.5 | 2.5 |
| Dimethicone and dimethicone/polyglycerin-3 crosspolymer | 9 | 9 |
| Dimethicone and dimethicone/PEG10/15 crosspolymer | 7.65 | 7.65 |
| Glycerol | 7 | 7 |
| Water | 26.86 | 26.96 |
| Propylene glycol | 1 | 1 |
| Pentylene glycol | 1 | 1 |

Procedure:

The procedure described in Example 1 is followed.

Makeup Evaluation:

The makeup result of the compositions is evaluated as described in Example 1.

The formulae containing the dispersion of bismuth oxychloride in 2-ethylhexyl hydroxystearate are evaluated as being more luminous than the formulae that do not contain this ingredient: they reflect the light more, in a uniform and continuous manner.

Said formula containing the dispersion of bismuth oxychloride in 2-ethylhexyl hydroxystearate is lighter in colour and gives greater coverage. It imparts more radiance to the face with a slightly more satiny look. It is also more unifying in terms of colour and smoothes out the relief more.

Example 4: W/Si Emulsion

| | 4A (comparative) | 4B (invention) | 4C (invention) |
|---|---|---|---|
| HYDROGENATED MALTOSE SOLUTION | 0.5 | 0.47 | 0.45 |
| TALC: MICRONIZED MAGNESIUM SILICATE (PARTICLE SIZE: 5 MICRONS) (CI: 77718) | 0.5 | 0.47 | 0.45 |
| REFINED PLANT PERHYDROSQUALENE | 1 | 0.95 | 0.9 |
| YELLOW IRON OXIDE COATED WITH ALUMINIUM STEAROYL GLUTAMATE (3%) NAI-C33-9001-10 from MIYOSHI KASEI | 1.63 | 1.55 | 1.45 |
| RED IRON OXIDE COATED WITH ALUMINIUM STEAROYL GLUTAMATE (3%) NAI-C33-8001-10 from MIYOSHI KASEI | 0.29 | 0.27 | 0.261 |
| BLACK IRON OXIDE COATED WITH ALUMINIUM STEAROYL GLUTAMATE (3%) NAI-C33-7001-10 from MIYOSHI KASEI | 0.13 | 0.12 | 0.12 |
| ANATASE TITANIUM OXIDE COATED WITH ALUMINIUM STEAROYL GLUTAMATE (97/3) (CI: 77891) (NAI-TAO-77891 from MIYOSHI KASEI) | 9.95 | 9.45 | 8.95 |
| POLYDIMETHYLSILOXANE CONTAINING ALPHA, OMEGA-OXYETHYLENATED/OXYPROPYLENATED GROUPS IN SOLUTION IN CYCLOPENTASILOXANE ABIL EM 97 ® from Evonik Goldschmidt | 1 | 0.95 | 0.9 |

-continued

|  | 4A (comparative) | 4B (invention) | 4C (invention) |
|---|---|---|---|
| Phenyltrimethylsiloxytrisiloxane (viscosity: 20 cSt - MW: 372) DOW CORNING 556 COSMETIC GRADE FLUID from Dow Corning | 2 | 1.9 | 1.8 |
| OXYETHYLENATED POLY-DIMETHYLSILOXANE (DP: 70 - VISCOSITY: 500 cSt) KF 6017 ® from Shin-Etsu | 2 | 1.9 | 1.8 |
| STABILIZED (0.1% BHT) 2-ETHYL-HEXYL P-METHOXY-4 CINNAMATE PARSOL MCX XR from DSM NUTRITIONAL PRODUCTS | 3 | 2.85 | 2.7 |
| Dispersion of bismuth oxychloride in 2-ethylhexyl hydroxystearate (70:30) (Timiron Liquid Sliver ®) from Merck | 0 | 5 | 10 |
| NYLON-12 MICROSPHERES (PARTICLE SIZE: 5 MICRONS) | 0.5 | 0.475 | 0.45 |
| DENATURED 96° ETHYL ALCOHOL | 13 | 12.35 | 11.7 |
| 1,3-BUTYLENE GLYCOL | 3 | 2.85 | 2.7 |
| MAGNESIUM SULPHATE | 0.7 | 0.66 | 0.63 |
| MICROBIOLOGICALLY CLEAN DEIONIZED WATER | 36.15 | 34.34 | 32.53 |
| CYCLOPENTADIMETHYLSILOXANE (DOW CORNING 245 FLUID ® from Dow Corning) | qs 100 | qs 100 | qs 100 |

Procedure:

The dispersion of bismuth oxychloride in 2-ethylhexyl hydroxystearate is introduced into the fatty phase. The aqueous phase is prepared, then, using a Rayneri mixer equipped with a deflocculator, the emulsion is produced, with vigorous stirring and at room temperature. Next, with moderate stirring, the alcohol is introduced.

Makeup Evaluation:

The compositions are applied to panels of 10 women aged from 25 to 55 years old having combination to oily skin. The evaluations are made by making up the faces of said women (self-evaluations, evaluations by the formulators, evaluation by aestheticians). The formulae are therefore compared with one another regarding the criteria of makeup effect and especially the luminosity.

The formulae containing the dispersion of bismuth oxychloride in 2-ethylhexyl hydroxystearate are evaluated as being more luminous than the formula that does not contain this ingredient. Indeed, the formulae containing the dispersion of bismuth oxychloride in 2-ethylhexyl hydroxystearate reflect the light more, in a uniform and continuous manner. This luminous effect is intensified with the increase in the amount of this ingredient in the formulae.

Furthermore, the fluid texture penetrates, leaving a soft and silky feeling on the fingers, for a discreet/natural makeup look. The complexion is luminous and unified and small colour imperfections (redness, shadows under the eyes) are reduced. The foundation captures the light to give an impression of relaxed skin.

Example 5: Water/Si Emulsion

|  | 5 D (comparative) | 5 E (invention) |
|---|---|---|
| SODIUM CHLORIDE | 1 | 1 |
| DENATURED 96° ETHYL ALCOHOL | 5 | 5 |
| YELLOW IRON OXIDE COATED WITH PERFLUOROALKYL PHOSPHATE (95/5) PFX-5 SUNPURO YELLOW C33-9001 from DAITO KASEI KOGYO | 1.87 | 1.87 |
| BLACK IRON OXIDE COATED WITH PERFLUOROALKYL PHOSPHATE (95/5) PFX-5 SUNPURO BLACK C33-7001 from DAITO KASEI KOGYO | 0.26 | 0.26 |
| RED IRON OXIDE COATED WITH PERFLUOROALKYL PHOSPHATE (95/5) PFX-5 SUNPURO RED C33-8001 from DAITO KASEI KOGYO | 0.63 | 0.63 |
| ANATASE TITANIUM OXIDE COATED WITH PERFLUOROALKYL PHOSPHATE (95/5) (CI: 77891) PF 5 TIO2 A 100 from DAITO KASEI KOGYO | 8.24 | 8.24 |
| Polyglycerolated emulsifying silicone elastomer at 25% by weight in polydimethylsiloxane (6 cSt) (KSG 710 from Shin-Etsu) | 7 | 7 |
| OXYETHYLENATED POLYMETHYL-ISOSTEARYL DIMETHYL METHYL SILOXANE (MW: 6 000) KF6028 from Shin-Etsu | 2 | 2 |
| POLYDIMETHYLSILOXANE (VISCOSITY: 5 cSt) DOW CORNING 200 FLUID 5 CST from Dow Corning | 2.5 | 2.5 |
| ETHYLENEDIAMINETETRAACETIC ACID, DISODIUM SALT, 2 H$_2$O | 0.2 | 0.2 |
| STABILIZED (0.1% BHT) 2-ETHYLHEXYL P-METHOXY-4 CINNAMATE PARSOL MCX XR from DSM NUTRITIONAL PRODUCTS | 3 | 3 |
| Dispersion of bismuth oxychloride in 2-ethylhexyl hydroxystearate (70:30) (Timiron Liquid Silver ®) from Merck | 0 | 1 |
| preserving agents | 0.5 | 0.5 |
| GLYCEROL | 5.5 | 5.5 |
| MICROBIOLOGICALLY CLEAN DEIONIZED WATER | 42.89 | 42.89 |
| CYCLOPENTADIMETHYLSILOXANE (DOW CORNING 245 FLUID ® from Dow Corning) | qs 100 | qs 100 |

Procedure:

The procedure described in Example 1 is followed.

Makeup Evaluation

The compositions are applied to panels of 10 women aged from 25 to 55 years old having combination to oily skin. The evaluations are made by making up the faces of said women (self-evaluations, evaluations by the formulators, evaluation by aestheticians). The formulae are therefore compared with one another regarding the criteria of makeup effect and especially the luminosity.

The formula containing the dispersion of bismuth oxychloride in 2-ethylhexyl hydroxystearate is evaluated as being more luminous than the formula that does not contain this ingredient. Indeed, the composition according to the invention reflects the light more, in a uniform and continuous manner.

Example 6: Colourless Anhydrous Gel

|  | 6A (invention) | 6B (comparative) |
|---|---|---|
| Crosslinked polydimethylsiloxane (12%) in cyclopentadimethyisiloxane (Dow Corning 9045 Silicone Elastomer Blend from Dow Corning) | 67 | 67 |

-continued

| | 6A (invention) | 6B (comparative) |
|---|---|---|
| Dispersion of bismuth oxychloride in 2-ethylhexyl hydroxystearate (70:30) (Timiron Liquid Silver ®) from Merck | 7 | 0 |
| Bismuth oxychloride (CI: 77163) | 0 | 4.9 |
| Cyclopentadimethylsiloxane (Dow Corning 245 Fluid from Dow Corning) | 26 | 28.1 |
| TOTAL | 100 | 100 |

Procedure:

The dispersion of bismuth oxychloride in 2-ethylhexyl hydroxystearate is introduced into the anhydrous mixture with moderate stirring.

Makeup Evaluation

The compositions are applied to half the face and the makeup result is evaluated. The composition according to the invention comprising the dispersion of bismuth oxychloride in combination with the non-emulsifying silicone elastomer is more luminous than the (comparative) composition comprising conventional bismuth oxychloride: the composition according to the invention reflects the light more, in a uniform and continuous manner. The complexion appears younger, with more radiance after application of the composition according to the invention, compared to the duller complexion observed with the comparative composition.

Example 7: Coloured Anhydrous Gel

| | 7C (invention) | 7D (comparative) |
|---|---|---|
| YELLOW IRON OXIDE COATED WITH ALUMINIUM STEAROYL GLUTAMATE (3%) NAI-C33-9001-10 from MIYOSHI KASEI | 0.468 | 0.52 |
| RED IRON OXIDE COATED WITH ALUMINIUM STEAROYL GLUTAMATE (3%) NAI-C33-8001-10 from MIYOSHI KASEI | 0.153 | 0.17 |
| BLACK IRON OXIDE COATED WITH ALUMINIUM STEAROYL GLUTAMATE (3%) NAI-C33-7001-10 from MIYOSHI KASEI | 0.063 | 0.07 |
| ANATASE TITANIUM OXIDE COATED WITH ALUMINIUM STEAROYL GLUTAMATE (97/3) (CI: 77891) (NAI-TAO-77891 from MIYOSHI KASEI) | 4.716 | 5.24 |
| Crosslinked polydimethylsiloxane (12%) in cyclopentadimethylsiloxane (Dow Corning 9045 Silicone Elastomer Blend from Dow Corning) | 61.2 | 68 |
| STABILIZED (0.1% BHT) 2-ETHYLHEXYL P-METHOXY-4 CINNAMATE | 1.8 | 2 |
| Dispersion of bismuth oxychloride in 2-ethylhexyl hydroxystearate (70:30) (Timiron Liquid Silver ®) from Merck | 10 | 0 |
| CYCLOPENTADIMETHYLSILOXANE (Dow Corning 245 Fluid from Dow Corning) | qs 100 | qs 100 |

Procedure:

The dispersion of bismuth oxychloride in 2-ethylhexyl hydroxystearate is introduced into the anhydrous mixture comprising the pigments, with moderate stirring.

Makeup Evaluation

The compositions are applied to half the face and the makeup result is evaluated. The composition according to the invention comprising the dispersion of bismuth oxychloride in combination with the non-emulsifying silicone elastomer is more luminous than the (comparative) composition that does not contain the dispersion of bismuth oxychloride: the composition according to the invention reflects the light more, in a uniform and continuous manner. The complexion appears younger, with more radiance after application of the composition according to the invention, compared to the duller complexion observed with the comparative composition.

Example 8: Coloured Emulsion

| | 8E (invention) | 8F (comparative) |
|---|---|---|
| MAGNESIUM SULPHATE, 7 H$_2$O | 0.99918 | 0.99918 |
| Microbiologically clean deionized water | 26.818155 | 26.818155 |
| Mica treated with TiO$_2$ + iron oxide, iron/TiO$_2$, and alumina (10 MICRONS) (65.2/33.5/1.0/0.3 w/w %) Coverleaf MF from Catalyst Chemical | 1 | 1 |
| YELLOW IRON OXIDE COATED WITH ALUMINIUM STEAROYL GLUTAMATE (3%) NAI-C33-9001-10 from MIYOSHI KASEI | 1.056 | 1.056 |
| RED IRON OXIDE COATED WITH ALUMINIUM STEAROYL GLUTAMATE (3%) NAI-C33-8001-10 from MIYOSHI KASEI | 0.161 | 0.161 |
| BLACK IRON OXIDE COATED WITH ALUMINIUM STEAROYL GLUTAMATE (3%) | 0.048 | 0.048 |
| ANATASE TITANIUM OXIDE COATED WITH ALUMINIUM STEAROYL GLUTAMATE (97/3) (CI: 77891) | 9.093 | 9.093 |
| PRESERVATIVES | 0.8 | 0.8 |
| DIMETHICONE (and) DIMETHICONE/POLYGLYCERIN-3 CROSSPOLYMER (KSG710 from Shin-Etsu) | 7.65 | 7.65 |
| MIXTURE OF CROSSLINKED POLYALKYLENATED POLYDIMETHYLSILOXANE AND OF POLYDIMETHYLSILOXANE (6 cSt) 27/73 (KSG210 from Shin-Etsu) | 9 | 9 |
| Polydimethylsiloxane (viscosity: 5 cSt) DOW CORNING 200 FLUID 5 CST from Dow Corning | 5 | 5 |
| CYCLOPENTADIMETHYLSILOXANE (Dow Corning 245 Fluid from Dow Corning) | 14.15 | 15.15 |
| OXYETHYLENATED POLYDIMETHYLSILOXANE (DP: 70 - VISCOSITY: 500 cSt) KF6017 from Shin-Etsu | 2.5 | 2.5 |
| STABILIZED (0.1% BHT) 2-ETHYLHEXYL P-METHOXY-4 CINNAMATE | 5 | 5 |
| Dispersion of bismuth oxychloride in 2-ethylhexyl hydroxystearate (70:30) (Timiron Liquid Silver ®) from Merck | 1 | 0 |
| Nacres | 0.3 | 0.3 |
| POWDER OF HEXAMETHYLENE DIISOCYANATE/TRIMETHYLOL HEXYLLACTONE COPOLYMER CONTAINING SILICA (98/2) (size: 10-15 MICRONS (PLASTIC POWDER D 400 from Toshiki Pigment) | 5 | 5 |
| PROPYLENE GLYCOL | 1 | 1 |
| GLYCEROL | 7 | 7 |
| CYCLOPENTADIMETHYLSILOXANE | qs 100 | qs 100 |

Procedure:

The dispersion of bismuth oxychloride in 2-ethylhexyl hydroxystearate is introduced into the fatty phase; the aqueous phase is prepared; and the emulsion is produced by introducing the aqueous phase into the oily phase, using a Rayneri mixer equipped with a deflocculator for the stirring, at room temperature.

Makeup Evaluation

The compositions are applied to half the face and the makeup result is evaluated. The composition according to the invention comprising the dispersion of bismuth oxychloride is more luminous than the composition that does not contain it: the composition according to the invention reflects the light more, in a uniform and continuous manner. The complexion appears younger, with more radiance after application of the composition according to the invention, compared to the duller complexion observed with the comparative composition.

Example 9: Pigmented Water-in-Oil Emulsion

The following composition was prepared and its effect was evaluated after application to the models' skin.

| | |
|---|---|
| Talc | 0.5% |
| Titanium dioxide coated with aluminium stearoyl glutamate | 7.0% |
| Composite pigment (titanium dioxide/FD&C Blue 1 Al lake) [1] | 0.1% |
| Composite pigment (titanium dioxide/Red No. 28 lake/Red 7) [2] | 0.05% |
| Yellow, red and black iron oxides respectively coated with aluminium stearoyl glutamate | 4.0% |
| Pre-dispersion of bismuth oxychloride in 2-ethylhexyl hydroxystearate (70:30) (Biron ® Liquid Silver from Merck) | 3.0% |
| Cyclopentadimethylsiloxane (Dow Corning 245 Fluid) | 22.5% |
| Phenyl trimethicone | 5.0% |
| BIS-PEG/PPG-14/14 DIMETHICONE (and) CYCLOPENTASILOXANE [3] | 1.2% |
| PEG-10 DIMETHICONE [4] | 2.3% |
| DIMETHICONE (and) DIMETHICONE/POLYGLYCERIN-3 CROSSPOLYMER [5] | 3.0% |
| Denatured ethyl alcohol | 9.0% |
| Microbiologically clean deionized water | qs 100% |

[1] Composite pigment constituted of an inorganic core of titanium dioxide having an average size of 20 nm and having a specific surface area of 50 m²/g, an organic lake with the name FD&C Blue 1 Al lake, and produced with a polymethylhydrosiloxane binder (proportions 58.1/40.7/1.2)
[2] Composite pigment constituted of an inorganic core of titanium dioxide having an average size of 20 nm and having a specific surface area of 50 m²/g, an organic lake with the name Red No. 28 lake and organic pigment Red 7, and produced with a polymethylhydrosiloxane binder
[3] ABIL EM 97 from Evonik Goldschmidt
[4] KF 6017 from Shin-Etsu
[5] (3) KSG710 from Shin-Etsu Procedure Introduce all the raw materials except the ethyl alcohol, at room temperature, into a stainless steel beaker.

Roughly mix using a spatula. Mix at high speed (3000 rpm) using a Moritz mixer (small rotor-agitator) until an emulsion is obtained (8 min). Then add the ethyl alcohol and maintain the same stirring for an additional 2 to 3 min.

After application to the skin, and compared to bare skin, the composition of the invention improves the light, the uniformity and the fineness of the grain of the skin with an advantageous healthy glow effect. The bismuth oxychloride dispersed in the 2-ethylhexyl hydroxystearate provides a complexion correcting and unifying effect and also a light-reflecting effect; the composite pigments provide a desaturating effect, an anti-dull complexion colour-correcting effect.

The complexion regains its natural luminosity, with a makeup result that does not mark the features. The composition enables the skin to reflect the light more, in a uniform and continuous manner. The complexion appears younger, with more radiance after application of the composition according to the invention, compared to bare skin.

The invention claimed is:

1. A cosmetic composition in the form of an emulsion comprising at least one fatty phase and at least one aqueous phase and comprising, in a physiologically acceptable medium:
   (i) at least one dispersion of bismuth oxychloride in 2-ethylhexylhydroxystearate; and
   (ii) a phenylated silicone oil having a refractive index of greater than 1.42 and a vapour pressure at room temperature and atmospheric pressure that is non-zero and is less than 0.02 mmHg (2.66 Pa) and wherein the phenyl silicone oil is a phenyl silicone of formula (VII):

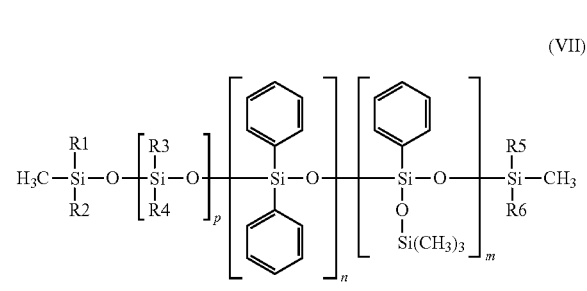

(VII)

wherein R1 to R6, are each independently saturated or unsaturated, linear, cyclic or branched $C_1$-$C_{30}$ hydrocarbon-based radicals, and m, n and p are each independently integers between 0 and 100, with the proviso that the sum n+m is between 1 and 100, wherein a total content of bismuth oxychloride and phenylated silicone oil present in the composition is from 0.01% to 15% by weight relative to the total weight of said composition.

2. The cosmetic composition according to claim 1, wherein a total content of bismuth oxychloride and phenylated silicone oil present in the composition is from 0.5% to 10% by weight relative to the total weight of said composition.

3. The cosmetic composition according to claim 1, wherein the composition is in the form of an oil-in-water emulsion, a water-in-oil emulsion, or a multiple emulsion.

4. The cosmetic composition according to claim 1, wherein the composition comprises an aqueous phase in a content ranging from 10% to 80% by weight relative to the total weight of the composition.

5. The cosmetic composition according to claim 1, wherein the composition comprises an aqueous phase ranging from 30% to 70% by weight relative to the total weight of the composition, and at least 5% by weight relative to the total weight of the composition of at least one $C_2$ to $C_8$ monoalcohol.

6. A cosmetic composition in the form of an emulsion comprising, in a physiologically acceptable medium:
   (i) at least one dispersion of bismuth oxychloride in 2-ethylhexylhydroxystearate;
   (ii) at least one soft focus agent; and
   (iii) at least one phenylated silicone oil having a refractive index of greater than 1.42 and a vapour pressure at room temperature and atmospheric pressure that is non-zero and is less than 0.02 mmHg (2.66 Pa) and wherein the phenyl silicone oil is a phenyl silicone of formula (VII):

(VII)

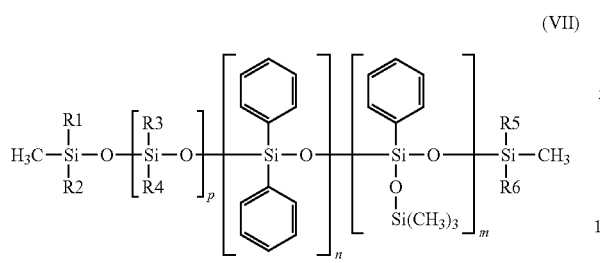

wherein R1 to R6, are each independently saturated or unsaturated, linear, cyclic or branched $C_1$-$C_{30}$ hydrocarbon-based radicals, and m, n and p are each independently integers between 0 and 100, with the proviso that the sum n+m is between 1 and 100, wherein a total content of bismuth oxychloride and phenylated silicone oil present in the composition is from 0.5% to 10% by weight relative to the total weight of said composition.

7. The cosmetic composition according to claim 1, wherein the composition further comprises at least one filler.

8. The composition of claim 1, wherein the composition is suitable for caring for and/or making up skin.

9. The composition of claim 1, wherein the composition is a foundation or complexion corrector.

10. The cosmetic composition according to claim 1, wherein a total content of bismuth oxychloride and phenylated silicone oil present in the composition is from 2% to 3% by weight relative to the total weight of said composition.

11. The cosmetic composition according to claim 6, wherein a total content of bismuth oxychloride and phenylated silicone oil present in the composition is from 2% to 3% by weight relative to the total weight of said composition.

12. A cosmetic composition in the form of a water-in-oil emulsion comprising at least one fatty phase and at least one aqueous phase and comprising, in a physiologically acceptable medium:
(i) at least one dispersion of bismuth oxychloride in 2-ethylhexylhydroxystearate; and
(ii) a phenylated silicone oil having a refractive index of greater than 1.42 and a vapour pressure at room temperature and atmospheric pressure that is non-zero and is less than 0.02 mmHg (2.66 Pa) and wherein the phenyl silicone oil is a phenyl silicone of formula (VII):

(VII)

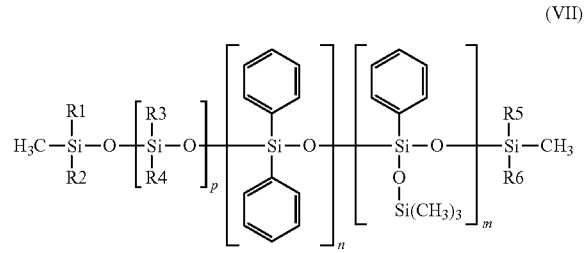

wherein R1 to R6, are each independently saturated or unsaturated, linear, cyclic or branched $C_1$-$C_{30}$ hydrocarbon-based radicals, and m, n and p are each independently integers between 0 and 100, with the proviso that the sum n+m is between 1 and 100.

13. A cosmetic composition in the form of a water-in-oil emulsion, comprising, in a physiologically acceptable medium:
(iii) at least one dispersion of bismuth oxychloride in 2-ethylhexylhydroxystearate:
(iv) at least one soft focus agent; and
(iv) at least one phenylated silicone oil having a refractive index of greater than 1.42 and a vapour pressure at room temperature and atmospheric pressure that is non-zero and is less than 0.02 mmHg (2.66 Pa) and wherein the phenyl silicone oil is a phenyl silicone of formula (VII):

(VII)

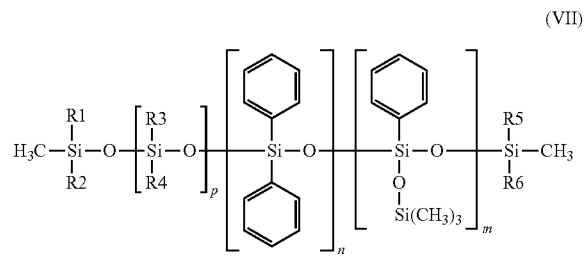

wherein R1 to R6, are each independently saturated or unsaturated, linear, cyclic or branched $C_1$-$C_{30}$ hydrocarbon-based radicals, and m, n and p are each independently integers between 0 and 100, with the proviso that the sum n+m is between 1 and 100.

14. A process for preparing the composition of claim 1, comprising:
a) introducing a dispersion of bismuth oxychloride comprising 68% to 72% by weight of bismuth oxychloride in 28% to 32% by weight of 2-ethylhexyl hydroxystearate relative to the total weight of the dispersion into at least one fatty phase, and
b) combining at least one aqueous phase with the at least one fatty phase with stirring and at room temperature to form the composition.

* * * * *